United States Patent
Gryzwa et al.

(10) Patent No.: US 6,473,649 B1
(45) Date of Patent: Oct. 29, 2002

(54) RATE MANAGEMENT DURING AUTOMATIC CAPTURE VERIFICATION

(75) Inventors: Mark Gryzwa, Woodbury; Qingsheng Zhu, Little Canada, both of MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 09/470,269

(22) Filed: Dec. 22, 1999

(51) Int. Cl.⁷ .................................................. A61N 1/37
(52) U.S. Cl. ........................ 607/28; 600/509; 607/13; 128/901
(58) Field of Search .......................... 607/27, 28, 9, 607/13; 128/901; 600/509

(56) References Cited

U.S. PATENT DOCUMENTS

| | | | |
|---|---|---|---|
| 3,757,792 A | 9/1973 | Mulier et al. | 128/419 P |
| 3,920,024 A | 11/1975 | Bowers | 128/419 PG |
| 4,233,985 A | 11/1980 | Hartlaub et al. | 128/419 PG |
| 4,253,466 A | 3/1981 | Hartlaub et al. | 128/419 PG |
| 4,273,132 A | 6/1981 | Hartlaub et al. | 128/419 PT |
| 4,273,133 A | 6/1981 | Hartlaub et al. | 128/419 PG |
| 4,337,776 A | 7/1982 | Daly et al. | 128/419 PT |
| 4,373,531 A | 2/1983 | Wittkampf et al. | 128/419 PG |
| 4,399,818 A | 8/1983 | Money | 128/419 PG |
| 4,401,120 A | 8/1983 | Hartlaub et al. | 128/419 PT |
| 4,537,201 A | 8/1985 | Delle-Vedove et al. | 128/697 |
| 4,674,508 A | 6/1987 | DeCote | 128/419 PT |
| 4,686,988 A | 8/1987 | Sholder | 128/419 PT |
| 4,762,136 A | 8/1988 | Baker, Jr. | 128/786 |
| 4,779,617 A | 10/1988 | Whigham | 128/419 P |
| 4,821,724 A | 4/1989 | Whigham et al. | 128/419 P |
| 4,858,610 A | 8/1989 | Callaghan et al. | 128/419 PG |
| 4,895,152 A | 1/1990 | Callaghan et al. | 128/419 PG |
| 5,097,832 A | 3/1992 | Buchanan | 128/419 PG |
| 5,103,820 A | 4/1992 | Markowitz | 128/419 OPG |
| 5,161,529 A | 11/1992 | Stotts et al. | 128/419 PG |
| 5,222,493 A | 6/1993 | Sholder | 128/419 P |
| 5,231,986 A | 8/1993 | Bennett | 607/11 |
| 5,243,979 A | 9/1993 | Stein et al. | 607/20 |

(List continued on next page.)

OTHER PUBLICATIONS

"Practical Cardiac Diagnosis", *Cardiac Pacing*, edited by Kenneth A. Ellenbogen, M.D., "Pacemaker Timing Cycles", David L. Hayes, M.D. and Paul A. Levine, M.D., (1992).

*Primary Examiner*—Kennedy Schaetzle
(74) *Attorney, Agent, or Firm*—Nikolai & Mesereau, P.A.; C. G. Mesereau

(57) ABSTRACT

An implantable cardiac rhythm management device capable of automatically detecting intrinsic and evoked response of a patient's heart and suitable for use during capture verification. The device of the present invention may operate in an automatic capture verification mode, wherein an electrocardiogram signal of a patient's heart is received and used by the device to determine whether a stimulation pulse evokes a response by the patient's heart. The device suspends the automatic capture verification mode and/or adjust the detection threshold dependent upon detected and/or measured noise, a determined amplitude of evoked response, a determined modulation in the evoked response, or detected and/or measured artifact. Further, the sensing circuit of the rhythm management device of the present invention reduces afterpotentials that result due to delivery of the stimulation pulses.

40 Claims, 34 Drawing Sheets

U.S. PATENT DOCUMENTS

| | | |
|---|---|---|
| 5,271,395 A | 12/1993 | Wahlstrand et al. ............ 607/9 |
| 5,312,446 A | 5/1994 | Holschbach et al. ........... 607/9 |
| 5,312,453 A | 5/1994 | Shelton et al. ................. 607/19 |
| 5,312,454 A | 5/1994 | Roline et al. .................. 607/22 |
| 5,320,643 A | 6/1994 | Roline et al. .................. 607/28 |
| 5,324,310 A | 6/1994 | Greeninger et al. ........... 607/28 |
| 5,331,966 A | 7/1994 | Bennett et al. ............. 128/696 |
| 5,336,244 A | 8/1994 | Weijand ....................... 607/21 |
| 5,342,406 A | 8/1994 | Thompson ................... 607/22 |
| 5,350,410 A | 9/1994 | Kleks et al. ................... 607/28 |
| 5,365,932 A | 11/1994 | Greenhut .................... 128/696 |
| 5,374,282 A | 12/1994 | Nichols et al. ............... 607/18 |
| 5,391,192 A | 2/1995 | Lu et al. ....................... 607/28 |
| 5,431,693 A | 7/1995 | Schroeppel .................. 607/28 |
| 5,441,524 A | 8/1995 | Rueter et al. ................. 607/18 |
| 5,486,201 A | 1/1996 | Canfield ....................... 607/13 |
| 5,540,729 A | 7/1996 | Weijand ....................... 607/35 |
| 5,564,430 A | 10/1996 | Jacobson et al. ............ 128/697 |
| 5,601,615 A | 2/1997 | Markowitz et al. ............ 607/28 |
| 5,674,258 A | 10/1997 | Henschel et al. .............. 607/19 |
| 5,683,431 A | 11/1997 | Wang ........................... 607/28 |
| 5,755,738 A | 5/1998 | Kim et al. ..................... 607/9 |
| 5,855,594 A | 1/1999 | Olive et al. .................... 607/28 |
| 5,871,512 A | 2/1999 | Hemming et al. ............. 607/28 |
| 5,891,169 A * | 4/1999 | Boheim et al. ................ 607/4 |
| 5,891,171 A * | 4/1999 | Wickham ................... 128/901 |
| 6,067,472 A * | 5/2000 | Vonk et al. .................... 607/13 |
| 6,192,273 B1 * | 2/2001 | Igel et al. .................... 600/518 |
| 6,226,551 B1 * | 5/2001 | Zhu et al. ...................... 607/28 |
| 6,249,701 B1 * | 6/2001 | Rajasekhar et al. ............ 607/9 |

\* cited by examiner

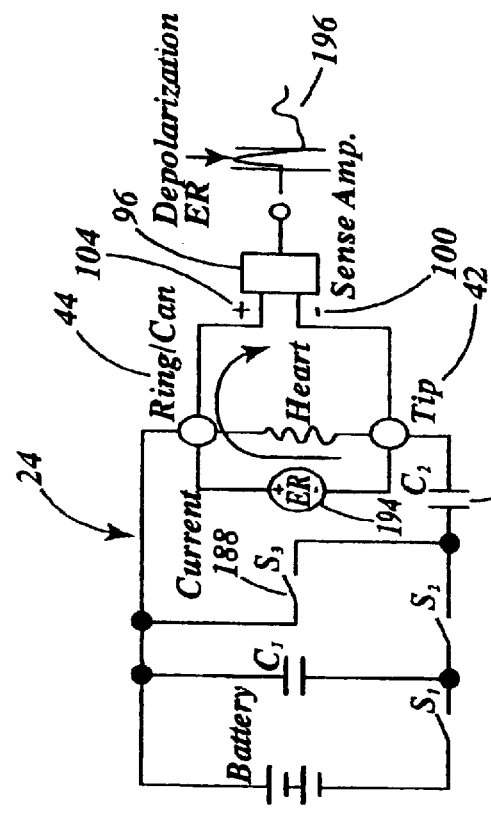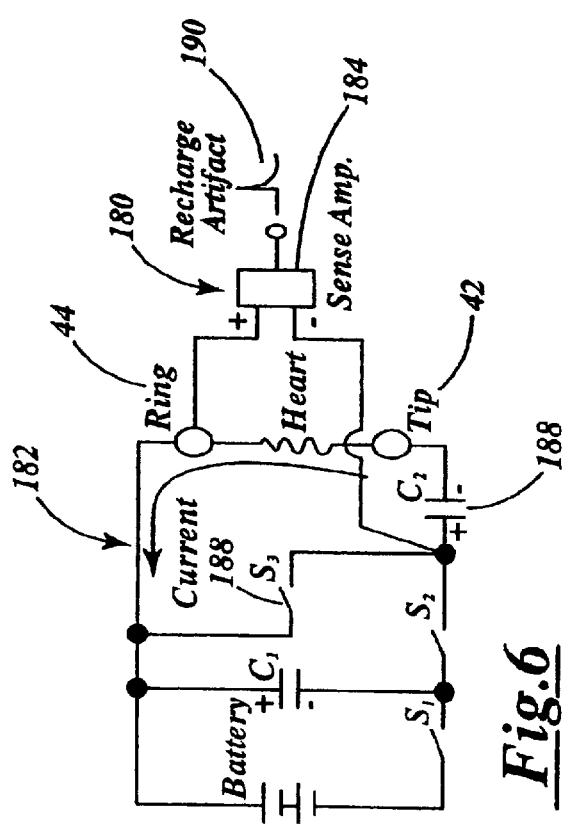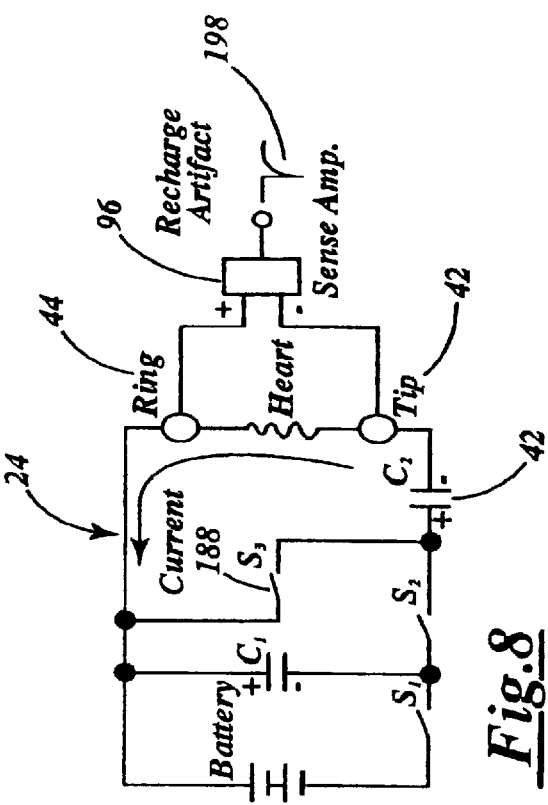
Fig.7
Fig.6
Fig.8

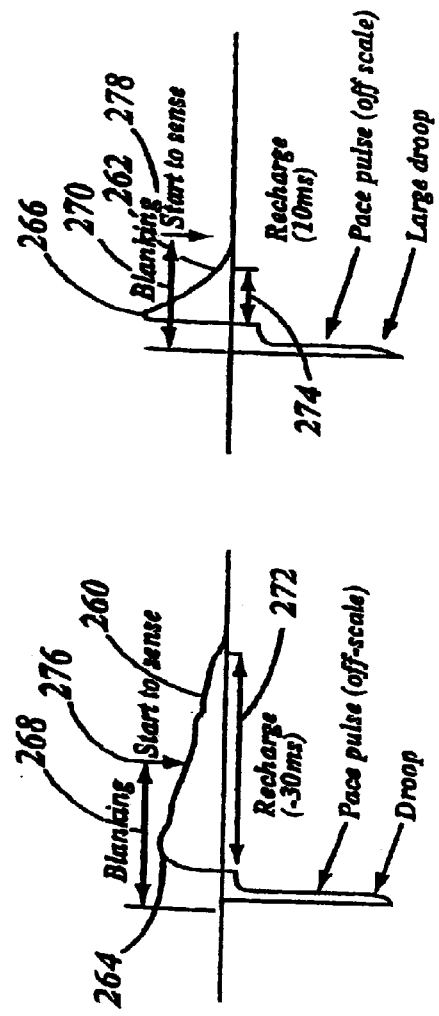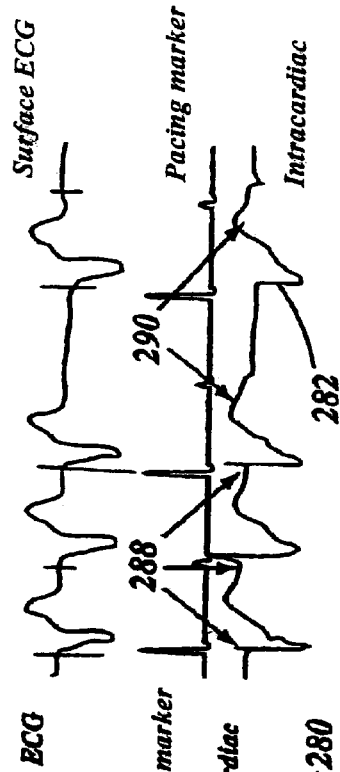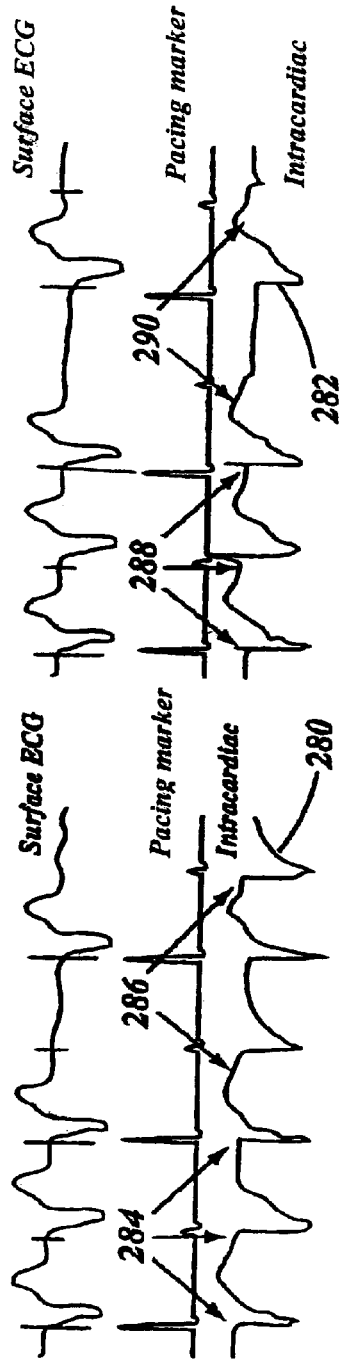

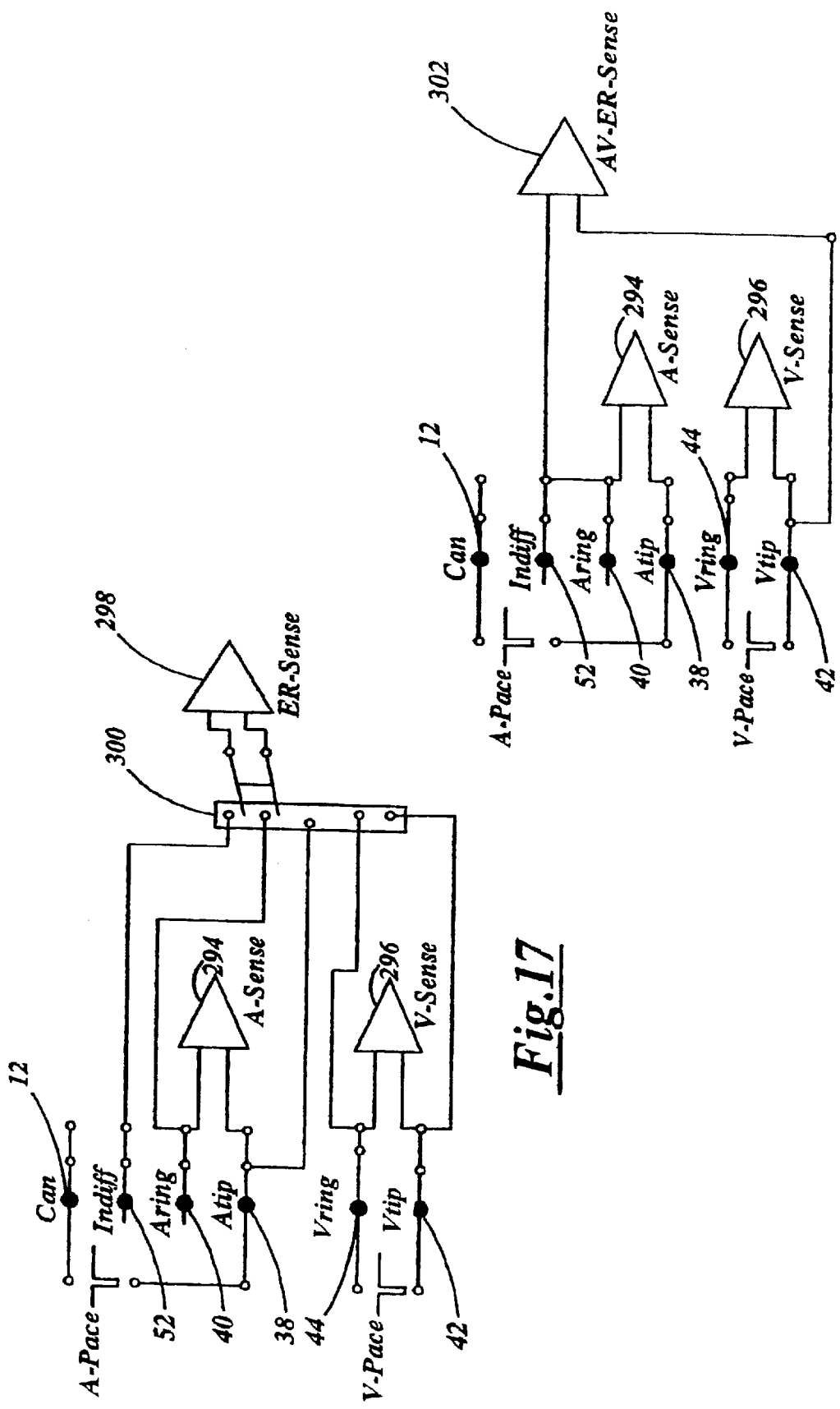

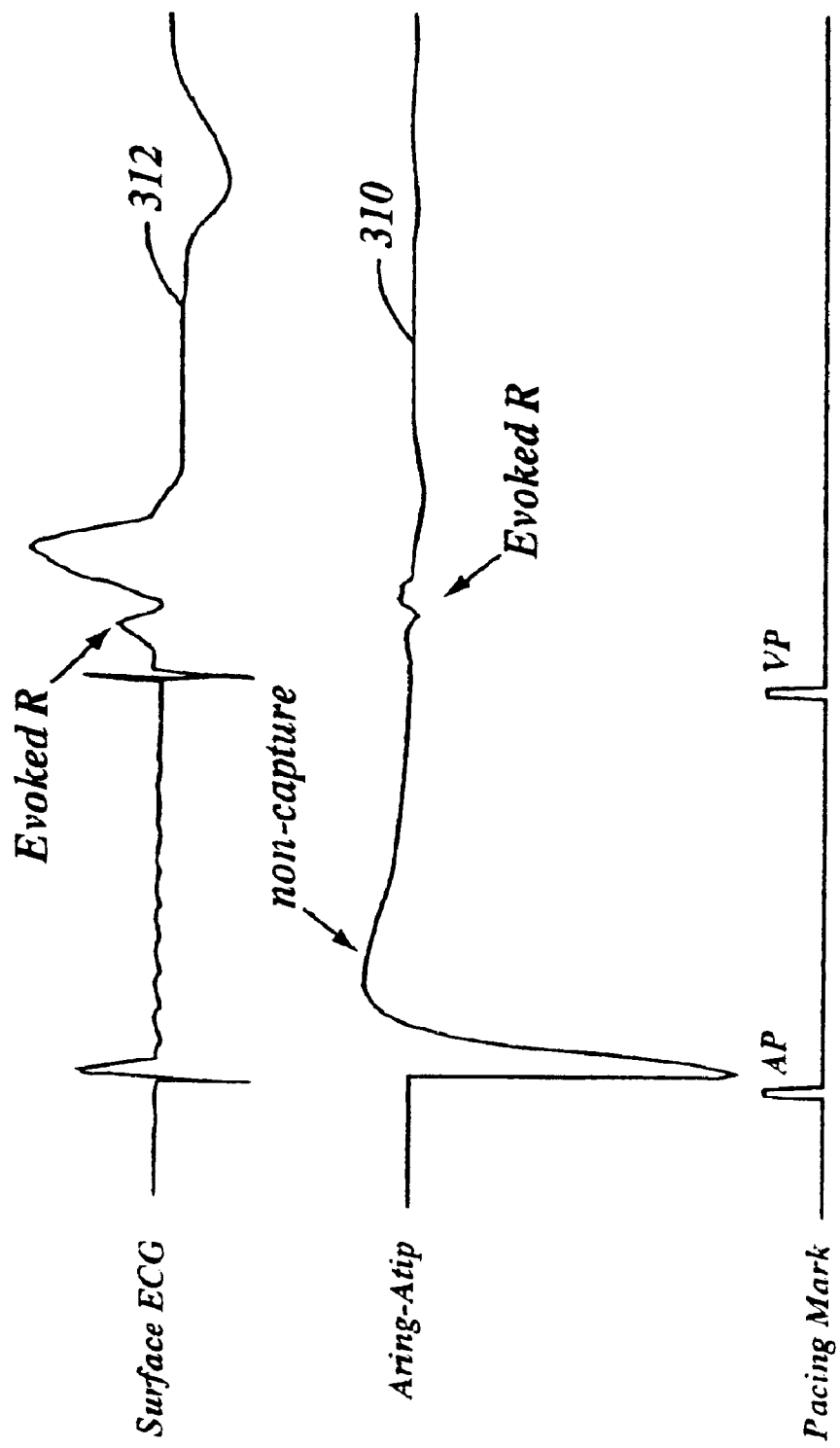

RATE MANAGEMENT DURING AUTOMATIC CAPTURE VERIFICATION

BACKGROUND OF THE INVENTION

I. Field of the Invention

This invention relates generally to a device for stimulating cardiac tissue, and more particularly relates to an implantable cardiac rhythm management device capable of automatically detecting intrinsic and evoked response of a patient's heart. The device of the present invention may operate in an automatic capture verification mode, wherein an electrocardiogram signal of a patient's heart is received and used by the device to determine whether a stimulation pulse evokes a response by the patient's heart. The rhythm management device may automatically adjust the detection threshold during a normal mode or an automatic capture verification mode. Also, the device may suspend the automatic capture verification mode and/or adjust the detection threshold dependent upon detected and/or measured noise, a determined amplitude of evoked response, a determined modulation in the evoked response, or detected and/or measured artifact. Further, the sensing circuit of the rhythm management device of the present invention reduces afterpotentials that result due to delivery of the stimulation pulses.

II. Discussion of the Prior Art

Cardiac rhythm management devices have enjoyed widespread use and popularity over the years as a means for supplanting some or all of an abnormal heart's natural pacing functions. The various heart abnormalities remedied by these stimulation devices include total or partial heart block, arrhythmias, myocardial infarctions, congestive heart failure, congenital heart disorders, and various other rhythm disturbances within the heart. The cardiac rhythm management devices generally include a pulse generator for generating stimulation pulses to the heart electrically coupled to an electrode lead arrangement (unipolar or bipolar) positioned adjacent or within a pre-selected heart chamber for delivering pacing stimulation pulses.

Regardless of the type of cardiac rhythm management device that is employed to restore the heart's natural rhythm, all operate to stimulate excitable heart tissue cells adjacent to the electrode of the lead. Myocardial response to stimulation or "capture" is a function of the positive and negative charges found in each myocardial cell within the heart. More specifically, the selective permeability of each myocardial cell works to retain potassium and exclude sodium such that, when the cell is at rest, the concentration of sodium ions outside of the cell membrane is significantly greater than the concentration of sodium ions inside the cell membrane, while the concentration of potassium ions outside the cell membrane is significantly less than the concentration of potassium ions inside the cell membrane.

The selective permeability of each myocardial cell also retains other negative particles within the cell membrane such that the inside of the cell membrane is negatively charged with respect to the outside when the cell is at rest. When a stimulus is applied to the cell membrane, the selective permeability of the cell membrane is disturbed and it can no longer block the inflow of sodium ions from outside the cell membrane. The inflow of sodium ions at the stimulation site causes the adjacent portions of the cell membrane to lose its selective permeability, thereby causing a chain reaction across the cell membrane until the cell interior is flooded with sodium ions. This process, referred to as depolarization, causes the myocardial cell to have a net positive charge due to the inflow of sodium ions. The electrical depolarization of the cell interior causes a mechanical contraction or shortening of the myofibril of the cell. The syncytial structure of the myocardium will cause the depolarization originating in any one cell to radiate through the entire mass of the heart muscle so that all cells are stimulated for effective pumping. Following heart contraction or systole, the selective permeability of the cell membrane returns and sodium is pumped out until the cell is re-polarized with a negative charge within the cell membrane. This causes the cell membrane to relax and return to the fully extended state, referred to as diastole.

In a normal heart, the sino-atrial (SA) node initiates the myocardial stimulation of the atrium. The SA node comprises a bundle of unique cells disposed within the roof of the right atrium. Each cell membrane of the SA node has a characteristic tendency to leak ions gradually over time such that the cell membrane periodically breaks down and allows an inflow of sodium ions, thereby causing the SA node cells to depolarize. The SA node cells are in communication with the surrounding atrial muscle cells such that the depolarization of the SA node cells causes the adjacent atrial muscle cells to depolarize. This results in atrial systole wherein the atria contract to empty blood into the ventricles.

The atrial depolarization from the SA node is detected by the atrioventricular (AV) node which, in turn, communicates the depolarization impulse into the ventricles via the Bundle of His and Purkinje fibers following a brief conduction delay. In this fashion, ventricular systole lags behind atrial systole such that the blood from the ventricles pumps through the body and lungs after being filled by the atria. Atrial and ventricular diastole follow wherein the myocardium is re-polarized and the heart muscle relaxed in preparation for the next cardiac cycle. It is when this system fails or functions abnormally that a cardiac rhythm management device may be needed to deliver an electronic stimulation pulse for selectively depolarizing the myocardium of the heart so as to maintain proper heart rate and synchronization of the filling and contraction of the atrial and ventricular chambers of the heart.

The success of a stimulation pulse in depolarizing or "capturing" the selected chamber of the heart hinges on whether the output of the stimulation pulse as delivered to the myocardium exceeds a threshold value. This threshold value, referred to as the capture threshold, is related to the electrical field intensity required to alter the permeability of the myocardial cells to thereby initiate cell depolarization. If the local electrical field associated with the stimulation pulse does not exceed the capture threshold, then the permeability of the myocardial cells will not be altered enough and thus no depolarization will result. If, on the other hand, the local electrical field associated with the stimulation pulse exceeds the capture threshold, then the permeability of the myocardial cells will be altered sufficiently such that depolarization will result.

Changes in the capture threshold may be detected by monitoring the efficacy of stimulating pulses at a given energy level. If capture does not occur at a particular stimulation energy level which previously was adequate to effect capture, then it can be surmised that the capture threshold has increased and that the stimulation energy should be increased. On the other hand, if capture occurs consistently at a particular stimulation energy level over a relatively large number of successive stimulation cycles, then it is possible that the capture threshold has decreased such that the stimulation energy is being delivered at level higher than necessary to effect capture. Alternatively, the electrocardiogram signal may be utilized to surmise whether a change in amplitude in the electrocardiogram signal at a particular time is the result of an intrinsic event or evoked response.

The ability of a rhythm management device to detect capture is desirable in that delivering stimulation pulses having energy far in excess of the patient's capture threshold is wasteful of the rhythm management device's limited power supply. In order to minimize current drain on the power supply, it is desirable to automatically adjust the device such that the amount of stimulation energy delivered to the myocardium is maintained at the lowest level that will reliably capture the heart. To accomplish this, a process known as capture verification must be performed wherein the rhythm management device monitors to determine whether an evoked depolarization occurs in the pre-selected heart chamber following the delivery of each pacing stimulus pulse to the pre-selected chamber of the heart.

At times, a stimulation pulse may be delivered coincidental to a depolarization by an intrinsic beat (hereinafter referred to as "fusion" or "a fusion beat"). From a surface ECG, the fusion beats manifest themselves by a pacing spike followed by an intrinsic QRS complex. Further, due to intrinsic detection latency, a stimulation pulse may be delivered after intrinsic activation has already begun (hereinafter referred to as pseudo-fusion). From a surface ECG, it is seen that the stimulation pulse falls inside the intrinsic QRS complex. The stimulation pulses may or may not capture the myocardium. During normal delivery of a stimulation pulse, fusion and/or pseudo-fusion beats may be of little consequence except some energy loss due to unnecessary pacing output. However, during autocapture or autothresholding, the impact of fusion or pseudo-fusion can be rather different.

During autocapture or autothreshold, fusion beats or noise may be detected as capture for amplitude-based detection methods. Thus, even though the stimulation pulse may be below threshold, the evoked response detection remains positive. As a result, the threshold may be identified at a lower amount than the actual threshold. Pseudo-fusion may be detected either as capture or non-capture depending upon timing of the occurrence of pseudo-fusion. If a stimulation pulse is delivered at an earlier portion of the QRS complex, then the stimulation pulse is more likely to be detected as capture and the consequence is the same as a fusion beat. If pseudo-fusion is detected as non-capture, a backup pulse may be issued between the QRS complex and a T wave which is undesirable.

During automatic threshold determination, pseudo-fusion beats may cause false detection of either capture or non-capture. When pseudo-fusion is detected as capture, an error in threshold measurement may arise. In many instances, occurrence of pseudo-fusion is caused by the inherent latency of sensing an intrinsic event. This latency often results from a sensing threshold level that is normally higher than front portions of the QRS complex of the endocardial signals, which prevents a detection by the rhythm management device of the front portions of the QRS complex. Other factors that may contribute to latency in intrinsic detection include sensing channel phase delay. Thus, there is a need for a method that reduces unnecessary autothresholding, error in threshold measurement, and other undesirable affects of fusion and pseudo-fusion during capture verification and autothreshold determination. There is a further need for a rhythm management device that manages the timing of delivery of backup stimulation that avoids stimulating during undesirable portions of a timing cycle.

Other factors, including afterpotential, affect the ability of a device to automatically set an accurate detection or sensing threshold. For example, the conventional pacemaker typically includes a pacing output circuit designed to selectively generate and deliver stimulus pulses through a lead to one or more electrodes positioned in the heart of a patient. The pacing output circuit includes a power supply, switches, a pacing charge storage capacitor, and a coupling capacitor, all of which cooperatively operate under the direction of a controller to perform a charging cycle, a pacing cycle, and a recharging cycle. The capacitance of the pacing charge storage capacitor typically ranges between 10–30 microfarads so as to develop a sufficient pacing charge for stimulating the heart. The capacitance of the coupling capacitor typically ranges between 15 to 40 microfarads with 33 microfarads being typical. A capacitor having a capacitance in this range was believed necessary to deliver sufficient energy to the heart.

The charging cycle involves manipulation of switches such that the pacing charge storage capacitor is charged up to a predetermined voltage level. The pacing cycle involves manipulating the switches such that the voltage within the pacing charge storage capacitor may be discharged through the coupling capacitor to the electrodes of the pacemaker. The recharging cycle involves further manipulation of the switches for a predetermined period of time following the pacing pulse to allow the coupling capacitor to be discharged.

While the conventional pacing circuit is generally effective in delivering stimulus pulses to a selected chamber of the heart, it has been found that the detection of evoked depolarization or capture verification is rendered very difficult due to polarization voltages or "afterpotential" which develop at the heart tissue/electrode interface following the application of the stimulation pulses. The ability to verify capture is further affected by other variables including patient activity, body position, drugs being used, lead movement, noise etc.

In the past, the large capacitance of the coupling capacitor was believed necessary in order to sufficiently block any DC components from the heart and to minimize pace pulse voltage droop. However, the large capacitance of the coupling capacitor causes a charge dissipation or "afterpotential" which is relatively large (100 mV or greater) and which decays exponentially over a relatively long period of time (100 milliseconds). This is particularly troublesome due to the fact that the evoked potential of the heart tissue is small in amplitude relative to the polarization voltage or "afterpotential" (100 mV). The amplitude of the evoked potential corresponding to a P-wave typically ranges between 1–5 mV and the amplitude of the evoked potential corresponding to an R-wave typically ranges between 5–2 mV.

Further, the long decay period of the polarization voltage or "afterpotential" effectively masks the evoked potential, which typically begins within approximately (10–40) milliseconds after the stimulation pulse to a selected chamber of the heart. It will be appreciated that this creates difficulty in detecting the evoked response of the heart following the delivery of stimulus pulses. In that evoked response is indicative of capture, the undesirable masking of the evoked response by "afterpotential" thus hampers the ability of the pacemaker to conduct automatic capture verification. Hence, there is a need for a rhythm management device that decreases and/or shortens the pacing afterpotential with minimal increase of the leading edge voltage pacing threshold. It is also desirable to reduce the number or complexity of the implanted components and, thus, there is a need for a system having a stimulation/sensing circuit that minimizes the number of required electrodes positioned within the heart for sensing a response evoked by a stimulation pulse directed to a pre-selected chamber of the heart.

U.S. Pat. No. 4,686,988 to Sholder teaches the use of a separate sensing electrode connected to a detector for detecting P-waves in the presence of atrial stimulation pulses, wherein the P-wave detector has an input bandpass characteristic selected to pass frequencies that are associated with P-waves. U.S. Pat. No. 4,858,610 to Callaghan et al. teaches the use of charge dumping following delivery of the stimulation pulse to decrease lead polarization and also the use of separate pacing and sensing electrodes to eliminate the polarization problem on the sensing electrode. The techniques of the '610 patent and '988 patent, which involve using a separate electrode located at some distance from the stimulating electrode for the purpose of isolating the polarization voltages or "afterpotential" are not completely desirable in that they require the additional cost and complexity of the additional sensing electrode.

U.S. Pat. No. 5,324,310 to Greeninger et al. teaches the use of the "ring-to-ring" sensing with corresponding atrial and ventricular EGM amplifiers whose outputs are multiplied and compared to a predetermined threshold to determine capture. U.S. Pat. No. 5,486,201 to Canfield discloses an active discharge circuit having a switching device which sequentially and repeatedly couples a charge transfer capacitor to the coupling capacitor to transfer charge therebetween and thereby actively discharge the coupling capacitor. None of these devices reduce or shorten the pacing afterpotentials through the use of a simplified pacing output. The present invention addresses these and other needs that will become apparent to those skilled in the art.

Hence, there is a need for a cardiac rhythm management device that attenuates polarization voltages or "afterpotentials" which develop at the heart tissue/electrode interface following the delivery of a stimulus to the heart tissue, and which minimizes the number of required components of the cardiac pacing system. There is a further need for a device that automatically adjust the detection threshold during a normal mode or an automatic capture verification mode. There is a still further need for a device capable of suspending the automatic capture verification mode and/or capable of adjusting the detection threshold dependent upon detected and/or measured noise, a determined amplitude of evoked response, a determined modulation in the evoked response, and detected and/or measured artifact.

SUMMARY OF THE INVENTION

The present invention provides for a cardiac rhythm management device capable of automatically detecting intrinsic and evoked response of a patient's heart during a normal mode or capture verification mode. The implantable cardiac rhythm management device of the present invention generally includes a pulse generator that generates stimulation pulses, a controller having a timing circuit, sensing circuit and stimulation circuit for controlling activation of the pulse generator and delivery of the stimulation pulses, and an electrode lead arrangement electrically coupled to the controller. The rhythm management device further includes an adjustable detection threshold operable in a normal or autocapture verification mode, that may be adjusted or suspended dependant upon one or more of the following: detected and/or measured noise, a determined amplitude of evoked response, a determined modulation in the evoked response, and detected and/or measured artifact. The electrode lead arrangement of known suitable construction is positioned within the patient's heart and is electrically coupled to the controller, wherein electrocardiogram signals are electrically conducted to the controller from the electrodes. The electrocardiogram signal includes electrical impulses corresponding to a cardiac depolarization and noise.

In an embodiment of the present invention, the controller detects an evoked response of the patient's heart from the electrocardiogram signal, determines an amplitude associated with the evoked response, and adjusts the detection threshold dependent upon the determined amplitude. Further, the controller may determine a value associated with modulation of the evoked response, wherein the value is determined from the amplitude of a detected evoked response. Once the value associated with modulation is determined, the controller may adjust the detection threshold dependant upon the value associated with modulation. The value associated with modulation may be determined from a respiration modulation index and evoked response filter index.

In another embodiment of the present invention, the controller may also include a means for determining an amount associated with an artifact baseline of the electrocardiogram signal. In this embodiment the detection threshold is set greater than the amount associated with the artifact baseline and less than a minimum of maximum amplitudes of the evoked response over a predetermined number of beats. The minimum of maximum amplitudes of the evoked response is determined from the electrocardiogram signal as described below in greater detail.

The sensing circuit includes a sense amplifier electrically connected to the electrodes and controller in a manner wherein a polarity of an amplitude of the electrocardiogram signal corresponding to an evoked response is opposite a polarity of an amplitude of the electrocardiogram signal corresponding to afterpotential. Also, a positive pole of the sense amplifier is coupled to an indifferent contact, and a negative pole of the sense amplifier is coupled to the electrodes. The peaks associated with evoked response are thus distinguished from peaks related to afterpotential, thereby eliminating the need for peak to peak detection. The stimulation circuit may also include a coupling capacitor arrangement that reduces afterpotentials, wherein the coupling capacitor arrangement includes a capacitor having a capacitance less than 5 microfarads.

In another embodiment of the present invention, the sensing circuit includes a pre-amplifier electrically coupled to the electrodes, a first high pass coupling capacitor electrically coupled between the electrodes and the pre-amplifier, a blanking switch electrically coupled between the high pass coupling capacitor and the pre-amplifier, and a dedicated evoked response amplifier. Alternatively, the sensing circuit may include a first coupling capacitor operatively coupled to a second coupling capacitor, and a switching means for selectively coupling the second coupling capacitor in series with the first coupling capacitor so as to reduce the effective capacitance of the first and second coupling capacitor and thereby attenuate afterpotentials.

In still another embodiment of the rhythm management device of the present invention, the controller detects the presence of noise in the electrocardiogram signal. Further, the controller may determine a value associated with an amplitude of the detected noise. Once the value associated with an amplitude of the detected noise is determined, the controller may adjust the detection threshold dependant upon the value associated with the amplitude of the detected noise. The controller may also include a memory means for storing the determined value associated with an amplitude of noise over a plurality of detected cardiac depolarization, wherein the controller adjusts the sensing threshold dependant upon the determined value associated with an amplitude of noise corresponding to prior detected cardiac depolarization.

OBJECTS

It is accordingly a principal object of the present invention to provide a rhythm management device that may automatically adjust the detection threshold on a beat by beat basis.

Another object of the present invention is to provide a rhythm management device capable of automatically adjusting the detection threshold during an automatic capture verification sequence.

A further object of the present invention is to provide a rhythm management device capable of suspending an autocapture sequence dependent upon detected and/or measured noise, a determined amplitude of evoked response, a determined modulation in the evoked response, or detected and/or measured artifact.

Still another object of the present invention is to provide a rhythm management device that automatically adjusts the detection threshold without iterating the detection threshold level.

Yet another object of the present invention is to provide a rhythm management device that reduces potential error in autocapture and autothreshold determination.

A further object of the present invention is to provide a rhythm management device that reduces the effects of afterpotentials during autocapture verification.

These and other objects and advantages of the present invention will become readily apparent to those skilled in the art from a review of the following detailed description of the preferred embodiment especially when considered in conjunction with the claims and accompanying drawings in which like numerals in the several views refer to corresponding parts.

DESCRIPTION OF THE DRAWINGS

FIG. 6 is a partial schematic of a conventional evoked response sensing circuit showing the direction of flow of the signal and resulting polarity of the amplitude of the signal associated with artifact;

FIG. 7 is a partial schematic of the sensing circuit of the present invention showing the direction of flow of the electrocardiogram signal and resulting polarity of the amplitude of the signal associated with the evoked response;

FIG. 8 is a partial schematic of the sensing circuit of the present invention showing the direction of flow of the electrocardiogram signal and resulting polarity of the amplitude of the signal associated with artifact;

FIG. 13 depicts a resulting pacing waveform observable between the ring and tip of a pacing lead positioned within the heart of a patient, when utilizing a conventional pacing circuit;

FIG. 14 depicts a resulting pacing waveform observable between the ring and tip of a pacing lead positioned within the heart of a patient, when utilizing the afterpotential attenuation means of the present invention;

FIG. 15 shows a strip chart tracing of the capture and noncapture sense signal when utilizing a pacing circuit having a 15 microfarad coupling capacitor with a recharge time of 30 milliseconds, together with a strip chart tracing of a surface ECG for reference;

FIG. 16 shows a strip chart tracing of the capture and noncapture sense signal when utilizing a pacing circuit having a 1 microfarad coupling capacitor with a recharge time of 10 milliseconds, together with a strip chart tracing of a surface ECG for reference;

FIG. 17 is a schematic diagram of a portion of an alternate embodiment of the cardiac rhythm management device's pacing/sensing circuitry in accordance with the present invention;

FIG. 18 is a schematic diagram of an alternate embodiment of a portion of the pacing/sensing circuitry in accordance with the present invention;

FIG. 21 depicts waveforms resulting from a first atrial pacing stimulus and a later ventricular pacing stimulus, wherein a first waveform is sensed with the atrial ring electrode and atrial tip electrode of the atrial pacing lead and a second waveform shown for comparison is sensed with a surface ECG, while utilizing a conventional coupling capacitor, and wherein the pacing output or stimulus is below the required threshold output;

DESCRIPTION OF THE PREFERRED EMBODIMENT

The present invention represents broadly applicable improvements to cardiac rhythm management devices. Those skilled in the art will appreciate that the present invention may find application in a variety of implantable or external cardiac rhythm management devices. For purposes of illustration and ease of discussion, the present invention may be described in connection with an implantable rate adaptive cardiac pacer Thus, the embodiments detailed herein are intended to be taken as representative or exemplary of those in which the improvements of the invention may be incorporated and are not intended to be limiting.

Figure 1:
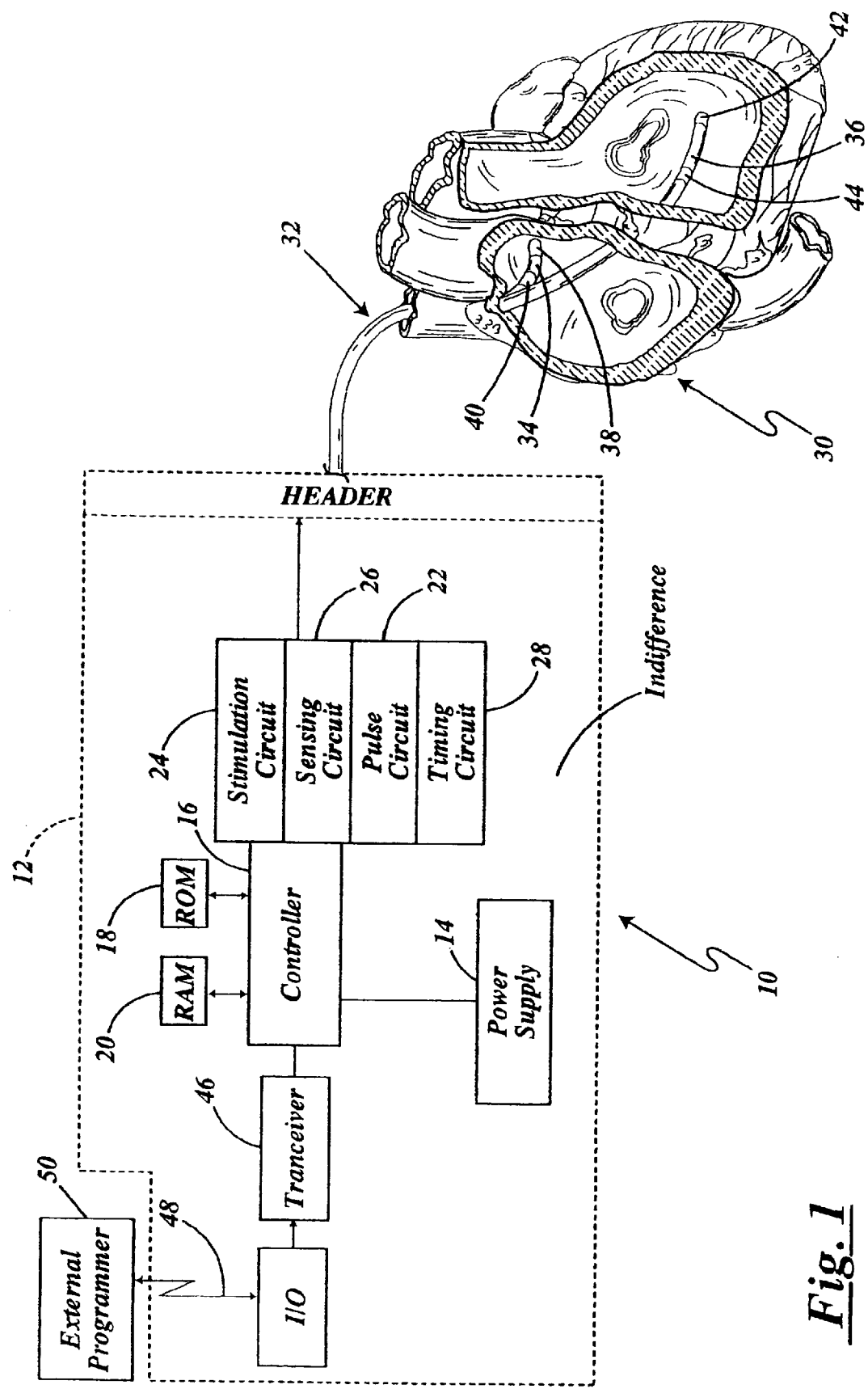
FIG. 1 is a partial sectional fragmentary block diagram depicting a cardiac rhythm management device incorporating a controller having a sensing circuit for automatic capture detection in accordance with the present invention.

Referring first to FIG. 1, an implantable rate adaptive cardiac pacer 10 having an external housing or can represented by dotted box 12 is shown, wherein a power supply 14 and controller 16 are contained therein. The controller 16 may be in any of several forms including a dedicated state device or a microprocessor with code, and may include ROM memory 18 for storing programs to be executed by the controller and RAM memory 20 for storing operands used in carrying out the computations by the controller 16. The controller 16 may include generally a pulse generator 22, stimulation circuit 24, sensing circuit 26 and timing circuit 28 electrically coupled together in known suitable fashion for selectively delivering electrical stimulation pulses to a patient's heart 30. The sensing circuit 26 is utilized by the controller 16 to detect at least one of intrinsic and paced stimulations of the patient's heart 30. As described below in greater detail, the sensing circuit 26 may include a dedicated evoked response sense amplifier, with multiplexer coupled thereto in a known suitable fashion, wherein the evoked response sense amplifier may be utilized in either atrial or ventricular sensing. One or more leads 32 of known suitable construction may be electrically connected to the cardiac rhythm management device 10 through a header of the housing 12. The split lead 32 illustrated in FIG. 1 includes an atrial segment 34 having electrodes 38 and 40 positioned in the right atrium for pacing and sensing therein, and a ventricular segment 36 having electrodes 42 and 44 positioned in the right ventricle for pacing and sensing therein. The electrodes 38–44 are electrically coupled to the controller 16 of the cardiac rhythm management device 10 in a known suitable fashion. A transceiver 46 is cooperatively operable with a conventional input/output module 48 for transmitting and receiving information to and from an external programmer 50.

Figure 2:
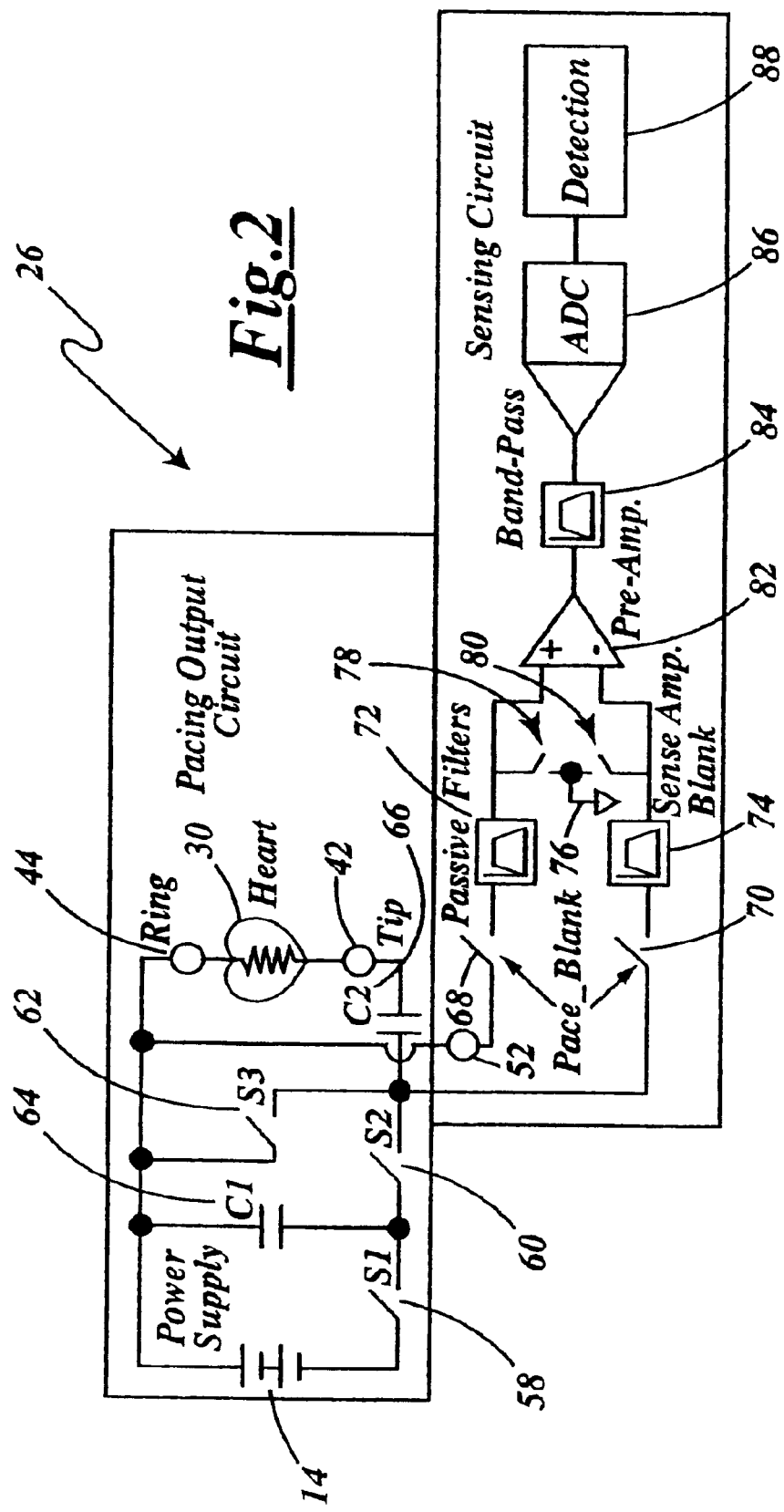
FIG. 2 is a schematic diagram of an embodiment of a portion of the rhythm management device's stimulation or pacing circuit and sensing circuit.

Referring now to FIG. 2, a portion of the embodiment of the stimulation circuit 24 and sensing circuit 26 shown in FIG. 1 is illustrated in greater detail. Those skilled in the art will appreciate that the stimulation and sensing circuits 24 and 26 respectively may be modified slightly to sense for atrial evoked response or to sense for ventricular evoked response. Thus, the description of the pacing/sensing circuit as shown in FIG. 2 should not be construed as limiting. As will be explained below, the improved circuit 26 is capable of quickly attenuating any polarization voltages or "afterpotential" which result due to the application of stimulus pulses to the heart 30. By attenuating the polarization voltages or "afterpotential" in this fashion, the improved circuit 26 facilitates the task of capture verification in that the presence or absence of evoked responses may be readily determined without the masking caused by afterpotential. Capture verification advantageously allows the rhythm management device 10 to automatically adjust the pacing output parameters and/or the detection threshold so as to minimize power consumption while assuring therapeutic efficacy.

In the embodiment shown in FIG. 2, the circuit 26 of the present invention includes a power supply or battery 14, a first switch (S1) 58, a second switch (S2) 60, a third switch (S3) 62, a pacing charge storage capacitor (C1) 64, and an afterpotential reduction capacitor/coupling capacitor (C2) 66, all of which are cooperatively operable under the direction of a controller 16 of known suitable construction. The power supply or battery 14 is preferably the battery provided to power the rhythm management device 10 and may comprise any number of commercially available batteries suitable for pacing applications. The switches 58–62 are preferably carried out via any number of conventionally available microprocessor-directed semiconductor integrated circuit switching means. The pacing charge storage capacitor 64 may also comprise any number of conventional storage capacitors, but is preferably provided with a capacitance in the range of 10–30 microfarads so as to develop a sufficient pacing charge for stimulating the heart 30. The primary function of the coupling capacitor 66 is to quickly attenuate the A polarization voltage or "afterpotential" which result from pacing and additionally block any DC signals from reaching the heart 30 during pacing. The coupling capacitor 66 has a capacitance in the range less than 5 microfarads, with a 2.2 microfarad capacitor being preferred.

The sensing portion of the sensing circuit 26 includes pace blanking switches 68 and 70, passive filters 72 and 74, voltage reference 76, sense amplifier blanking switches 78 and 80, preamplifier 82, band pass filter 84, analog to digital converter 86 and detection comparator 88. The controller 16 is operatively coupled to the circuit 26 and controls the opening and closing of switches 68, 70, 78, and 80. Although switches 68, 70, 78, and 80 are illustrated as discrete components, those skilled in the art will appreciate that they may comprise any number of commercially available microprocessor-directed semiconductor integrated circuit switching means. The pace blanking switches 68 and 70 are closed independently to detect an evoked response from the corresponding pacing electrode, and the shortening of the pacing afterpotential by using a reduced capacitance coupling capacitor 66 allows pacing and sensing of the evoked response from the same electrodes. The intrinsic sensing channel may also be shared for efficient system operation. By shortening the pacing afterpotential, the recharge time of the coupling capacitor 66 may be reduced from a conventional time of greater than 20 milliseconds to under 10 milliseconds. This shortened time usually lapses before the onset of an evoked response. In turn, the sense amplifier blanking time may be reduced from a conventional 30 milliseconds to under 15 milliseconds with 12 milliseconds being preferred. This shortened blanking period in conjunction with the shortening of the pacing afterpotential increases the likelihood of detecting an evoked response.

Having described the constructional features of the embodiment of the pacing and sensing circuit shown in FIG. 2, the mode of use for these circuits will next be described in greater detail. The controller 16 implements a preprogrammed sequence to control the charging cycle, pacing cycle, and recharge cycle of the pacing output circuit. The charging cycle is characterized as having the first switch 58 in a closed state with the second switch 60 and third switch 62 in an open state. In this configuration, the pacing charge storage capacitor 64 may be charged up to a predetermined pacing voltage level, such as 3 volts. After the pacing charge storage capacitor 64 has been charged up to the predetermined pacing voltage level, the pacing cycle then operates to deliver the pacing charge from the pacing charge storage capacitor 64 to the heart 30 in accordance with a predetermined timing protocol.

To accomplish the pacing cycle, the first switch 58 is opened and third switch 62 remains opened and the second switch 60 is closed. This allows the voltage within the pacing charge storage capacitor 64 to be discharged through the coupling capacitor 66 to the tip electrode 42 positioned in the heart 30. The coupling capacitor 66 is less than 5 microfarads. This, once again, effectively blocks any significant DC signals from reaching the heart 30, while shortening the pacing afterpotential.

The recharge cycle involves keeping open the first switch 58 and opening the second switch 60 while closing the third switch 62. This allows the circuit 24 to passively recharge, such that the charge within the heart 30 is allowed to flow back into the pacing output circuit to balance out. During this passive recharge period, the charge on the coupling capacitor 66 is such that the signal decays over a short period of time and less than the required blanking period preceding detection of any evoked response from the heart 30. This is because the evoked responses from the heart 30 typically begins within 12 milliseconds from the delivery of a stimulus pulse to the atrium and within 20 milliseconds from the delivery of a stimulus pulse to the ventricle, which is substantially longer than the required recharge time. Advantageously, it has been found that reducing the overall capacitance of the coupling capacitor 66 quickly attenuates the polarization voltages or "afterpotentials" which result immediately following the application of a stimulus pulse such that the evoked responses within the heart 30 will not be masked or buried within the "afterpotential." By eliminating the adverse affects of "afterpotential" in this fashion, the rhythm management device 10 can easily sense an evoked response and track the capture threshold of the heart 30 over time. Those skilled in the art will appreciate that with the continuous evaluation of an evoked response, the rhythm management device 10 may be automatically adjusted to maintain an optimal pacing stimulus level which ensures safe pacing while minimizing power consumption.

Figure 3:
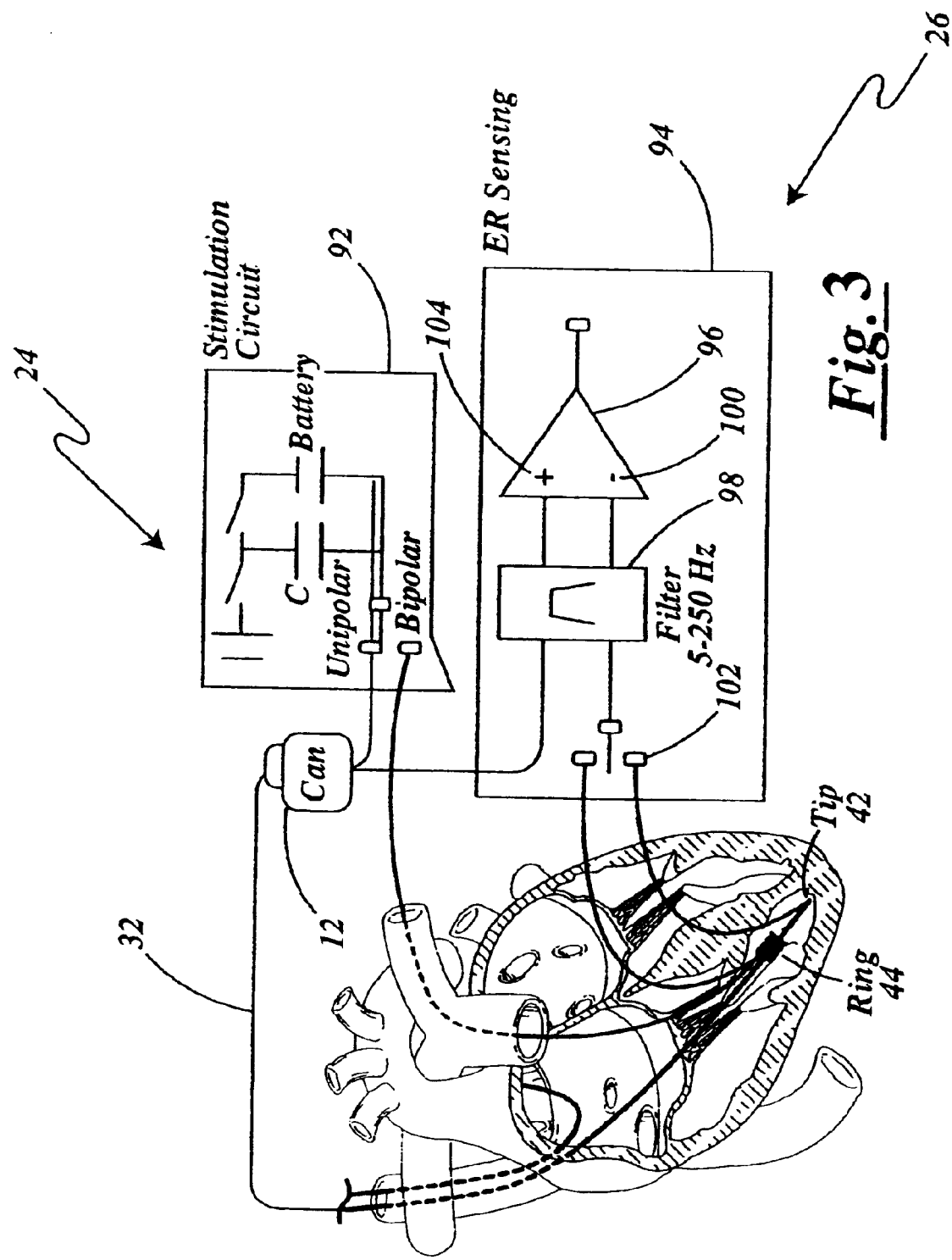
FIG. 3 is a partial sectional view of a lead positioned within the ventricle of a heart and shown electrically coupled to a stimulation and sensing circuit, wherein the stimulation and evoked response (ER) sensing circuits are shown partially in block form and exploded from the housing or can of the cardiac rhythm management device.

Referring now to FIG. 3, another embodiment of the implantable cardiac rhythm management device 10 is shown having a stimulation circuit 24 and evoked response sensing circuit 26, a portion of each of which is shown enclosed by blocks 92 and 94 respectively. As described above, the controller 16 may be in any of several forms including a dedicated state device or a microprocessor with code. The evoked response sensing circuit 26 includes a dedicated sense amplifier 96 and single high pass pole band pass filter 98. The negative terminal or pole 100 of the sense amp 96 is connected via a switch 102 to either electrode 42 or 44. The positive terminal or pole 104 of the sense amplifier 96 is electrically coupled to the electrically conductive housing 12 or indifferent electrode 52 of the cardiac rhythm management device. In this manner, as will be described in greater detail below, the polarity of the amplitude associated with artifact is opposite the polarity of the amplitude associated with evoked response.

Figure 4:
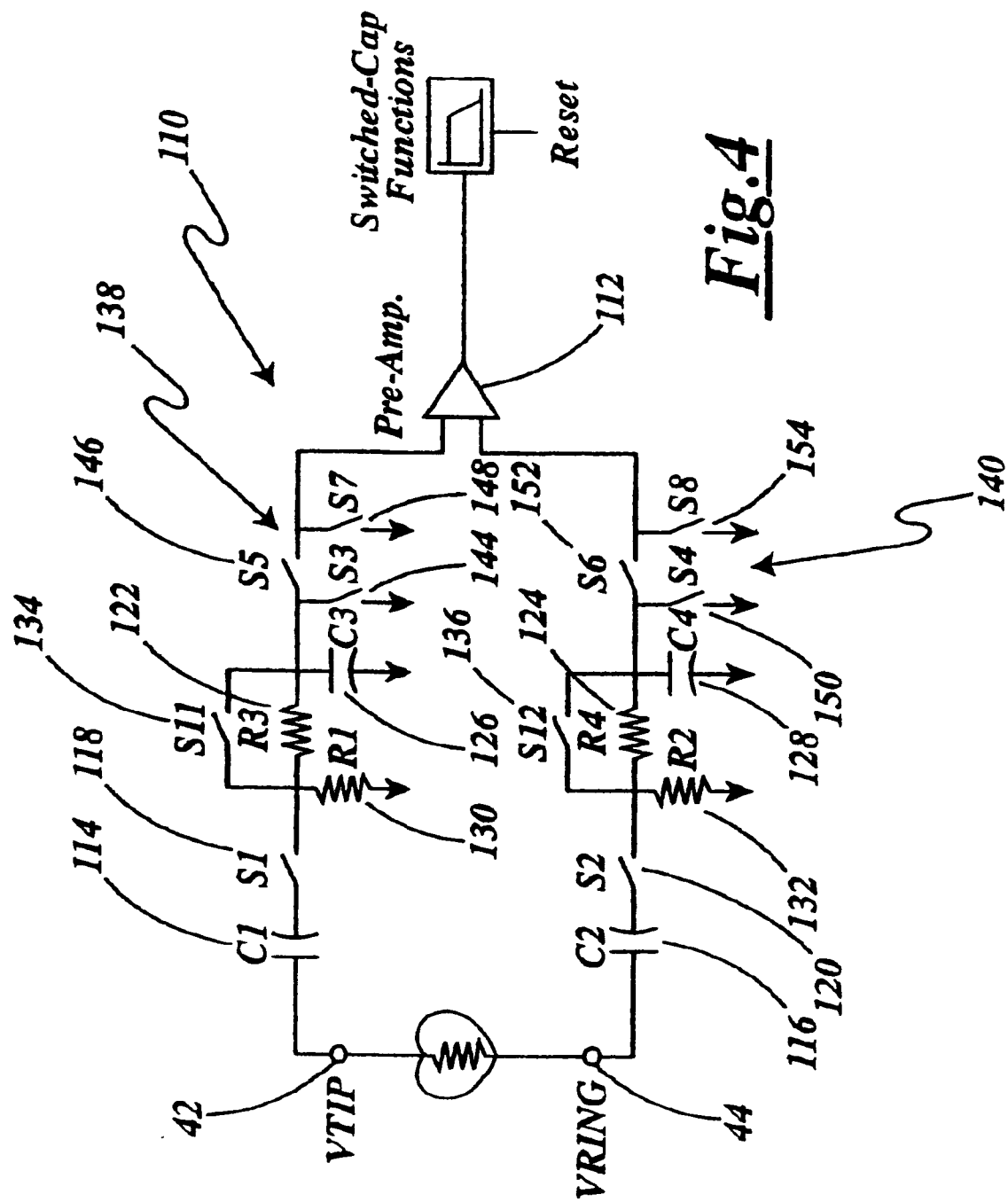
FIG. 4 is a schematic diagram of a portion of a sense amplifier of the present invention.

Referring now to FIG. 4, a portion of a differential sense amplifier 110 suitable for use in the rhythm management device of the present invention is shown in greater detail as having a differential network which offsets imbalances sensed from the electrodes 42 and 44 due to extraneous factors. The differential network sense amplifier 110 generally includes a preamplifier 112, first and second high pass coupling capacitors 114 and 116, and first and second blanking switches 118 and 120 electrically connected together via a plurality of electrical conducting segments of known suitable construction. The first and second high pass coupling capacitors 114 and 116 are electrically coupled between the electrodes, 42 and 44 respectively, and the pre-amplifier 112. Further, the first and second blanking switches 118 and 120 are electrically coupled between the first and second high pass coupling capacitors, 114 and 116 respectively, and the pre-amplifier 112. Electrically coupling the high pass coupling capacitors 114 and 116 between the electrodes 42 and 44 and the blanking switches 118 and 120 reduces the affects of polarization voltages or afterpotentials. Although the sense amplifier having a differential network will be described below, those skilled in the art will appreciate that a single network having a first high pass coupling capacitor 114 electrically connected between the electrode 42 and the first blanking switch 118 reduces pacing artifact and response time of the sensing circuit. High pass termination resistors 28 and 30 may be connected to the circuit with electrical conductor segments between the blanking switches 118 and 120 respectively and the pre-amplifier 112.

Low pass coupling capacitors 126 and 128 and low pass resistors 130 and 132 may be connected via electrical conductor between the blanking switches 118 and 120 respectively and the pre-amplifier 112, wherein low pass bi-pass switches 134 and 136 may be connected via the electrical conducting means segments between the blanking switches 118 and 120 respectively and the pre-amplifier 112 to selectively connect the low pass coupling capacitors 126 and 128 respectively and the low pass resistors 130 and 132 to the electrical circuit. Further, an input blanking member 138 and 140 including without limitations switches 144–148 and 150–154 respectively, may be connected to the electrical conductor between blanking switch 118 and 120 respectively and the pre-amplifier 112 for selectively blanking sensed electrical activity.

Without any limitation intended the first and second high pass coupling capacitors 114 and 116 may have a capacitance of a suitable range with a capacitance of 0.1 microfarads being preferred, the low pass coupling capacitors 126 and 128 may have a capacitance of a suitable range with 3600 picofarads being preferred, and the high and low pass resistors 122, 124, 130, 132, may have a resistance of a suitable range with a resistance of 200 k ohms being preferred.

Figure 5:
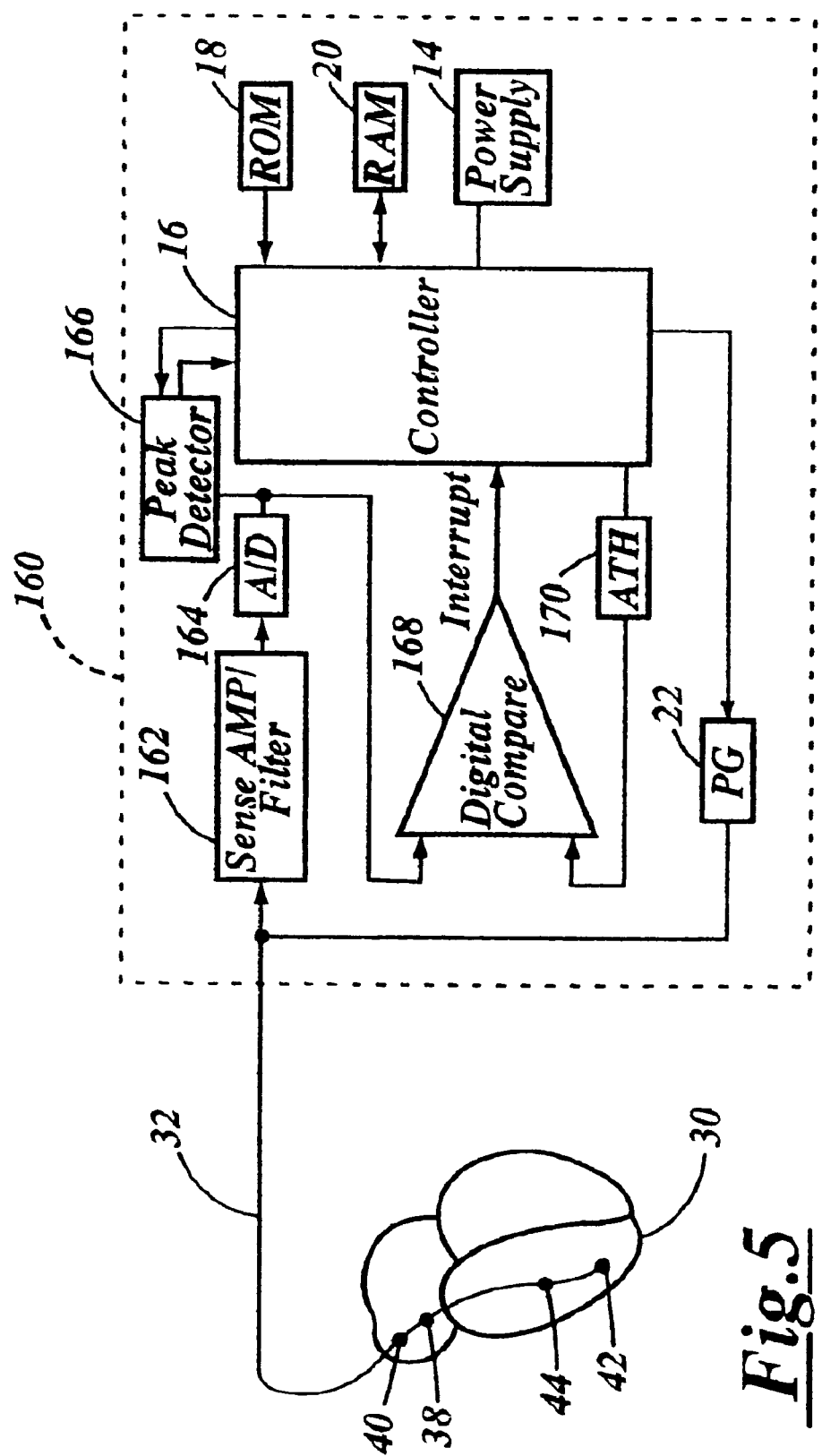
FIG. 5 is a general block diagram of a cardiac rhythm management device that may incorporate the autosense feature of the present invention.

Referring now to FIG. 5, there is illustrated by means of a block diagram, a hardware platform in which the auto-adjust algorithm of the present invention may be utilized. Shown enclosed by the broken line box 160 is circuitry which may be included within a cardiac rhythm management device 10, such as a pacemaker. It is shown to include a sense amplifier/filter 162 having its input connected by a pacing lead 32. The pacing lead 32 is shown having a plurality of electrodes 38–42 coupled to lead 32 and disposed on or in the heart 30. An electrocardiogram signal is transmitted through the pacing lead 32 to the sense amplifier/filter 162.

In FIG. 5, the lead 32 is shown as a bipolar single pass VDD or DDD lead, various forms of which are known to those skilled in the art. Without limitation, the electrodes 42 and 44 are designed to detect ventricular depolarization while electrodes 38 and 40 are utilized to sense atrial depolarization. The controller 16 is coupled to power supply 14 and provides a control output to a pulse generator 22 at appropriate times. The resulting pulses are applied over the lead 32 to the electrodes 38, 40, 42 and/or 44 for providing electrical stimulation to the heart 30. The arrangement shown in FIG. 5 can be used for sensing a response evoked by a pacing pulse in the ventricles.

The sense amp/filter circuit 162 conditions the electrogram signal and then applies the conditioned signal to an analog-to-digital converter 164 which converts the conditioned signal to corresponding digital values compatible with a peak detector 166. From the analog-to-digital converter 164, the signal is transmitted to both peak detector 166 and a comparator 168. Without any limitation intended, the peak detector may include a digital comparator and register, wherein the signal transmitted from the A/D converter 164 is continuously compared with an initial value stored in the peak detector register. If the current signal is greater than the value stored in the peak detector, the current value is loaded into the register value and is then stored in the peak detector register as a "maximum" amplitude. The peak detector 166 includes a clearing mechanism controlled by the controller 16. Those skilled in the art will recognize that the timing circuit 28 utilized to activate and deactivate the peak detector, may be either external or internal to the controller 16. Once the peak detector 166 times out, the final peak detector register value is transmitted to the controller 16. In this manner the peak detector 166 may be utilized to determine the amplitudes of the cardiac depolarization events.

The output from the A/D converter 164 may also be applied as a first input to a digital comparator 168. A second reference input is compared by digital comparator to the first input transmitted from the A/D converter 164. The reference input of the comparator 168 is a digital value stored in the ATH register 170. The controller 16 may periodically compute and modify the digital value stored in the ATH register 170. Without limitation, the reference input of the comparator 168 may correspond to, for example, the evoked response detection/sensing threshold. Of course, other components of suitable known construction are utilized to provide the operable cardiac rhythm management device of the present invention.

The drawing of FIG. 5 shows only one hardware configuration in which the algorithm of the present invention can be implemented. Those skilled in the art will appreciate that the circuit of FIG. 5 can be modified so that, for example, the digital comparator 168 and ATH register 170 can be internal to the controller 16. It is also possible to add an additional digital comparator in parallel with the digital comparator 168 and provide a separate threshold register for corresponding sensing threshold (ST) rather than time sharing the digital comparator 168 between the detection of cardiac depolarization and noise.

Referring to FIGS. 6–8 the current flow of the evoked response and recharge artifact are shown. FIG. 6 shows another embodiment of a sense amplifier 180 electrically coupled to a pacing circuit 182. The negative terminal 184 of the sense amplifier 180 is electrically coupled after the coupling capacitor 186, wherein when switch 188 is closed to start recharge, artifact signals 190 observed due to recharge result in an amplitude having a positive polarity. FIG. 7 shows a dedicated sense amplifier 96 electrically coupled to the pacing circuit 24. The negative terminal 100 of the amplifier 96 is electrically coupled before the coupling capacitor 192. In this manner when a pace pulse captures the heart, the extracellular current flows towards the tip electrode 42 where the activation originated and the evoked response polarity is indicated at 194. The depolarization signal 196 presents to the sense amplifier 96 with the current flow direction reverse to the recharge signal. Thus, a positive polarity of the amplitude associated with evoked response is observed. FIG. 8 shows the sense amplifier 96 capacitively coupled before the coupling capacitor 192. When switch 188 closes, the signals 198 observed due to recharge result in an amplitude having a negative polarity.

Figure 9:
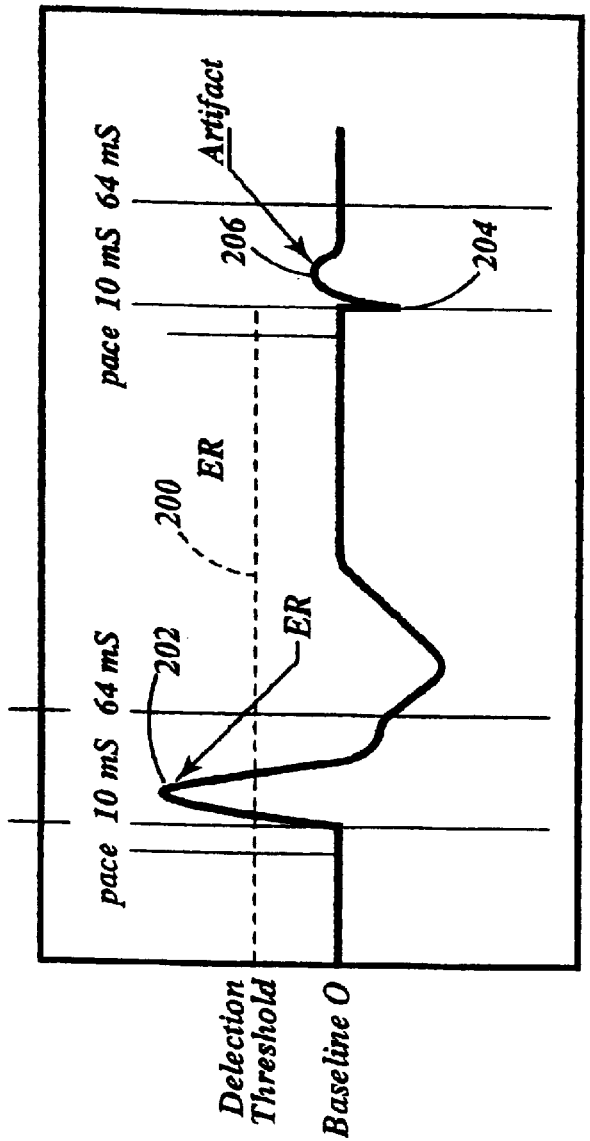
FIG. 9 is a graph of an electrocardiogram signal sensed over time with the sensing circuit of the present invention.

Referring now to FIG. 9 an expected electrocardiogram signal is shown resulting from a pacing stimulus delivered from a rhythm management device of the present invention. Without limitation, the dedicated evoked response sense amplifier is duty cycled and is only turned on by the controller during a predefined capture detection window. The capture detection window shown in FIG. 9 is defined by the time from pacing to 64 msec after pace. Those skilled in the art will appreciate that the capture detection window may be defined either longer or shorter than the period shown in FIG. 9. The evoked response detection threshold is shown by dotted line 200, wherein a positive peak amplitude 202 associated with the evoked response exceeds the evoked response detection threshold 200. Later in time, the artifact associated with recharge is seen having primarily a negative peak amplitude 204. The minor portion 206 of the signal associated with artifact does not exceed the evoked response detection threshold and does not result in false capture declaration.

Figure 10:
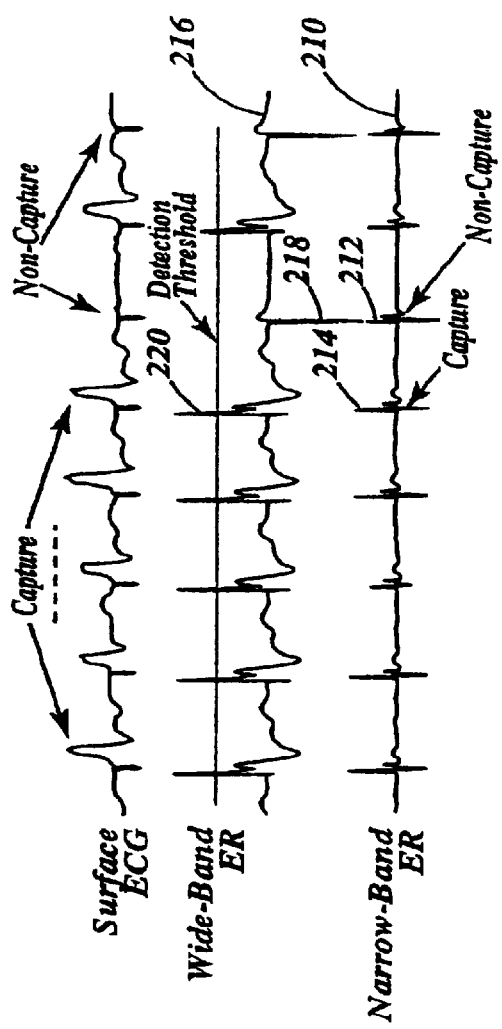
FIG. 10 is a graph showing for comparison a surface electrocardiogram signal, an electrocardiogram signal processed with a single high pass pole band pass filter and an electrocardiogram signal processed with a band pass filter having multiple high pass poles, wherein the representative signals were observed over the same period of time.

FIG. 10 further shows the advantage of utilizing a single high pass pole band pass filter in conjunction with a dedicated evoked response sense amplifier. A typical signal processed through a narrow-band filter (10–100 Hz) results in a signal 210 having amplitudes associated with evoked response and/or artifact that are difficult to distinguish. For example, the portion of the narrow-band signal identified as non-capture 212 has a positive polarity that is nearly as large as the prior positive polarity of the portion 214 corresponding to capture. Thus, it is difficult to distinguish the evoked response and artifact of a signal processed through a narrow-band filter. In contrast, the same detected signal processed through a single high pass pole band pass filter results in a signal 216, wherein a portion of the signal 218 associated with artifact has an amplitude having a negative polarity, whereas a portion of the signal 220 associated with evoked response has an amplitude having a positive polarity. Thus, the capture verification circuit of the present invention having a dedicated evoked response sense amplifier electrically coupled in a manner wherein a polarity of an amplitude of a sensed signal corresponding to an evoked response is opposite a polarity of an amplitude of the sensed signal corresponding to afterpotential is particularly useful in verifying capture.

Figure 11:
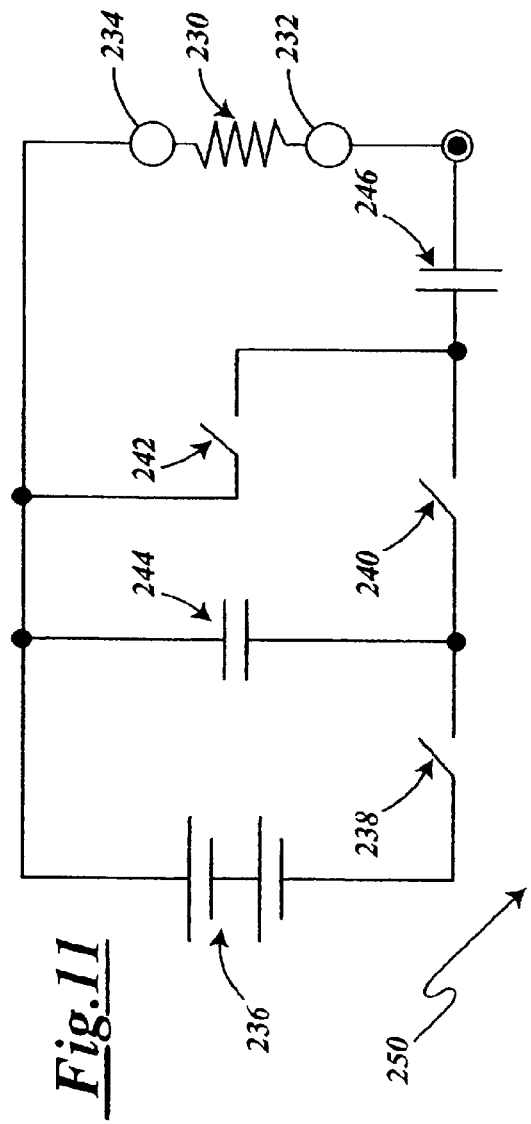
FIG. 11 is a schematic diagram of a conventional pacing output circuit.

FIG. 11 is a circuit diagram illustrating a conventional pacing output circuit having the specific components identified below and found in any of a variety of prior art pacemakers. The pacing output circuit is designed to selectively generate and deliver stimulus pulses to the heart of a patient, indicated schematically as the resistive load 230, via a tip electrode 232 and ring electrode 234. The circuit includes a power supply or battery 236, a first switch 238, a second switch 240, a third switch 242, a pacing charge storage capacitor 244 generally having a capacitance of between 10–30 microfarads, and a coupling capacitor 246 generally having a capacitance greater than 10 microfarads, all of which cooperatively operate under the direction of a microprocessor-based controller (not shown) to perform a charging cycle, a pacing cycle, and a recharging cycle. The charging cycle involves having the first switch 238 closed and the second and third switches 240, 242 open such that the pacing charge storage capacitor 244 is charged up to a predetermined voltage level. The pacing cycle involves having the first and third switches 238, 242 open and the second switch 240 closed such that the voltage within the pacing charge storage capacitor 244 may be discharged through the coupling capacitor 246 to the tip electrode 232 of the pacemaker. Immediately after pacing, the second and third switches 240, 242 are in the open state such that charges within the coupling capacitor 246 will decay slowly through leakage. The recharging cycle involves having the first and second switches 238 and 240 open and the third switch 242 closed for a predetermined period of time following the pacing pulse to allow the coupling capacitor 246 to be discharged through the load 230.

While the foregoing conventional pacing circuit is generally effective in delivering stimulus pulses to the heart 30, it has been found that the detection of evoked depolarization or capture verification is rendered very difficult due to polarization voltages or "afterpotentials" which develop at the heart tissue/electrode interface following the application of the stimulation pulses. The inventors of the present invention have discovered that these polarization voltages are due, in large part, to the relatively large capacitance (e.g. 33 microfarads) of the coupling capacitor 246. The large capacitance of coupling capacitor 246 was believed necessary to deliver sufficient energy to the heart. However, the large capacitance of the coupling capacitor 246 also causes a charge dissipation or "afterpotential" which is relatively large (100 millivolts or greater) and which decays exponentially over a relatively long period of time (100 milliseconds). This is particularly troublesome due to the fact that the evoked potential or R-wave of the heart tissue is small in amplitude (5–20 millivolts) relative to the polarization voltage or "afterpotential" (100 millivolts). Moreover, the long decay period of the polarization voltage or "afterpotential" effectively masks the evoked response, which typically begins within approximately 10–20 milliseconds after the stimulation pulse. It will be appreciated that this creates difficulty in detecting the evoked response of the heart following the delivery of stimulus pulses. In that evoked response is indicative of capture, the undesirable masking of the evoked response by "afterpotentials" thus hampers the ability of the pacemaker to conduct automatic capture verification.

Figure 12:
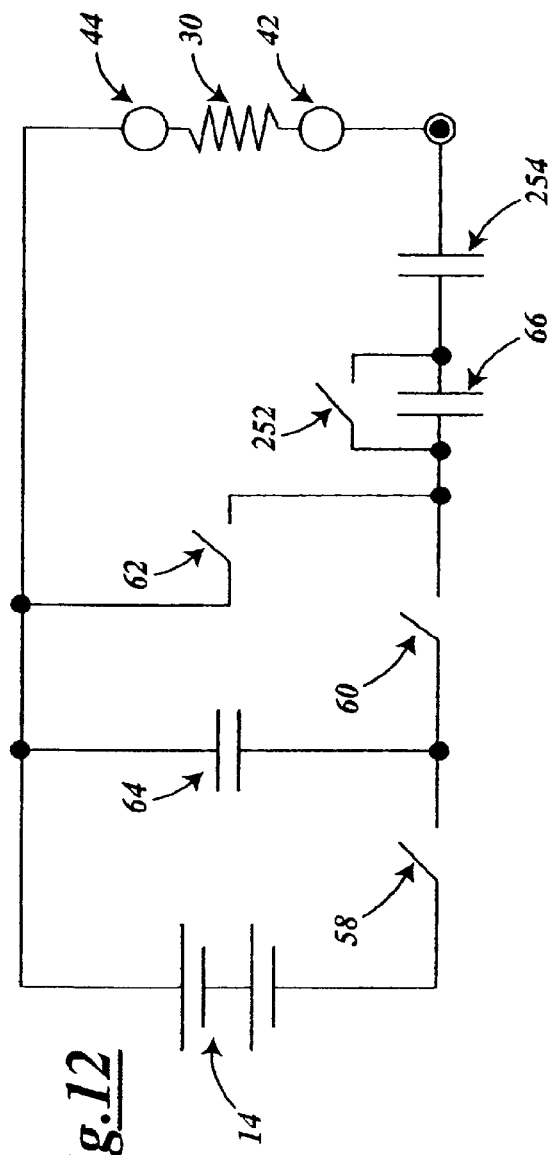
FIG. 12 is a schematic diagram of a pacing output circuit provided in accordance with a preferred embodiment of the present invention.

With reference to FIG. 12, another embodiment of the present invention includes an improved pacing output circuit 250 for delivery of stimulation pulses with reduced affects of afterpotential. As will be explained below, the improved pacing output circuit 250 is capable of quickly attenuating polarization voltages or "afterpotentials" which result due to the application of stimulus pulses to the heart 30. By attenuating the polarization voltages or "afterpotentials" in this fashion, the improved pacing circuit 250 of the present invention facilitates the task of capture verification in that the presence or absence of evoked responses may be readily determined without the masking caused by afterpotentials. Capture verification may advantageously allow the rhythm management device 10 to automatically adjust the capture threshold so as to minimize power consumption while assuring therapeutic efficacy.

In a preferred embodiment, the improved pacing output circuit 250 of the present invention includes a power supply or battery 14, a first switch 58, a second switch 60, a third switch 62, a fourth switch 252, a pacing charge storage capacitor 64, a first coupling capacitor 66, and a second coupling capacitor 254, all of which are cooperatively operable under the direction of the controller 16. By way of example, the improved pacing output circuit 250 is illustrated in a ventricular pacing arrangement for delivering stimulus pulses to the heart or resistor 30 via the tip electrode 42 and ring electrode 44 of the lead 32.

It is to be readily understood, however, that the improved pacing output circuit 250 of the present invention may also find application in an atrial pacing arrangement. The power supply or battery 14 is preferably the battery provided to power the rhythm management device 10 and may comprise any number of commercially available batteries suitable for pacing applications. The switches 58–62 and 252 are illustrated as discrete components but are preferably carried out via any number of commercially available microprocessor-directed semiconductor integrated circuit switching means. The pacing charge storage capacitor 64 may also comprise any number of commercially available storage capacitors, but is preferably provided with a capacitance in the range greater than 10 microfarads so as to develop a sufficient pacing charge for stimulating the heart 30.

One function of the second coupling capacitor 254 is to block DC signals from reaching the heart 30 during pacing. In order to minimize the pacing pulse droop the second coupling capacitor 254 should have a sufficiently large capacitance, for example, greater than 10 microfarads. In an important aspect of the present invention, the first coupling capacitor 66 is advantageously provided having a capacitance preferably less than 5 microfarads and substantially smaller than that of the second coupling capacitor 254. The first coupling capacitor 66 may be selectively operable, via the fourth switch 252, so as to selectively reduce the effective capacitance of the second coupling capacitor 254, thereby quickly attenuating the polarization voltage or "afterpotentials" which result from pacing.

Referring next to FIGS. 13 and 14, the respective expected resulting pacing waveforms 260 and 262 observed between the tip and ring of a lead, for the conventional pacing circuit (FIG. 13) and the stimulation circuit of the present invention (FIG. 14), are shown for comparison. By electrical analysis theory, familiar to those skilled in the art, the pacing afterpotential signal decay characteristics are determined by the time constant formed by the product of the coupling capacitor (blocking) and the load (a combination of the impedance of the lead body, electrode/tissue interface, and myocardium). When the capacitance of the coupling capacitor is reduced, the afterpotential has a larger initial amplitude but dissipates faster (compare afterpotential amplitudes 264 and 266 for the respective pacing afterpotential waveforms 260 and 262). The blanking period 268 before sensing for the conventional capacitor is greater than the required blanking period 270 when utilizing a 1 microfarad coupling capacitor (see FIGS. 13 and 14 for comparison). Also, the recharge time 272 when utilizing the conventional coupling capacitor is significantly longer than the required recharge time 274 required for the 1 microfarad capacitor. Further, the recharge time 272 overlaps into sensing period 276 for the conventional capacitor, whereas the recharge time 274 terminates prior to the beginning of the sensing period 278 for the 1 microfarad capacitor. Hence, when the coupling capacitance is sufficiently small, for example, less than 5 microfarads, the pacing afterpotential will settle to baseline at a faster rate and before the onset of the evoked response, thereby making detection of the evoked response feasible.

Those skilled in the art will appreciate that as the coupling capacitance decreases, the pacing pulse seen by the heart will bear a larger droop and the threshold voltage that evokes a response increases. Thus, if a small coupling capacitance is utilized during a determination of the threshold, the determined threshold will be greater than the actual threshold required during normal pacing (assuming that a conventional coupling capacitance is utilized during normal pacing), thereby increasing the pacing safety margin. It is believed by the inventors that use of a coupling capacitor having a capacitance in the range of 2 microfarads will not significantly increase the pacing threshold or output threshold, with the required increase being under ten percent. The increase in output threshold becomes a greater significance when the coupling capacitance is set below 1 microfarad.

Referring next to FIGS. 15 and 16, the sensed signals 280 and 282 observed from the electrodes of a pacing lead utilizing a conventional pacing circuit and the pacing circuit of the present invention respectively, are shown for comparison. FIG. 15 shows a recorded signal 280 received when implementing a 15 microfarad coupling capacitor having a recharge time of 30 milliseconds and a blanking of 15 milliseconds. Those skilled in the art will appreciate that the intracardiac signal 280 is overwhelmed with pacing afterpotential and, thus, the evoked response 284 and non-captured artifacts 286 during capture and non-capture respectively are not easily distinguishable within 100 milliseconds after pacing. FIG. 16 shows a recorded signal 282 received when implementing a 1 microfarad coupling capacitor having a 10 millisecond recharge time and a blanking time of 12 milliseconds. The evoked response 288 and non-captured artifacts 290 are readily distinguishable during capture and non-capture for the signal 282. Without limitation, a conventional peak detector utilized for intrinsic sensing may be adapted for detecting the peaks in the signal 282 received after pacing while using a 1 microfarad coupling capacitor having a 10 millisecond recharge time. The high-low-high pacing output scheme in both FIGS. 15 and 16 was implemented to ensure that capture would result from at least half of all the pacing stimulus.

Referring now to FIG. 17 a suitable electrical coupling between the stimulation circuit, sensing circuit and electrodes is shown. An atrial intrinsic sense amplifier 294 electrically coupled between the atrial ring 40 and atrial tip 38. The ventricular intrinsic sense amplifier 296 is electrically coupled between the ventricular ring electrode 44 and the ventricular tip electrode 42. A separate evoked response sense amplifier 298 is shown electrically coupled to a multi-switch 300, wherein the evoked response sense amplifier 298 may be electrically coupled to sense evoked response waveforms resulting from either an atrial pacing stimulus or ventricular pacing stimulus with any of the following sensing configurations: atrial ring to indifferent, atrial ring to ventricular tip, atrial ring to ventricular ring, atrial tip to ventricular ring, atrial tip to ventricular tip, atrial tip to indifference, ventricular ring to indifference, ventricular tip to indifference, and ventricular ring to ventricular tip. Those skilled in the art will appreciate that the preferred sensing configuration utilizing the separate evoked response sense amplifier 298 will vary depending upon whether the pacing stimulus is unipolar or bipolar and whether the pacing stimulus is directed in the atrium or ventricle. When unipolar pacing in the ventricle, the ventricular evoked response is preferably sensed between the ventricular ring to atrial tip electrodes, and alternatively, without limitation, may be sensed between the ventricular ring to indifferent, atrial tip to indifferent, or atrial ring to indifferent electrodes. When bipolar pacing in the ventricle, the ventricular evoked response is preferably sensed between the atrial tip and the conductive housing or can of the cardiac pacer, and alternatively, without limitation, may be sensed between the atrial tip to indifferent, atrial ring to can or atrial ring to indifferent electrodes. When unipolar pacing in the atrium, the atrial evoked response is preferably sensed between the atrial ring to indifferent and alternatively, without limitation, may be sensed between the atrial ring to ventricular tip, ventricular ring to indifferent, or ventricular tip to indifferent electrodes. When bipolar pacing in the atrium, the atrial evoked response is preferably sensed between the ventricular ring to can, and alternatively without limitation may be sensed between the ventricular ring to indifferent, ventricular tip to can, or ventricular tip to indifferent electrodes.

Figure 20:
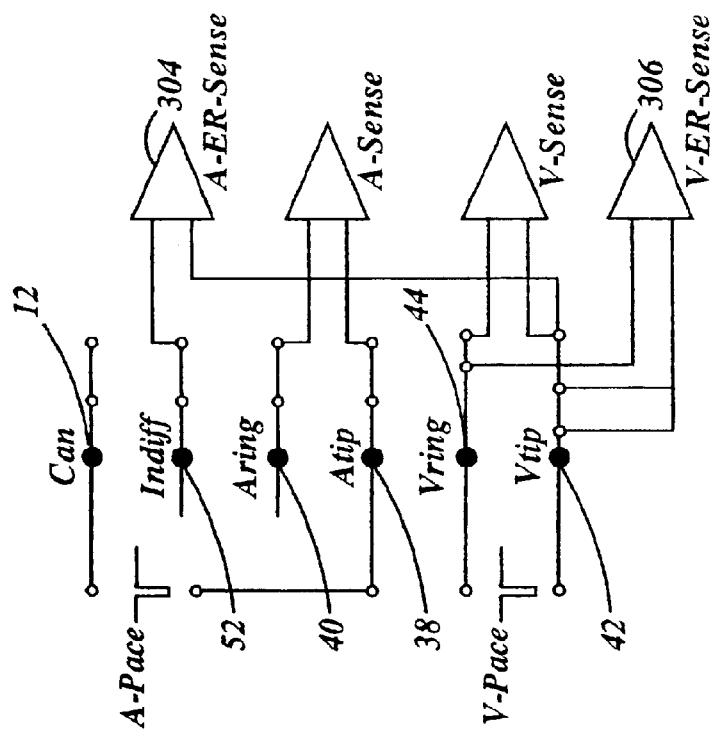
FIG. 20 is a schematic diagram of an alternate embodiment of a portion of the pacing/sensing circuitry in accordance with the present invention.
Figure 19:
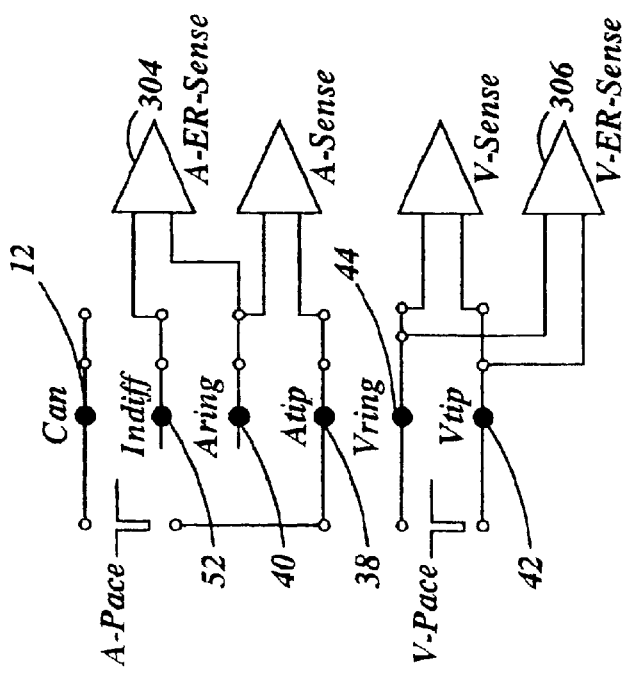
FIG. 19 is a schematic diagram of an alternate embodiment of a portion of the pacing/sensing circuitry in accordance with the present invention.

Referring now to FIGS. 18–20 other alternate embodiments of the electrical coupling between the stimulation circuit, sensing circuit and electrodes are shown. FIG. 18 shows a dedicated atrial ventricular evoked response sense amplifier 302 electrically coupled between the atrial ring electrode 40 and the ventricular tip electrode 42. FIG. 19 shows yet another alternate embodiment wherein a dedicated atrial evoked response amplifier 304 is electrically coupled between the atrial ring electrode 40 and the indifferent electrode 52 and a dedicated ventricular evoked response amplifier 306 is electrically coupled between the ventricular ring electrode 44 and the ventricular tip electrode 42. FIG. 20 shows still another alternate embodiment, wherein the dedicated atrial evoked response amplifier 304 is electrically coupled between the indifferent electrode 52 and the ventricular tip electrode 42 and a dedicated ventricular evoked response amplifier 306 is electrically coupled between the ventricular ring electrode 44 and the ventricular tip electrode 42.

Figure 22:
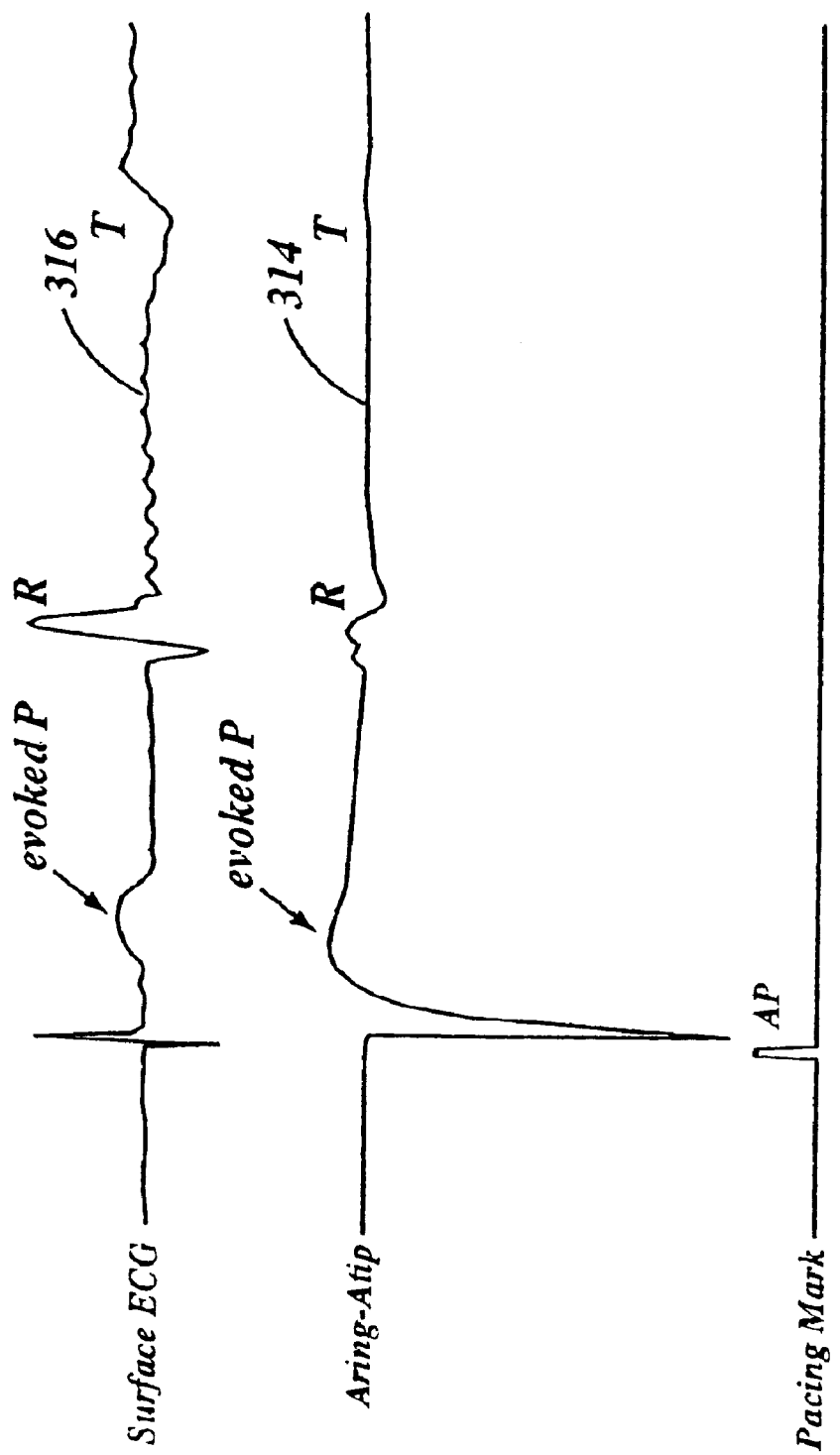
FIG. 22 depicts waveforms resulting from an atrial pacing output or stimulus, wherein the first waveform is sensed with the atrial ring electrode and atrial tip electrode of the atrial pacing lead and a second waveform shown for comparison is sensed with a surface ECG, while utilizing a conventional coupling capacitor, and wherein the pacing output is above the required threshold output.

Referring next to FIGS. 21 and 22, a recorded signal sensed between the atrial tip electrode 38 and the atrial ring electrode 40 resulting from a paced stimulus between the atrial tip electrode 38 and the atrial ring electrode 40 is shown, wherein a conventional coupling capacitor was utilized in the pacing and sensing circuits 24 and 26 respectively. FIG. 21 illustrates a resulting output or signal 310 and corresponding surface electrocardiogram (ECG) signal 312, wherein the pacing output voltage is below the known threshold. FIG. 22 illustrates a resulting signal 314 and corresponding ECG signal 316, wherein the pacing output voltage is above the known threshold. Those skilled in the art will appreciate that the intra cardiac signals 310 and 314 are overwhelmed with pacing afterpotential and, thus, the evoked response and non-captured artifacts during capture and non-capture respectively are not easily distinguishable within 100 milliseconds after pacing.

Figure 23:
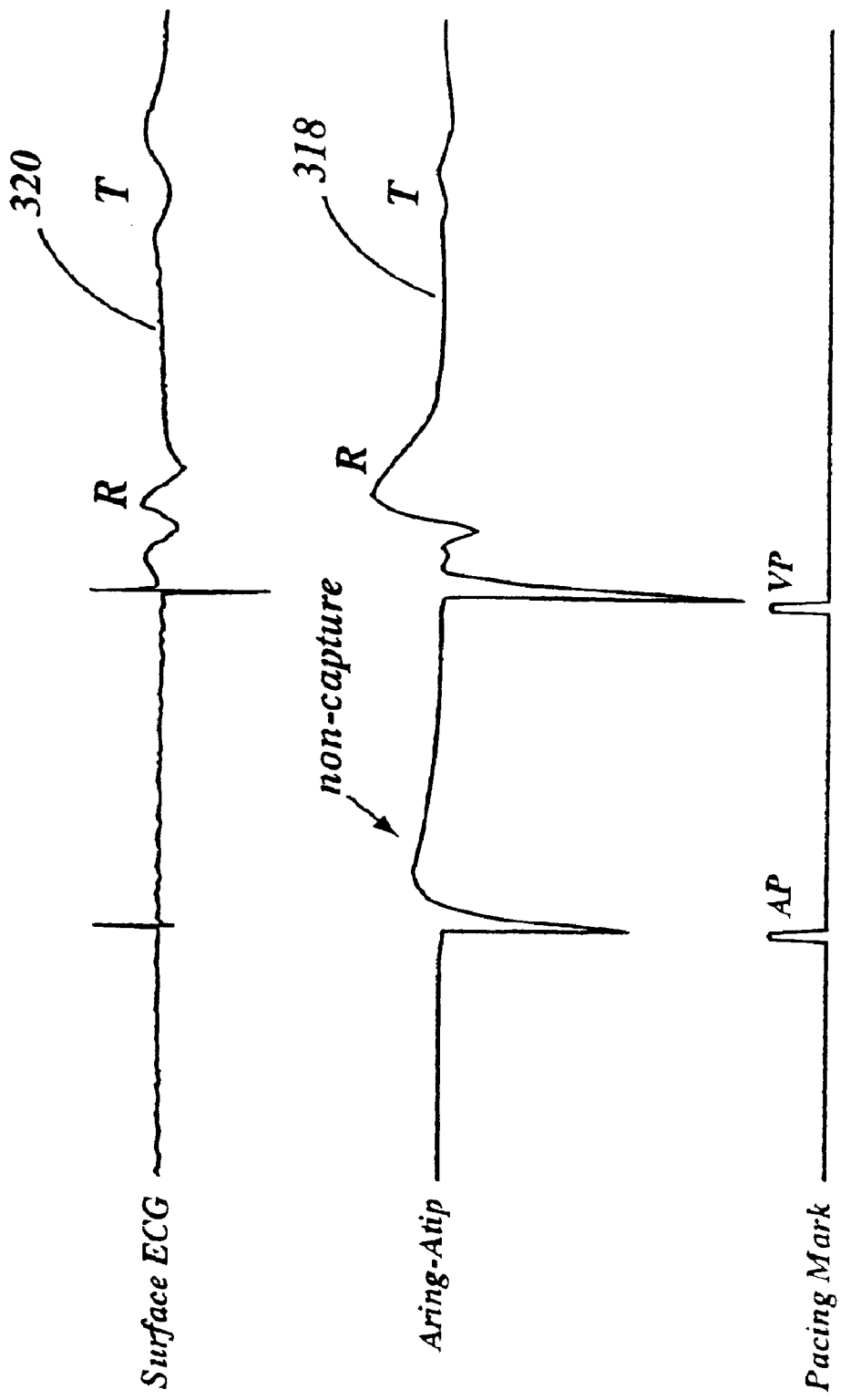
FIG. 23 depicts waveforms resulting from an atrial pacing output and a later ventricular pacing output, wherein the first waveform is sensed with the atrial ring electrode and atrial tip electrode of the atrial pacing lead and a second waveform shown for comparison is sensed with a surface ECG, while utilizing the afterpotential attenuation means of the present invention, and wherein the pacing output is below the required threshold output.
Figure 24:
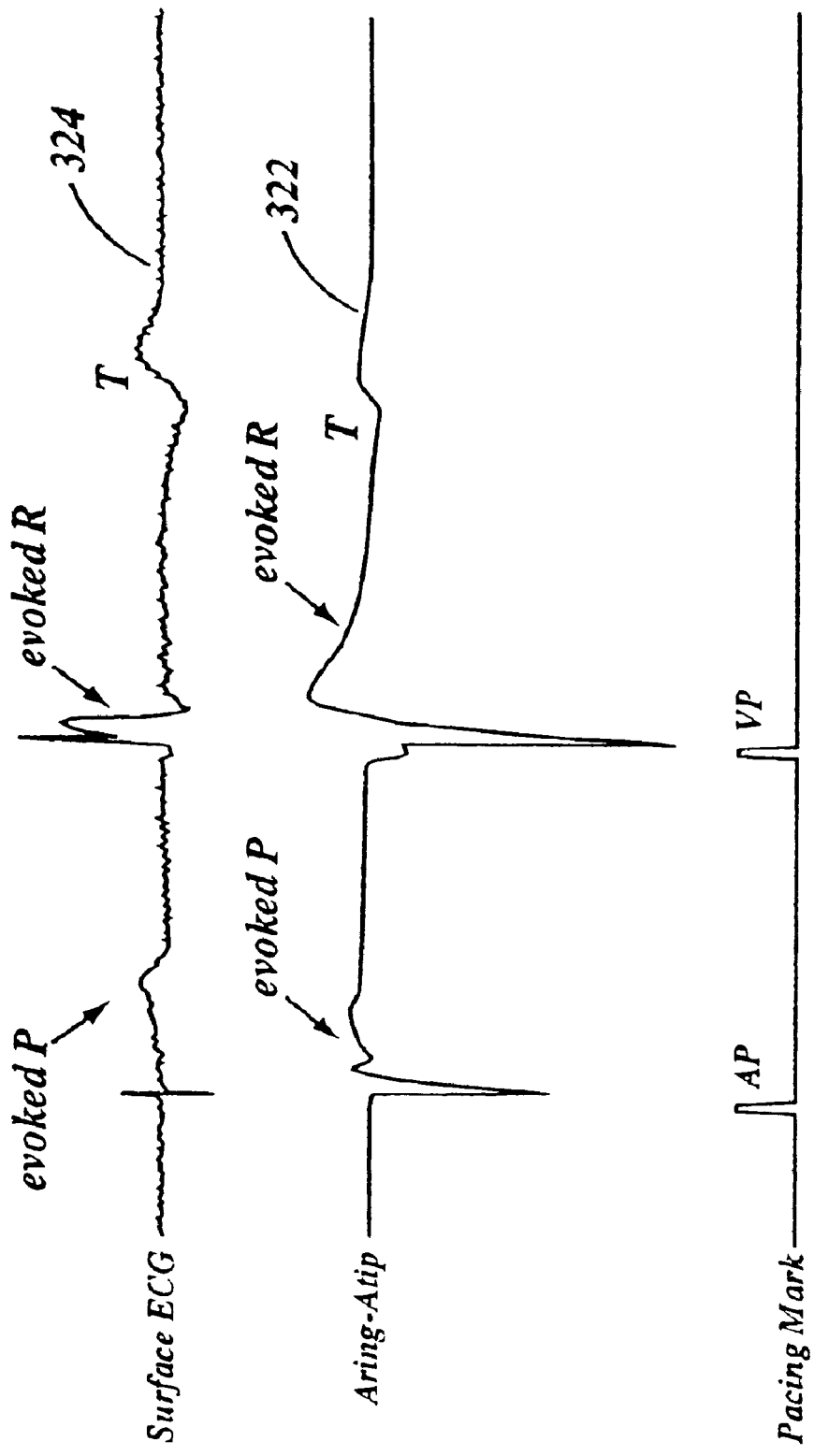
FIG. 24 depicts waveforms resulting from an atrial pacing output and a later ventricular pacing output, wherein the first waveform is sensed with the atrial ring electrode and atrial tip electrode of the atrial pacing lead and a second waveform shown for comparison is sensed with a surface ECG, while utilizing an afterpotential attenuation means of the present invention, and wherein the pacing output is above the required threshold output.

FIGS. 23 and 24 show recorded signals sensed between the atrial tip electrode 38 and the atrial ring electrode 40 resulting from a paced stimulus between the atrial tip electrode 38 and the atrial ring electrode 40 received when implementing a 2 microfarad coupling capacitor having an 8 millisecond recharge time and a blanking time of 10 milliseconds. FIG. 23 illustrates a resulting output or signal 318 and corresponding surface electrocardiogram (ECG) signal 320, wherein the pacing output voltage is below the known threshold. FIG. 24 illustrates a resulting signal 322 and corresponding ECG signal 324, wherein the pacing output voltage is above the known threshold. The evoked response and non-captured artifacts are readily distinguishable during capture and non-capture for signals 318 and 322. Without limitation, a conventional peak detector may be adapted for detecting the peaks in the recorded signal received after pacing while using a 1 microfarad coupling capacitor having a 8 millisecond recharge time.

Figure 25:
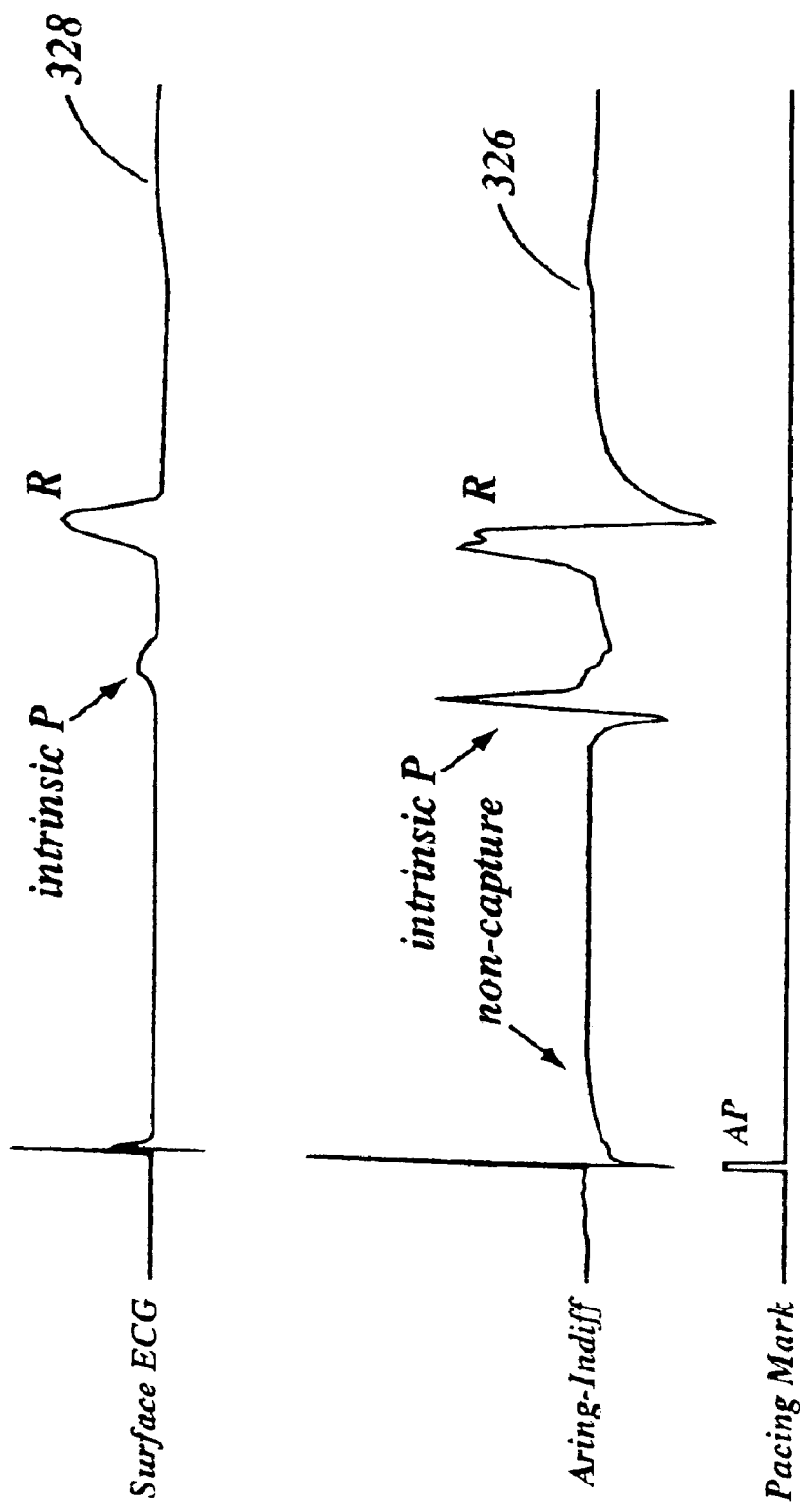
FIG. 25 depicts waveforms resulting from an atrial pacing output, wherein the first waveform is sensed with the atrial ring electrode and an indifferent electrode, and a second waveform shown for comparison is sensed with a surface ECG, while utilizing the afterpotential attenuation means of the present invention, and wherein the pacing output is below the required threshold output.
Figure 26:
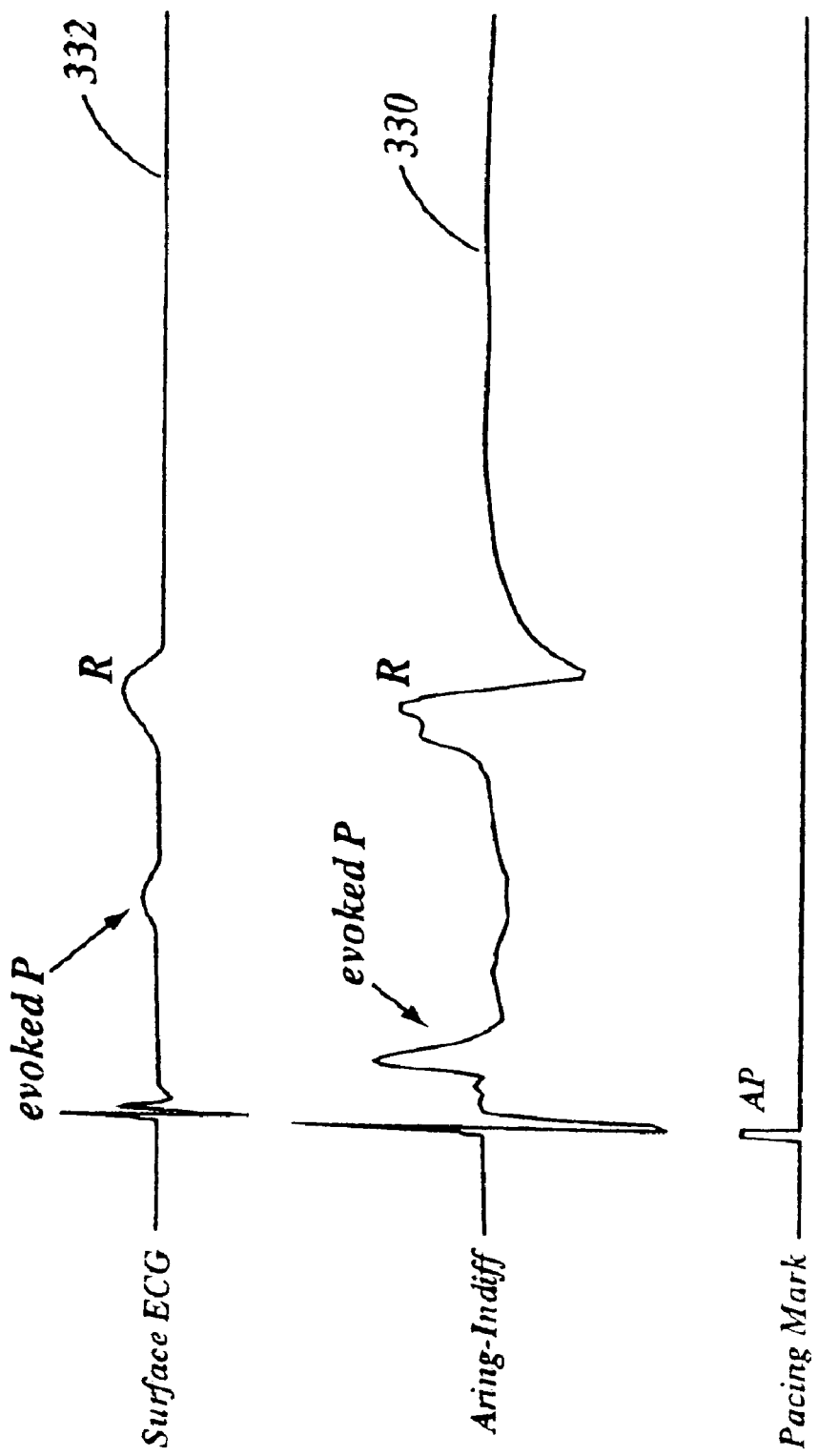
FIG. 26 depicts waveforms resulting from an atrial pacing output, wherein the first waveform is sensed with the atrial ring electrode and an indifferent electrode, and a second waveform shown for comparison is sensed with a surface ECG, while utilizing the afterpotential attenuation means of the present invention, and wherein the pacing output is above the required threshold output.

FIGS. 25 and 26 show recorded signals sensed between the atrial ring electrode 40 and the indifferent electrode 52 resulting from a paced stimulus between the atrial ring electrode 40 and the can 52. The recorded signals were received while implementing a 2 microfarad coupling capacitor having a 10 millisecond recharge time and a blanking time of 12 milliseconds. FIG. 25 illustrates a resulting output or signal 326 and corresponding surface electrocardiogram (ECG) signal 328, wherein the pacing output is below the known threshold. FIG. 26 illustrates a resulting signal 330 and corresponding ECG signal 332, wherein the pacing output voltage is above the known threshold. The evoked response and non-captured artifacts are readily distinguishable during capture and non-capture for signals 326 and 330. As best seen in FIG. 26, the evoked response is readily distinguishable from output associated with polarization.

Figure 27:
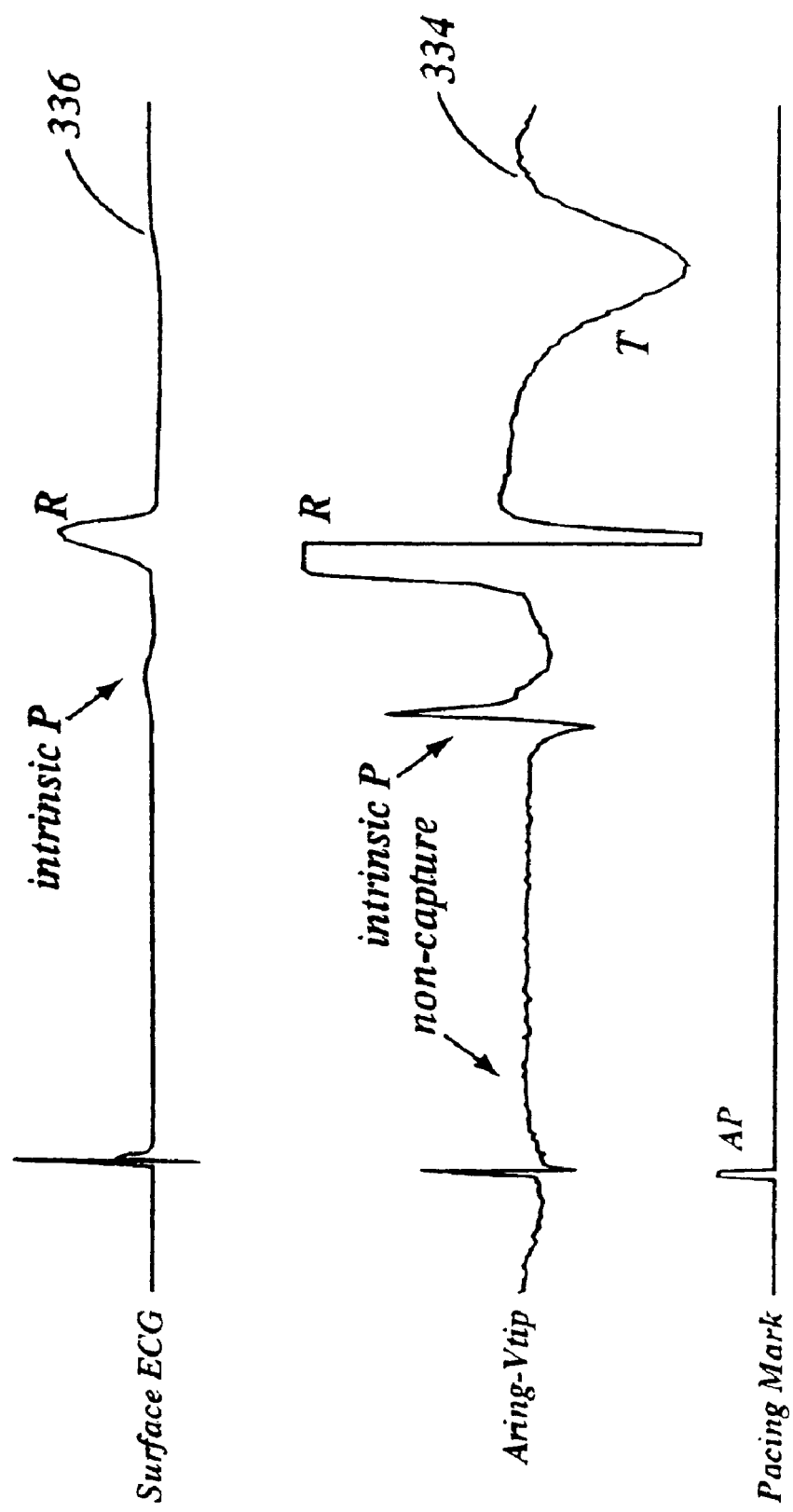
FIG. 27 depicts waveforms resulting from an atrial pacing output, wherein the first waveform is sensed with the atrial ring electrode and ventricular tip electrode, and a second waveform shown for comparison is sensed with a surface ECG, while utilizing the afterpotential attenuation means of the present invention, and wherein the pacing output is below the required threshold output.
Figure 28:
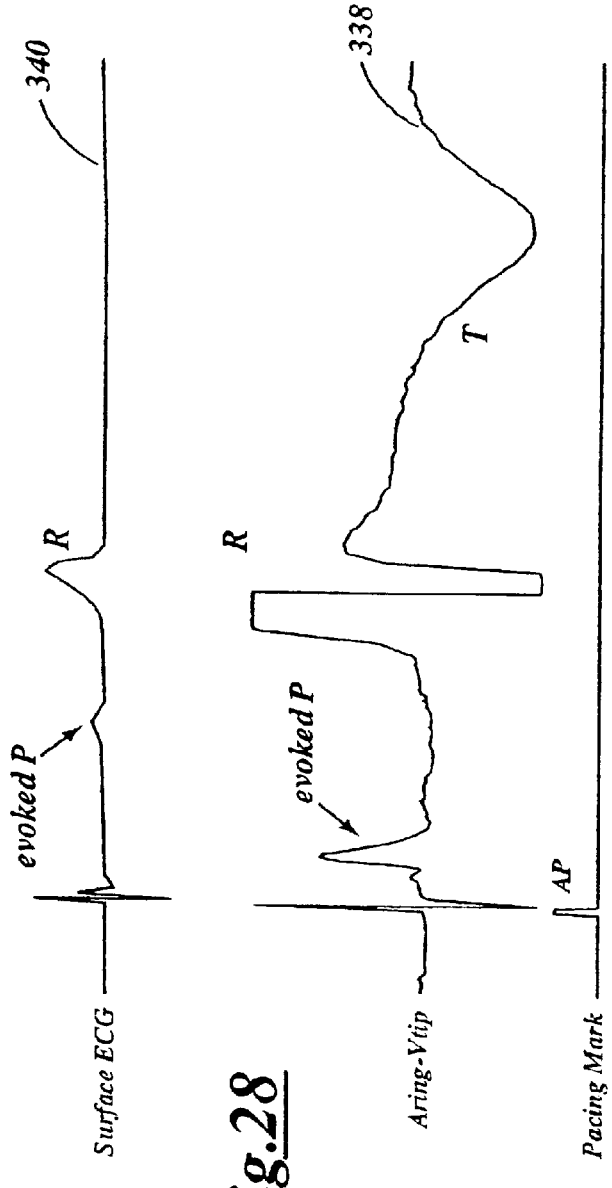
FIG. 28 depicts waveforms resulting from an atrial pacing output, wherein the first waveform is sensed with the atrial ring electrode and ventricular tip electrode, and a second waveform shown for comparison is sensed with a surface ECG, while utilizing the afterpotential attenuation means of the present invention, and wherein the pacing output is above the required threshold output.

FIGS. 27 and 28 show recorded signals sensed between the atrial ring electrode 40 and the ventricular tip electrode 42 resulting from a paced stimulus between the atrial ring electrode 40 and the can 52. The recorded signals were received while implementing a 2 microfarad coupling capacitor having a 10 millisecond recharge time and a blanking time of 12 milliseconds. FIG. 27 illustrates a resulting output or signal 334 and corresponding surface electrocardiogram (ECG) signal 336, wherein the pacing output voltage is below the known threshold. FIG. 28 illustrates a resulting signal 338 and corresponding ECG signal 340, wherein the pacing output voltage is above the known threshold. The evoked response and non-captured artifacts are readily distinguishable during capture and non-capture for signals 334 and 338. Those skilled in the art will appreciate that noise is less likely to affect the recorded signal sensed between the atrial ring electrode 40 and ventricular tip electrode 42 and further the sensing configuration may also be utilized to detect a ventricular evoked response.

Figure 29:
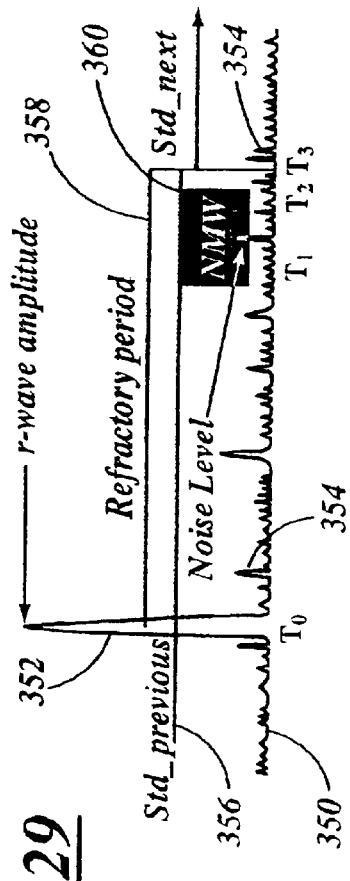
FIG. 29 is a graph of a filtered electrocardiogram signal showing a noise measurement window implemented for ventricular autosense.

Referring next to FIG. 29, there is shown an electrogram signal as it relates to an implantable cardiac rhythm management device set in a ventricular autosense mode and incorporating the improvements of the present invention. The electrocardiogram signal represented by the waveform 350 includes a cardiac depolarization or r-wave deflection 352 and numerous noise deflections 354. The ventricular autosense mode is shown including a sensing threshold which is represented by line 356 and a refractory period represented by line 358. The sensing threshold 356 may be implemented to effectively block out sensing by the controller 16 all deflections in the waveform 350 that do not have an amplitude value greater than the preset sensing threshold value. As previously mentioned, a comparator may be utilized to block out all deflections that do not have an amplitude that exceeds the sensing threshold value, for example, 0.25 mV.

During ventricular autosense, once a cardiac depolarization is detected at $t_0$, a refractory period is initiated and the sensing threshold 356 is reduced for a period of time ($t_2-t_1$), shown as the noise measurement window (NMW) 360 during the refractory period 358, such that the maximum amplitude of noise may be detected and measured. In the preferred embodiment, the NMW ends at least 10 ms prior to the end of the refractory period ($t_3-t_2$), thereby reducing the likelihood that a premature ventricular contraction (PVC) will be confused as noise.

Figure 30:
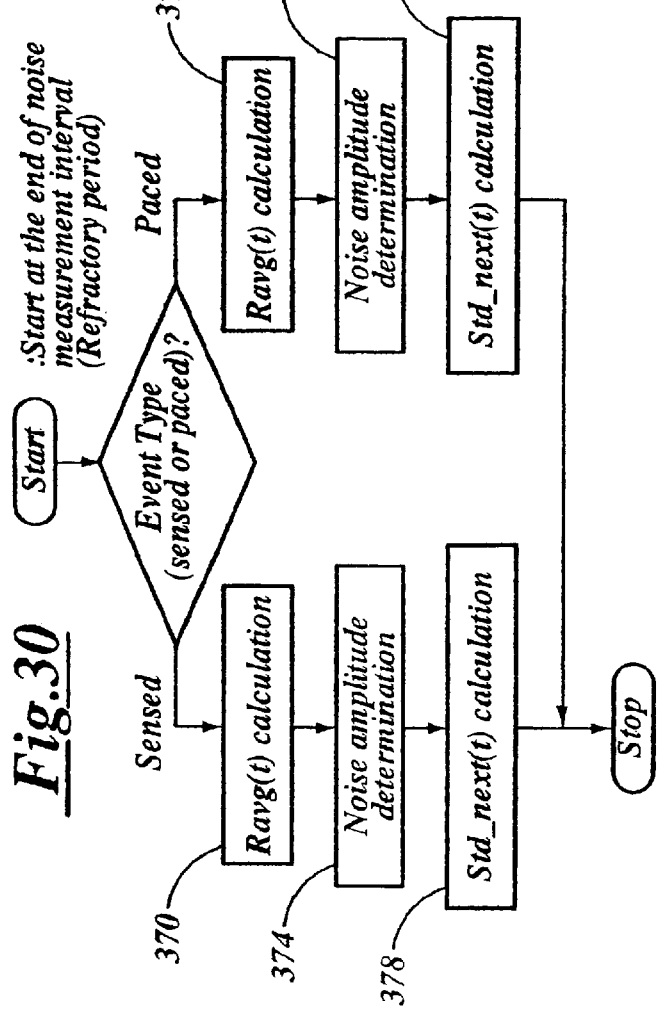
FIG. 30 is a software flow diagram of the autosense algorithm of the present invention following the measurement of noise for ventricular autosense.

Embodied in the controller 16 is a timing circuit 28 and deflection counter capable of measuring the number of deflections having an amplitude that exceeds the sensing threshold during each predetermined period. When the timer times out for each refractory period, the sensing threshold 356 value is adjusted by the controller 16 as a function of the measured noise and intrinsic beat. FIG. 30 shows an algorithm in flowchart form that may be implemented by the controller 16 to adjust the sensing threshold as a function of noise and intrinsic beat during ventricular autosense. This algorithm is executed by a dedicated portion of controller 16.

Without any limitation intended, when an electrocardiogram excursion picked up on lead 32 is signal processed by the sense amplifier/filter circuit and converted to a digital quantity by A/D converter, a digital quantity proportional to the excursion is applied to one input of the digital comparator and to the controller 16. If the electrocardiogram excursion exceeds the sensing threshold, the controller processes the signal as a cardiac depolarization, measuring the amplitude of the depolarization wave, initiating the refractory period 358 and predetermined period, and measuring the amplitude of noise deflections detected in the noise measurement window 360. Once the refractory period 358 times out, the controller 16 initiates a sequence to determine and adjust the sensing threshold 356. The sequence that the controller 16 follows will now be discussed. First, the detected cardiac depolarization or r-wave amplitude is "smoothed" or "averaged"

$$Ravg(t)=1/4R(t)+3/4Ravg(t-1),$$

according to the following equations:

$$Ravg(t)=Ravg(t-1)-rm,$$

wherein the first equation is applied if the detected cardiac depolarization is intrinsic (see FIG. 30, block 370) and the second equation is applied if the detected cardiac depolarization results from pacing stimulus (see block 372). R(t) is the current amplitude of the cardiac depolarization, Ravg(t−1) is the previous "smoothed" r-wave amplitude, and rm is a preselected constant that, without limitation, may range between 0.001–2.5 mV. The preselected constant, rm, will vary depending upon whether sensing in the atrial autosense or ventricular autosense mode, with 0.14 mV being preferred for ventricular autosense and 0.03 mV being preferred for atrial autosense. Those skilled in the art will recognize and appreciate that the rm may, for convenience, be set equal to the resolution of the A/D converter 26. Once a current "smoothed" r-wave amplitude is determined, then the noise level is determined (see blocks 374 and 376) from the following equation:

$$N(t)=Max[Min(5\ mV;\ NW\ Amp);0.375\ mV;\ N(t-1)-rm]$$

wherein NW Amp is the maximum amplitude of noise measured in the noise measurement window 360, N(t−1) is the previously determined noise level, and rm is a preselected constant as described previously. After the noise level and current "smoothed" r-wave amplitude are determined, then a value for the sensing threshold may be determined according to the following equation:

$$Stdnext(t) = Max\left[\frac{Ravg(t)-N(t)}{x}+N(t);\ ymV;\ zN(t)\right]$$

wherein Stdnext(t) is defined as the next sensing threshold, x is a constant ranging between 1–5 with 2 being preferred for atrial autosense and 3 being preferred for ventricular autosense (see blocks 378 and 380). In the alternative, x may be set as a $$x = \frac{Ravg(t)}{N(t)}$$

function of noise. For example, the following equation may apply:

Likewise, x may be set equal to the current smoothed cardiac depolarization amplitude (x=Ravg(t)); y is a constant ranging between 0.05–5 mV with 0.10 mV being preferred for intrinsic atrial autosense, 0.75 mV being preferred for intrinsic ventricular autosense, 1.5 mV being preferred for paced ventricular autosense, and 0.75 mV being preferred for paced atrial autosense; and z is a constant ranging between 1.0–5.0 with 1.5 being preferred in either atrial or ventricular autosense. In this manner, the sensing threshold will be minimized without reducing the threshold below an acceptable signal to noise (SNR) ratio, thereby improving the rhythm management device's sensing performance and efficiency.

Figure 31:
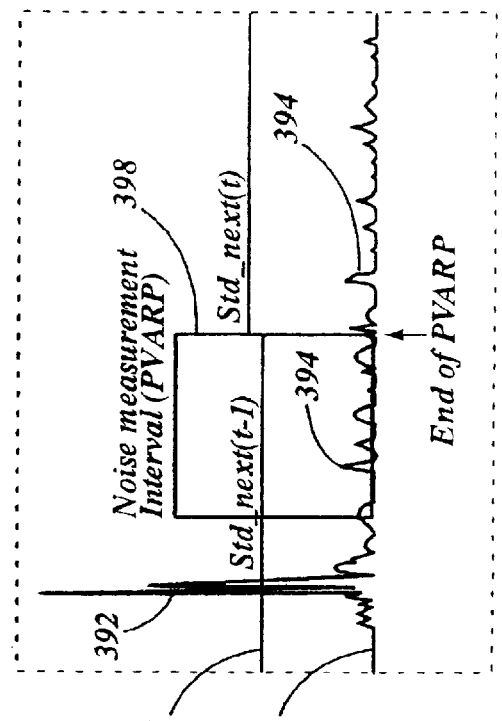
FIG. 31 is a graph of a filtered electrocardiogram signal showing a noise measurement interval implemented for atrial autosense.

Referring next to FIG. 31, there is shown generally an electrocardiogram signal typically received by an implantable cardiac rhythm management device set in an atrial autosense mode that incorporates the improvements of the present invention. The electrogram signal represented by the waveform 390 includes a cardiac depolarization or p-wave deflection 392 and numerous noise deflections 394. The atrial autosense mode includes a sensing threshold which is represented by line 396 and a post ventricular atrial refractory period or PVARP represented by line 398. Although the predetermined period or noise measurement interval is shown coinciding with the PVARP interval, those skilled in the art will appreciate that the predetermined period may be initiated prior to or after the PVARP is initiated and may be longer or shorter than the PVARP. Once a p-wave is detected by the controller 16, a timer and counter are initialized and a PVARP is executed. During PVARP, all detected deflections are presumed noise, wherein the maximum amplitude of the noise deflections is determined by the peak detector 166. A conventional RC charging circuit with a long discharging rate may also be utilized such that at the end of PVARP, the RC charging circuit should be discharged completely. Also, the number of detected deflections during the noise measurement interval are counted and the controller 16 ensures that the detected deflections are not resulting from fibrillation or atrial flutter. If the rate of detected deflections exceeds a predetermined amount, the deflections are presumed noise and the amplitude of the deflections are measured, wherein the predetermined amount may range between 300–600 deflections/ minute with 500 deflections/ minute being preferred. If the rate of deflections is less than the predetermined amount but greater than the Upper Rate Limit (URL; a preprogrammed maximum time that the pacer is allowed to pace) the deflections are a presumed result of atrial flutter or fibrillation.

As described in greater detail below, the software utilized by the controller 16 determines a value for the sensing threshold (utilizing a comparator, for example) from the amplitude of the cardiac depolarization, the maximum amplitude of noise during the noise measurement interval, and from the quantity of noise deflections detected during a previously noise measurement interval. The algorithm that may be utilized by the controller 16 during atrial autosense varies depending upon whether the cardiac event is intrinsic or paced. Once a cardiac depolarization is detected, a timer circuit and counter are initialized. At the end of the noise measurement window and PVARP, the controller 16 implements the sequence shown in FIGS. 32 and 33. For ease of discussion, the following definitions apply to the symbols used in the Figures.

| | |
|---|---|
| Rate_NEI = | rate of counted deflections during noise measurement interval exceeding the previous sensing threshold |
| Std_next(t) = | the next sensing threshold value |
| Std_next(t−1) = | the previous sensing threshold value |
| P(t) = | the current p-wave amplitude |
| Nm(t) = | measured noise amplitude within the current noise measurement interval |
| Pavg(t) = | current smoothed p-wave amplitude value |
| Pavg(t−1) = | previous smoothed p-wave amplitude value |
| N(t) = | current noise level |
| N(t−1) = | previous noise level |
| SNR = | signal to noise ratio |
| sm = | constant |
| RNW = | retriggerable noise window |

Figure 32:
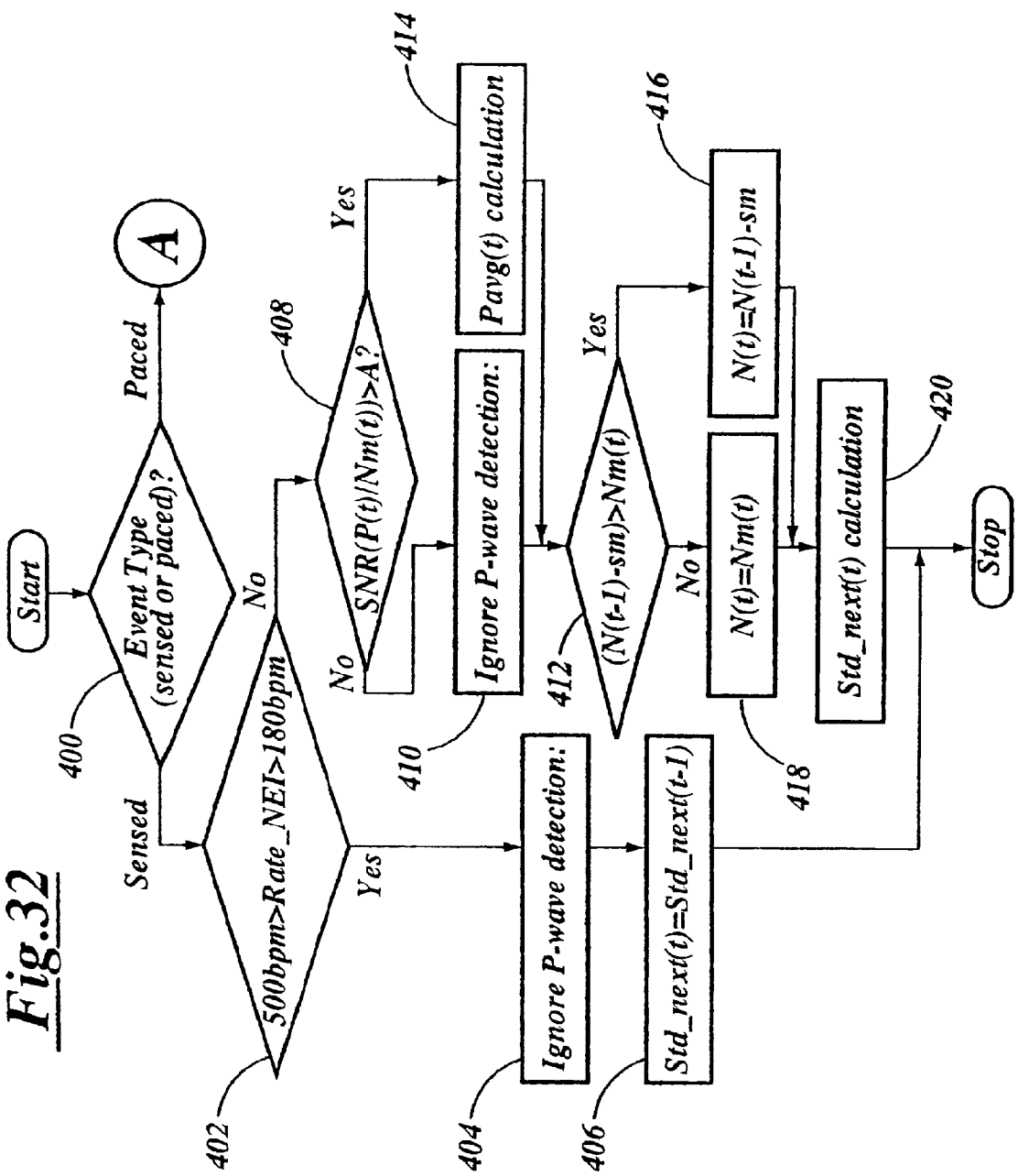
FIGS. 32 and 33 together is a software flow diagram of the autosense algorithm of the present invention following the measurement of noise for atrial autosense.

At the end of the noise measurement interval the controller 16 implements a subroutine that first determines whether the sensed cardiac depolarization is a result of a pacing stimulus or is an intrinsic event (see FIG. 32 decision block 400). If the cardiac depolarization is a result of a pacing stimulus, the controller 16 follows the sequence shown in FIG. 33 which is interconnected with the flowchart in FIG. 32 by connector "A" . If the cardiac depolarization is a result of an intrinsic event, the controller 16 then determines the rate, in beats per minute (bpm), of the number of deflections during the noise measurement interval having an amplitude that exceeds the preceding sensing threshold level (see decision block 402). If the rate of the number of deflections is greater than 180 bpm but less than 500 bpm the p-wave detection is ignored (see block 404) and the sensing threshold value is set equal to the previous sensing threshold value (see block 406). When the rate of the number of deflections is greater than 180 bpm but less than 500 bpm, it is considered that the detected deflections are the result of atrial flutter or fibrillation. Without any limitation intended, in accordance with the above description, the predetermined lower limit may be set equal to the URL, which may preferably be set at 250 bpm.

If the rate of the number of deflections is not between 180–500 bpm then the Signal to Noise Ratio (SNR) is determined and compared to a predetermined constant A (see decision block 408). The SNR is determined by taking the measured amplitude of the p-wave cardiac depolarization and dividing by the measured noise amplitude, wherein the measured noise amplitude may be either the maximum amplitude of noise detected during the noise measurement interval or the average of all noise deflections detected during the noise measurement interval. The predetermined constant A is preferably set at 2 but may range between 1.5–5. If the SNR does not exceed the preset constant A, the p-wave detection is ignored, (see block 410) and the controller determines whether the previous noise level minus a constant "sm" exceeds the measured noise level (see decision block 412). If the SNR exceeds the preset constant A, then the current "smoothed" p-wave (Pavg(t)) is determined (see block 414) in accordance with the following:

$$Pavg(t)=1/4P(t)+3/4Pavg(t-1)$$

where P(t) is measured amplitude of the p-wave and Pavg (t−1) is the value for the previous "smoothed" p-wave. Once the Pavg(t) is determined, then the controller determines whether the previous noise level minus a constant "sm" exceeds the measured noise level (see decision block 412), where constant sm, without limitation, may range between 0.01–0.5 mV, with 0.05 mV being preferred. If the previous noise level minus constant sm exceeds the current measured noise amplitude, the noise level is set equal to the previous noise level minus the constant sm (see block 416), otherwise, the noise level is set equal to the measured noise amplitude within the current noise measurement interval (see block 418). Once a noise level value and "smoothed" p-wave value have been determined, the next sensing threshold is determined in accordance with the following:

$$Stdnext(t) = \text{Max}\left[\frac{Pavg(t) - N(t)}{x} + N(t); ymV; zN(t)\right]$$

where x, y, and z are constant values having a range as previously described. The controller 16 then sets the ATH 170, for example, equal to the calculated value and sensing continues until the next cardiac depolarization is sensed.

Figure 33:
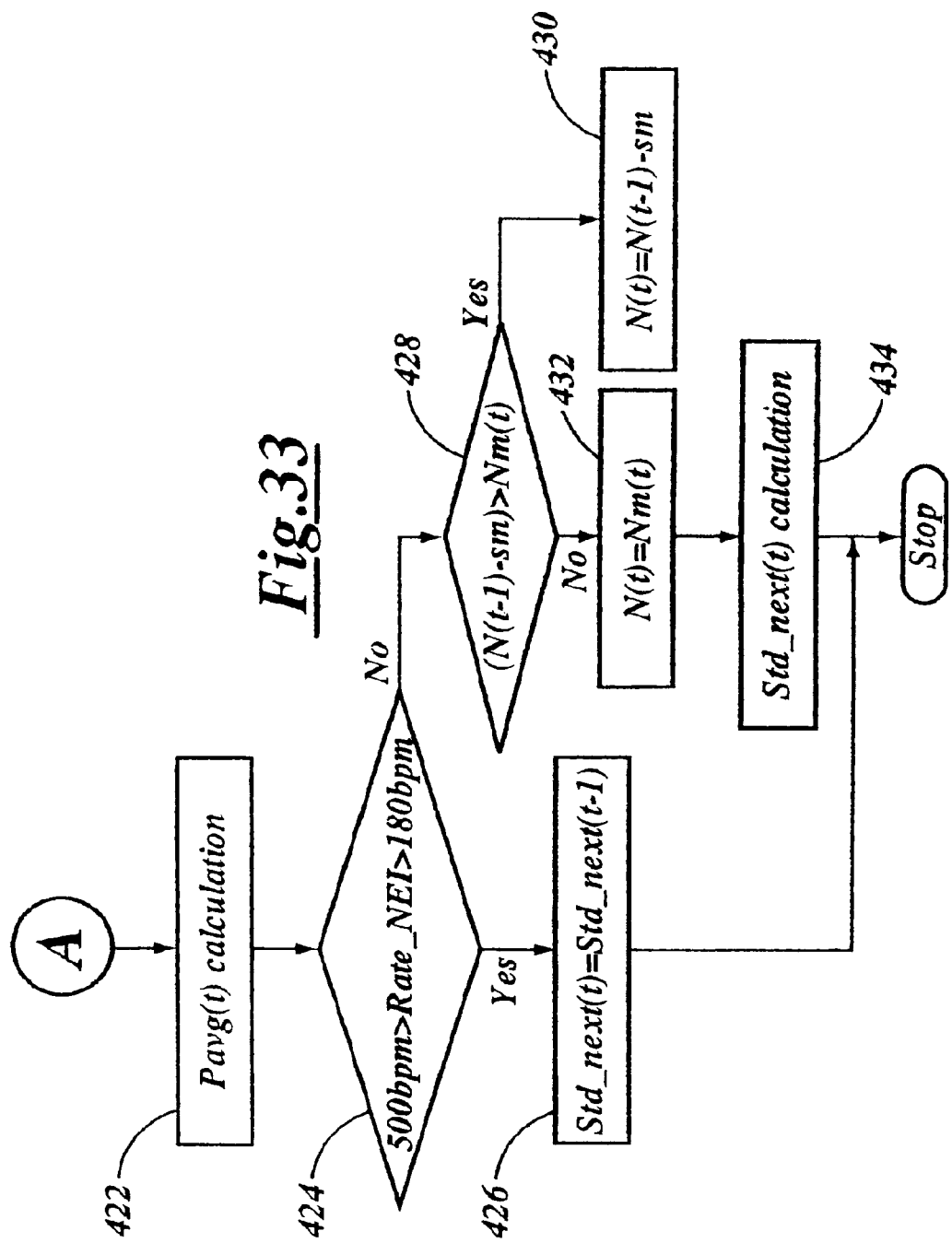

Referring again to connector "A" and FIG. 33, if the detected cardiac depolarization is the result of a pacing stimulus, following the end of the noise measurement interval the controller 16 determines the "smoothed" p-wave value (see block 422 from the following equation:

$$Pavg(t)=Pavg(t-1)-sm$$

Once a value for the "smoothed" p-wave is determined, the controller 16 then determines the rate, in beats per minute (bpm), of the number of deflections during the noise measurement interval having an amplitude that exceeds the preceding sensing threshold level (see decision block 424). If the rate of the number of deflections is greater than 180 bpm but less than 500 bpm the next sensing threshold is set equal to the previous sensing threshold value (see block 426).

If the rate of the number of deflections is not between 180–500 bpm then the controller determines whether the previous noise level minus a constant "sm" exceeds the measured noise level (see decision block 428), where constant sm, without limitation, may range between 0.01–0.5 mV, with 0.05 mV being preferred. If the previous noise level minus constant sm exceeds the current measured noise amplitude, the noise level is set equal to the previous noise level minus the constant sm (see block 430), otherwise, the noise level is set equal to the measured noise amplitude within the current noise measurement interval (see block 432). Once a noise level value and "smoothed" p-wave value have been determined, the next sensing threshold is determined in accordance with the following:

$$Stdnext(t) = \text{Max}\left[\frac{Pavg(t) - N(t)}{x} + N(t); ymV; zN(t)\right]$$

where x, y, and z are constant values having a range as previously described. The controller 16 then sets the ATH 170, for example, equal to the calculated value and sensing continues until the next cardiac depolarization is sensed.

Figure 34:
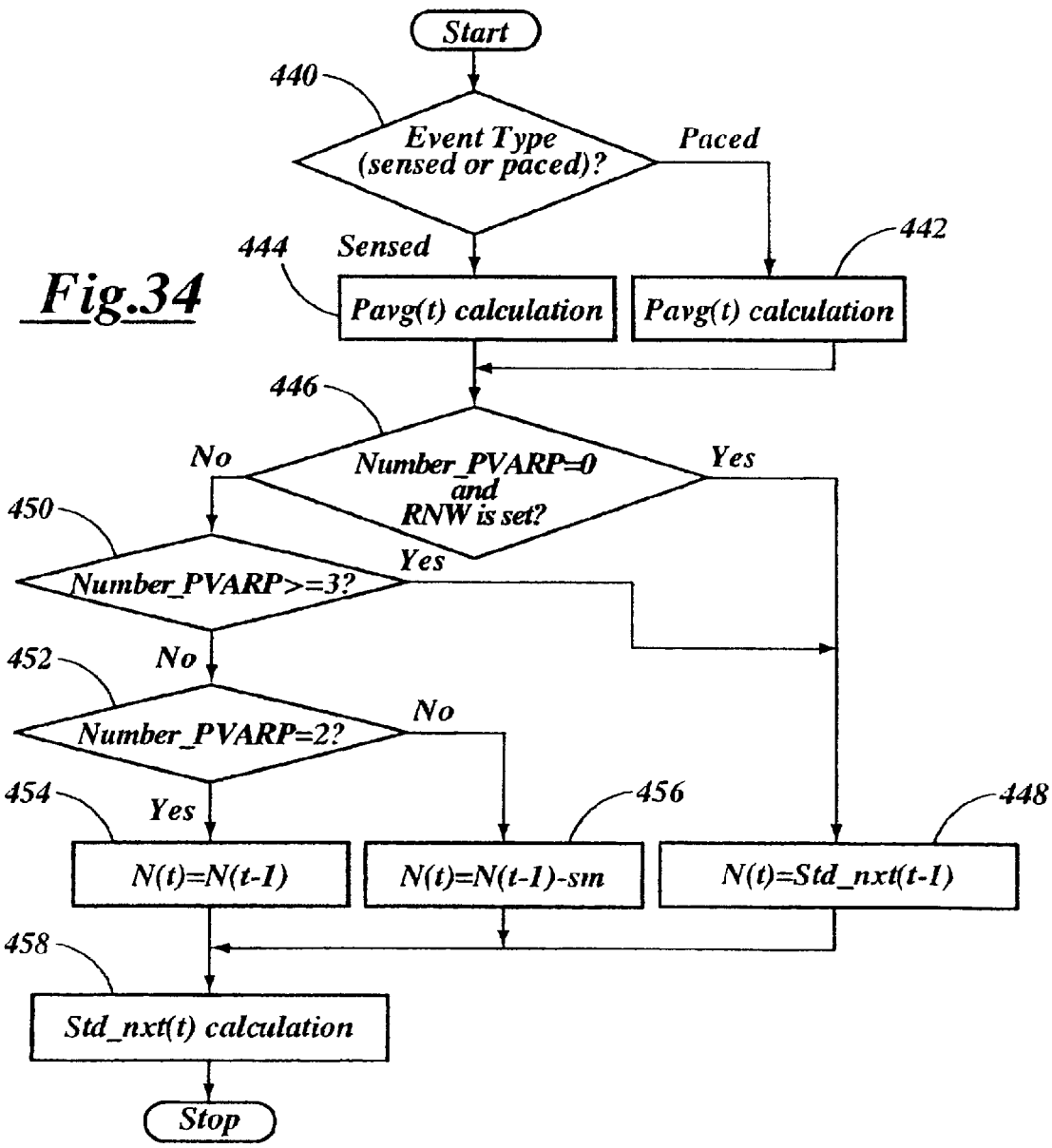
FIG. 34 is a software flow diagram of an alternate autosense algorithm of the present invention for atrial autosense.
Figure 35:
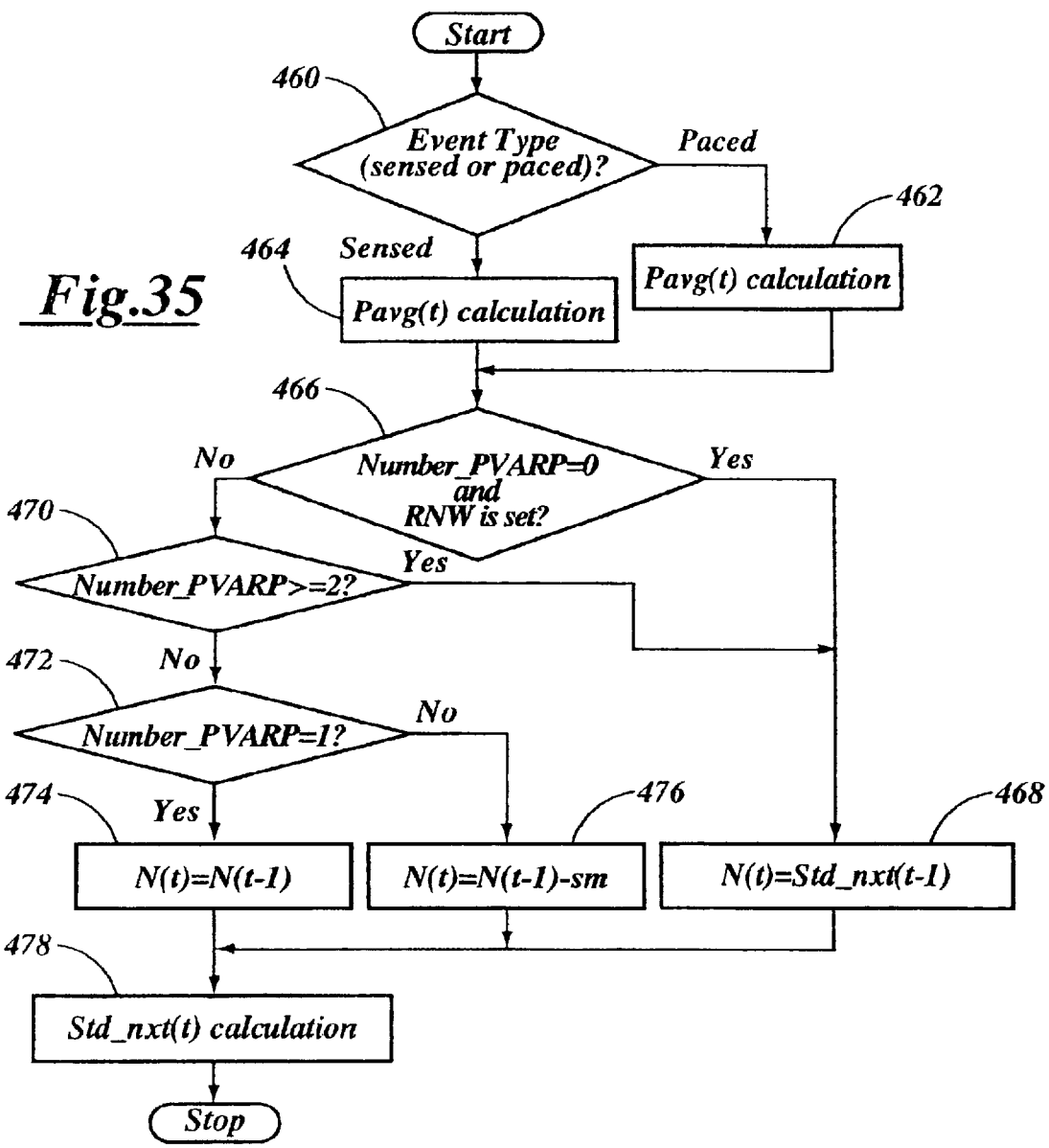
FIG. 35 is a software flow diagram of an alternate autosense algorithm of the ,present invention for atrial autosense.

Referring next to FIGS. 34 and 35, alternate preferred algorithms are shown that may be implemented by a cardiac rhythm management device incapable of a direct measurement of the amplitude of noise while in an atrial autosense mode. The sequence shown in FIG. 34 is implemented by the controller 16 when the PVARP is set equal to 250 ms or the PVARP exceeds 250 ms. The sequence shown in FIG. 35 is implemented when the PVARP is less than 250 ms. In the case where PVARP exceeds 250 ms, the "smoothed" p-wave amplitude and the number of events exceeding the sensing threshold is determined over a preset period (250 ms) of time or noise measurement interval within the PVARP interval.

The sequence shown in FIG. 34 is implemented by the controller after the noise measurement interval or PVARP times out. The controller 16 then determines whether the current cardiac depolarization is a result of a paced or intrinsic event (see decision block 440). If the cardiac depolarization is the result of a paced stimulus the controller 16 calculates the "smoothed" amplitude (see block 442) for the detected p-wave deflection in accordance with the following equation:

$$Pavg(t)=Pavg(t-1)-sm$$

where, without limitation, sm is a constant ranging between 0.01–0.5 mV, with 0.05 mV being preferred. If the cardiac depolarization is the result of a sensed stimulus the controller 16 calculates the "smoothed" amplitude (see block 444) for the detected p-wave deflection in accordance with the following equation:

$$Pavg(t)=1/4P(t)+3/4Pavg(t-1)$$

as previously described. The controller then determines the number of deflections counted exceeding the sensing threshold during the predetermined period. If there were no deflections detected during the noise measurement interval and the retriggerable noise window of 40 ms, for example, is set (see decision block 446), then the noise amplitude value is set equal to the previous sensing threshold value (see block 448). If deflections are detected during the noise measurement interval, and the number of detected deflections exceed 3 (see decision block 450), then the noise amplitude value is set equal to the previous sensing threshold value (see block 448). If the number of detected deflections equals 2 (see decision block 452), then the value for the amplitude of noise is set equal to the previous amplitude of noise value (see decision block 454), otherwise, the amplitude of noise value is set equal to the previous value for the amplitude of noise minus a constant "sm" as previously described (see block 456). In this manner the measured amplitude of noise is estimated for the current noise measurement interval. Once the "smoothed" amplitude of the p-wave deflection and the amplitude of noise are calculated, then the value for the next sensing threshold is determined in accordance with the following:

$$Stdnext(t) = \text{Max}\left[\frac{Pavg(t) - N(t)}{x} + N(t); ymV; zN(t)\right]$$

where x, y, and z are constant values having a range as previously described (see block 458). The controller 16 then sets the ATH register 170, for example, equal to the calculated value and sensing continues until the next cardiac depolarization is sensed.

As previously indicated, the sequence shown in FIG. 35 is implemented by the controller 16 after the noise measurement interval or predetermined period times out and when the PVARP is less than 250 ms. When this is the case, the controller 16 determines whether the current cardiac depolarization is a result of a paced or intrinsic event (see decision block 460). If the cardiac depolarization is the result of a paced stimulus the controller 16 calculates the "smoothed" amplitude (see block 462) for the detected p-wave deflection in accordance with the following equation:

$$Pavg(t)=Pavg(t-1)-sm$$

where, without limitation, sm is a constant ranging between 0.01–0.5 mV, with 0.05 mV being preferred. If the cardiac depolarization is the result of a sensed stimulus the controller 16 calculates the "smoothed" amplitude (see block 464) for the detected p-wave deflection in accordance with the following equation:

$$Pavg(t)=1/4P(t)+3/4Pavg(t-1)$$

as previously described. The controller then determines the number of deflections counted exceeding the sensing threshold during the PVARP interval. If there were no deflections detected during the noise measurement interval and the retriggerable noise window of 40 ms, for example, is set (see decision block 466), then the noise amplitude value is set equal to the previous sensing threshold value (see block 468). If deflections are detected during the noise measurement interval, and the number of detected deflections exceed 2 (see decision block 470), then the noise amplitude value is set equal to the previous sensing threshold value (see block 468). If the number of detected deflections equals 1 (see decision block 472), then the value for the amplitude of noise is set equal to the previous amplitude of noise value (see decision block 474), otherwise, the amplitude of noise value is set equal to the previous value for the amplitude of noise minus a constant "sm" as previously described (see block 476). In this manner the measured amplitude of noise is estimated for the current noise measurement interval. Once the "smoothed" 25 amplitude of the p-wave deflection and the amplitude of noise are calculated, then the value for the next sensing threshold is determined in accordance with the following:

$$Stdnext(t) = \text{Max}\left[\frac{Pavg(t) - N(t)}{x} + N(t); ymV; zN(t)\right]$$

where x, y, and z are constant values having a range as previously described (see block 478). The controller 16 then sets the ATH register 170, for example, equal to the calculated value and sensing continues until the next cardiac depolarization is sensed.

Figure 37:
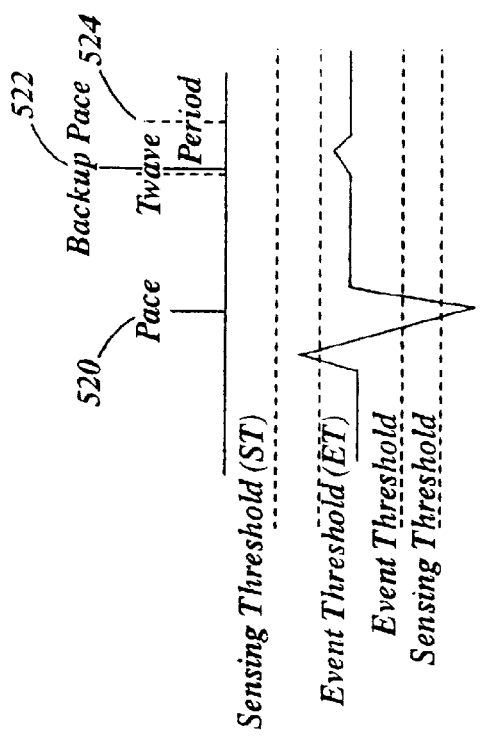
FIG. 37 is a graph showing pseudo-fusion that is detected as non-capture and resulting in pacing during an intrinsic event and a backup pace proximate in time with a t-wave or vulnerable period following an intrinsic event.
Figure 36:
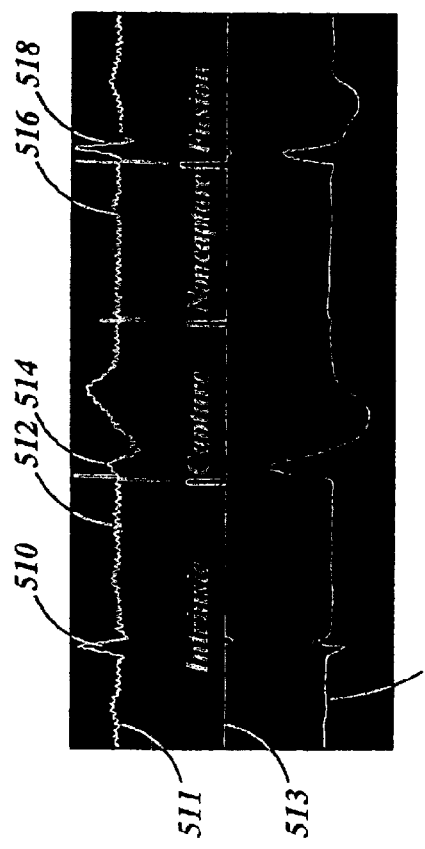
FIG. 36 shows a strip chart tracing of an electrocardiogram waveform identifying intrinsic, capture, non-capture and fusion together with the corresponding strip chart tracing of a surface ECG shown for comparison and reference.

The rhythm management device of the present invention automatically adjusts the detection threshold as described above and may also adjust the detection threshold dependent upon the occurrence of fusion or pseudo-fusion during an autothreshold determination. A strip chart and graph are shown in FIGS. 36 and 37 wherein the affects of fusion and pseudo-fusion in a pacing scheme are shown. The three waveforms 511, 513, and 515 shown in FIG. 36 correspond to a signal transmitted from a surface electrocardiogram, an associated pacing marker, and a processed signal transmitted from an intracardiogram respectively. The timing sequence in FIG. 36 shows an intrinsic event 510 and then a period of time transpiring without a detection of another intrinsic event. After a predetermined amount of time transpires without detecting an intrinsic event, a pacing stimulus 512 is delivered which evokes a response at 514. The timing sequence shown in FIG. 36 continues to deliver pacing stimulus if an intrinsic event is not sensed within a predetermined time. The pacing stimulus 516 is delivered in accordance with the predetermined timing sequence, but results in a fusion beat because the pacing stimulus 516 is delivered at the beginning of an intrinsic event 518. Although fusion and capture may be distinguished from a surface electrocardiogram waveform, fusion and capture beats are not distinguishable from the intracardiogram waveform 515.

Figure 38:
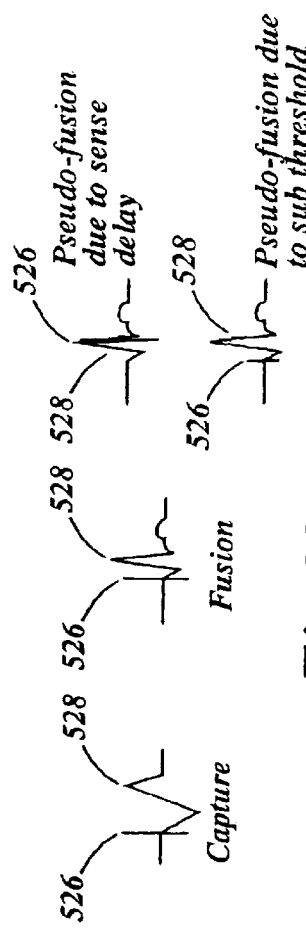
FIG. 38 shows graphs of the timing of a stimulation pulse delivered during various stages of a captured or intrinsic event.

As seen in FIG. 37, a pacing stimulus 520 may be delivered during a QRS complex, thus requiring a backup pace 522 proximate the T-wave or vulnerable period 524. Delivery of a backup pace 522 proximate the vulnerable period may lead to an undesirable arrhythmia and may be avoided by reducing fusion and pseudo-fusion during autocapture and autothreshold determination. FIG. 38 further illustrates four possible timing sequences resulting from delivery of a pacing stimulus 526. The timing sequence identified as "Capture" shows delivery of a pacing stimulus that evokes a response. The other three timing sequences show delivery of a pacing stimulus proximate with an intrinsic event 528.

Figure 39:
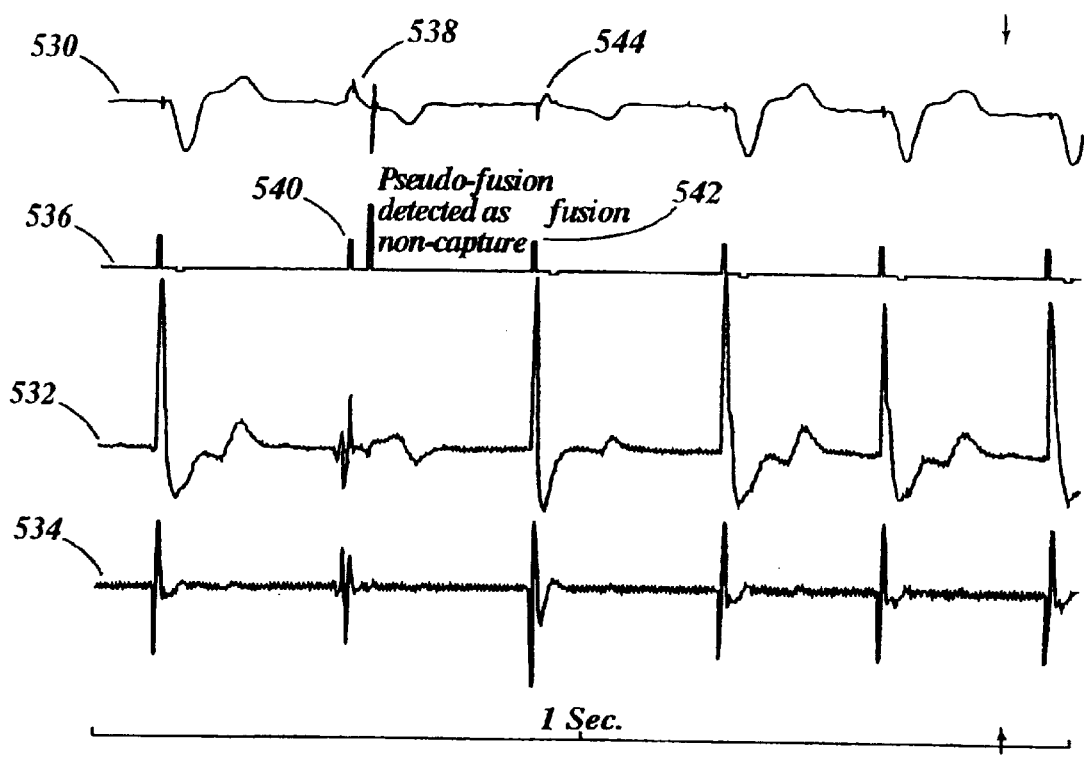
FIG. 39 shows a strip chart tracing showing "pseudo-fusions" detected as capture and non-capture and the resulting stimulation sequences, together with a strip chart tracing of a surface ECG for reference.
Figure 40:
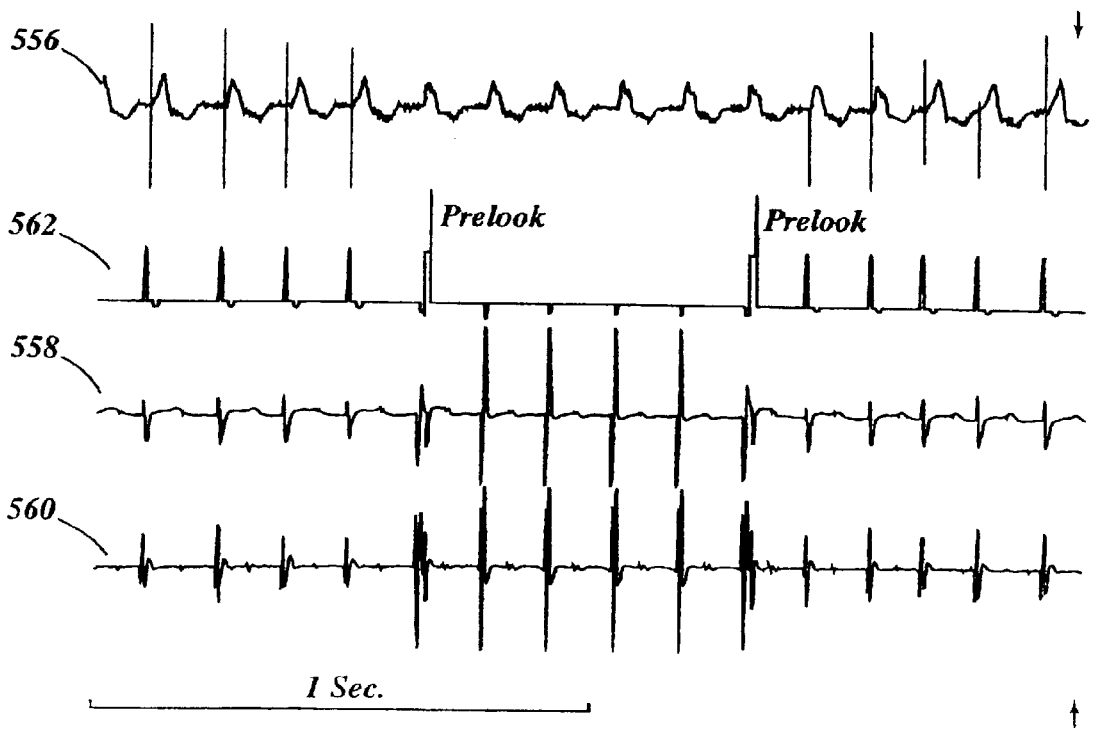
FIG. 40 shows a strip chart tracing showing the stimulation sequence including two "pre-looks", together with a strip chart tracing of a surface ECG for reference.

Referring now to FIGS. 39 and 40, strip charts of a portion of an electrogram single are shown which illustrate the affects of fusion and pseudo-fusion on a pacing interval and mode (see FIG. 39) and the implementation of the present invention to avoid fusion and pseudo-fusion (see FIG. 40). The waveforms 530–534 and associated pacing marker 536 shown in FIG. 39 illustrate the affects of a fusion or pseudo-fusion beat on the ability to accurately determine capture or autothreshold. The waveform 530 results from a signal transmitted from a surface electrocardiogram. The waveform 532 results from a signal transmitted from an intracardiogram and processed through a wideband channel of approximately 6–200 Hz. The waveform 534 results from a signal transmitted from an intracardiogram and processed through a narrower band channel of approximately 10–100 Hz. The intrinsic event identified at 538 is not identified by the pacer and therefore a pace 540 is initiated followed by a backup pace. The pacing stimulus does not evoke a response and the controller process then concludes that the pacing stimulus at 540 did not evoke a response (non-capture). The pacing stimulus at 542 immediately precedes an intrinsic event 544, which results in a fusion beat and also affects an accurate determination of capture. The waveforms 556–560 and associated pacing marker 562 shown in FIG. 40 illustrates delivery of a pacing stimulus with a pre-look, thereby avoiding fusion and pseudo-fusion. The waveform 556 results from a signal transmitted from a surface electrocardiogram. The waveform 558 results from a signal transmitted from an intracardiogram and processed through a wideband channel of approximately 6–200 Hz. The waveform 560 results from a signal transmitted from an intracardiogram and processed through a narrower band channel of approximately 10–100 Hz.

Figure 41:
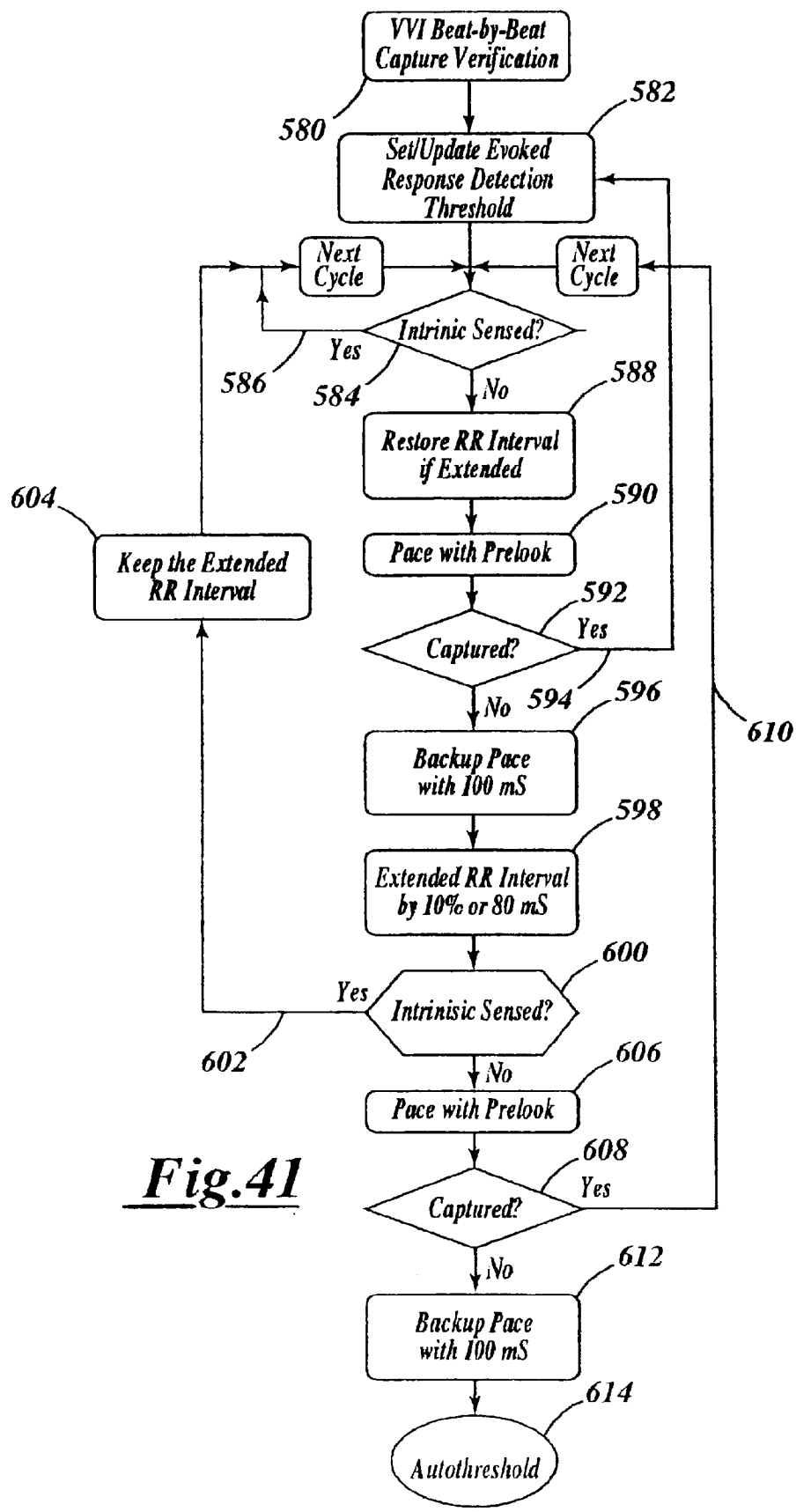
FIG. 41 is a flow chart showing a beat by beat capture verification sequence that includes delivery of a stimulation pulse with a pre-look.

Referring now to FIG. 41, without any limitation intended the sequence of VVI beat by beat capture verification utilizing the method of the present invention is shown in a flowchart diagram. A controller of the rhythm management device initiates a beat by beat capture verification at block 580. The controller then updates the evoked response detection threshold (see block 582) and a determination is made whether an intrinsic event is sensed or whether the amplitude of a selected portion of the electrogram signal exceeds the intrinsic detection threshold (see decision block 584). If an intrinsic event is sensed, the controller determines if an intrinsic event is sensed in the next cycle (see loop 586). If an intrinsic event is not sensed, then the RR interval of the various pacing intervals is restored to the preset amount (assuming that the RR interval had been extended; see block 588) and a pacing stimulation is delivered with prelook (see block 590). Delivery of a stimulation pulse with prelook will be further discussed below in conjunction with a discussion of FIG. 43. After a stimulation pulse is delivered, the controller determines whether the output or pacing stimulus results in an evoked response or capture (see decision block 592). If the stimulation pulse results in capture, the evoked response detection threshold is updated and the previous steps are repeated (see loop 594) and beat by beat pacing continues. If the pacing stimulus does not result in capture at decision block 592, then the controller initiates a backup pace within a predetermined time (see block 596) and the RR interval is extended by a predetermined amount (see block 598). Without limitation, the backup pace is preferably initiated within 100 ms and the RR interval is extended by 10% or by 80 ms. The controller then determines whether an intrinsic event occurs within a predetermined time (see decision block 600). If an intrinsic event is sensed at decision block 600, then the extended RR interval is kept and the controller determines if an intrinsic event is sensed in the next cycle (see loop 602 and block 604). If an intrinsic event is not sensed at decision block 600, then a stimulation pulse with prelook is delivered (see block 606) and capture of this pulse is determined (see decision block 608). If the stimulation with prelook results in capture then beat by beat pacing continues (see loop 610). If, however, the stimulation with prelook does not evoke a response, then a backup pace is initiated within a predetermined time (see block 612) and the controller switches to an autothreshold determination.

Figure 42:
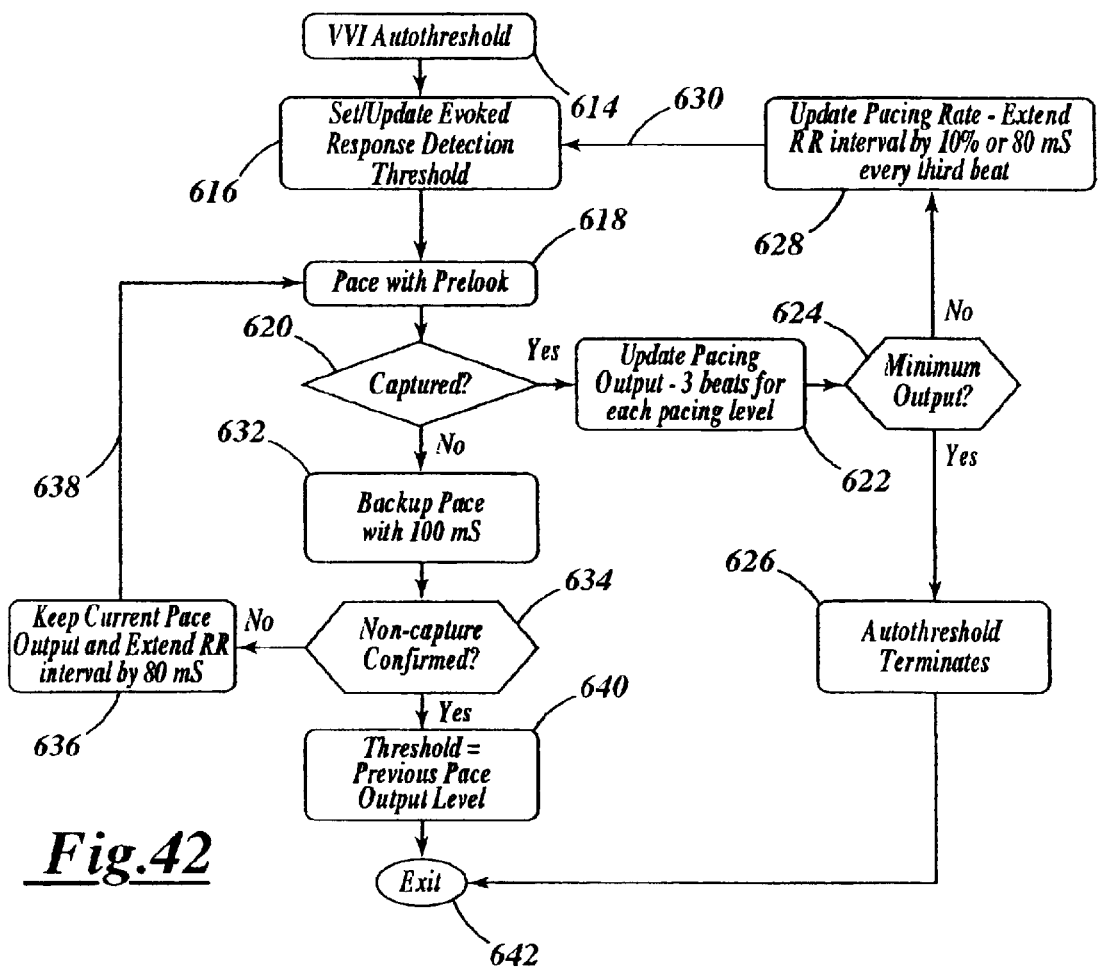
FIG. 42 is a flow chart showing an autothreshold sequence that includes delivering a stimulation pulse with a pre-look.

FIG. 42 is a flowchart representation of an autothreshold determination (see block 614) in accordance with the present invention. First, the evoked response detection threshold is set or updated (see block 616). A stimulation pulse with prelook is delivered having a predetermined output (see block 618) and the controller determines whether the stimulation pulse evokes an intrinsic response (see decision block 620). If the stimulation pulse results in capture, the pacing output is updated (see block 622) and the pacing output is compared with a preset minimum threshold output (see decision block 624). If the pacing output is equal to the preset minimum threshold output, then autothreshold determination is terminated (see block 626). If the updated pacing output is above the minimum preset amount, then, without limitation, the pacing rate is updated for every third beat (see block 628) by extending the RR interval as described previously and autothreshold determination continues (see loop 630). If the stimulation pulse is not captured at decision block 620, then a backup pace having a predetermined output is delivered (see block 632) and the controller attempts to confirm non-capture (see decision block 634). If the controller does not confirm non-capture, then the pacing output remains the same, the RR interval is extended (see block 636) and autothreshold determination continues (see loop 638). If, however, the output results in non-capture, the threshold is set equal to the previous pace output level (see block 640) and autothreshold terminates (see block 642).

Figure 43:
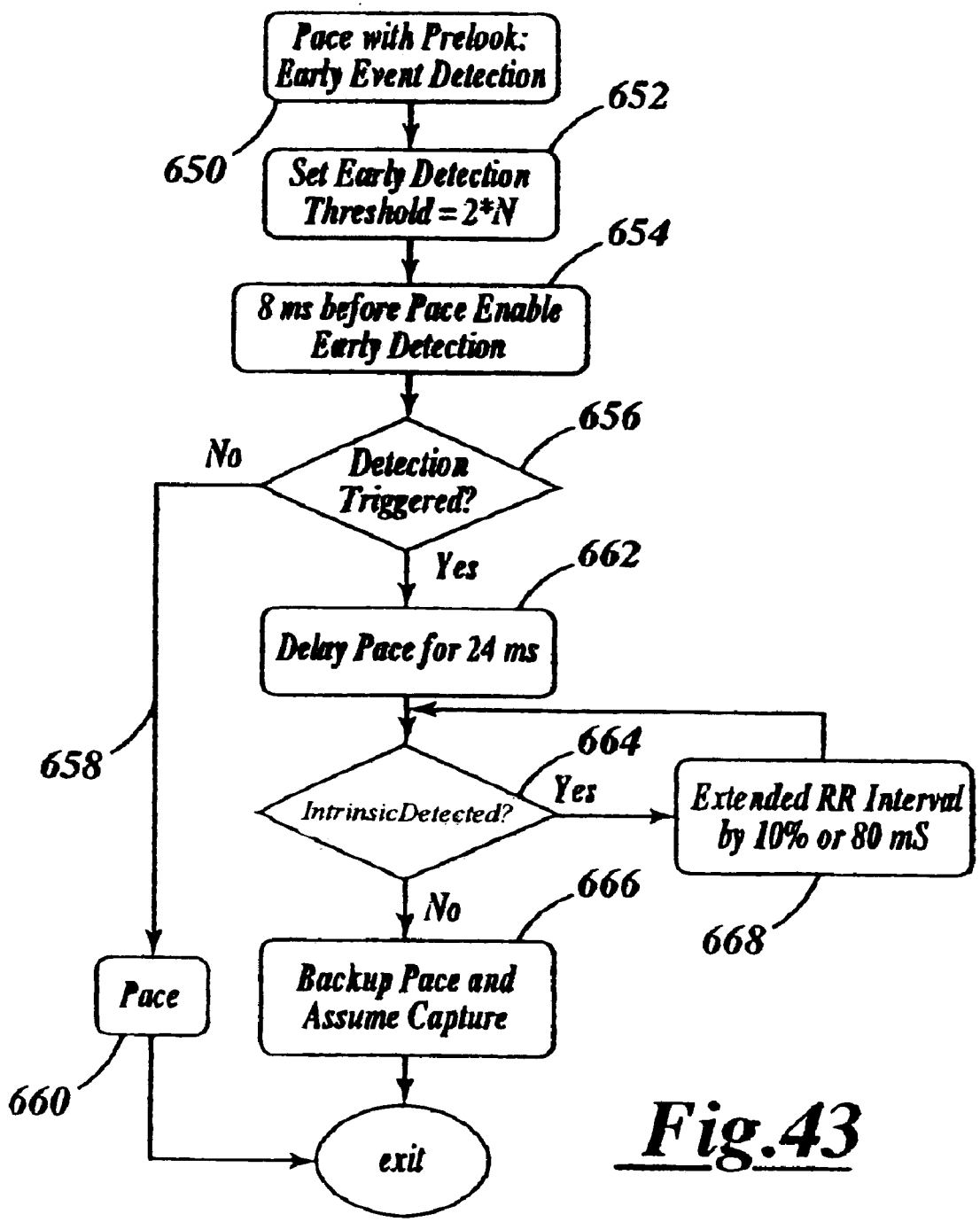
FIG. 43 is a flow chart showing the delivery of a stimulation pulse with a pre-look.

Referring now to FIG. 43, the delivery of a stimulation pulse with prelook will now be described. The controller may initiate a stimulation with prelook (see block 650) during beat to beat, autocapture or autothreshold determination. The controller first sets an early detection threshold equal to two times a predetermined amount "N" and enables the early detection threshold a predetermined time immediately before delivering the stimulation pulse (see blocks 652 and 654. Those skilled in the art will appreciate that the early detection threshold may be determined in a manner similar to determining the event threshold as described above in greater detail. The controller then determines whether the amplitude of a portion of the electrogram signal received during the predetermined time immediately before delivering exceeds the early detection threshold (see decision block 656). If the amplitude of a portion of the electrogram signal does not exceed the early detection threshold, then the stimulation pulse is delivered (see loop 658 and block 660). If the amplitude of a portion of the electrogram signal exceeds the early detection threshold, then delivery of the stimulation pulse is delayed by a predetermined amount (see block 662) and the portion of the electrogram signal is analyzed to determine whether an intrinsic event has occurred (see decision block 664). If no intrinsic event is detected then a backup pace is delivered having an output sufficient to assume capture (see block 666). If an intrinsic event is detected at decision block 664, then the RR interval is extended as described above (see block 668 and continues to be extended until an intrinsic event is not detected (see loop 670), at which time a backup pace is delivered (see block 666).

Figure 44:
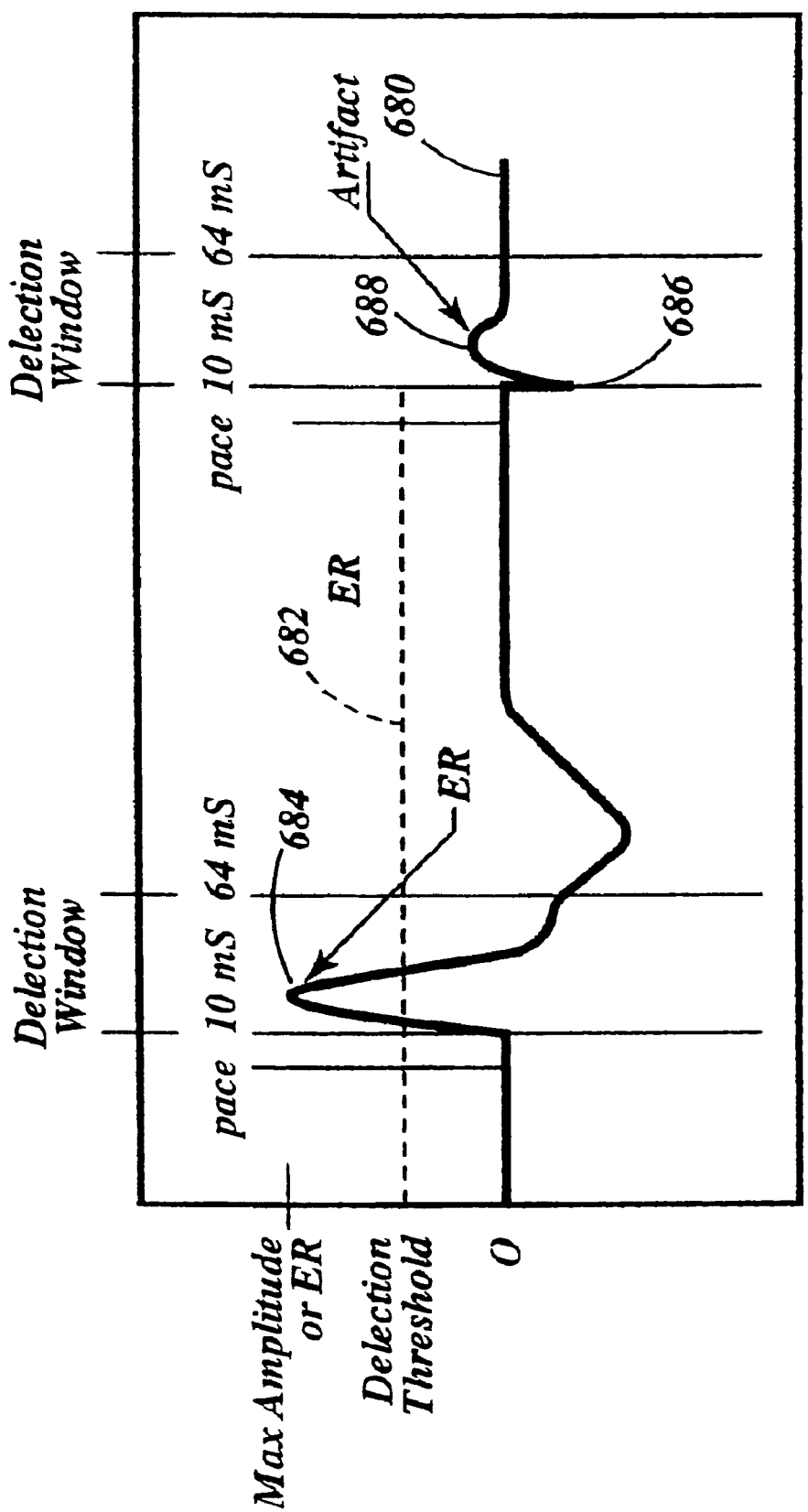
FIG. 44 is a graph of an electrocardiogram signal sensed over time with the sensing circuit of the present invention.

Referring now to FIG. 44, an electrocardiogram signal 680 is shown resulting from a pacing stimulus. Without limitation, a dedicated evoked response sense amplifier is duty cycled and is only turned on by the controller during a predefined capture detection window. The capture detection window shown in FIG. 44 is defined by the time from pacing to 64 msec after pace. Those skilled in the art will appreciate that the capture detection window may be defined either longer or shorter than the period shown in FIG. 44. The evoked response detection threshold is shown by dotted line 682, wherein a positive peak amplitude 684 associated with the evoked response exceeds the evoked response detection threshold. Later in time the artifact associated with recharge is seen having primarily a negative peak amplitude. The minor portion 688 of the signal associated with artifact 688 does not exceed the evoked response detection threshold and does not result in false capture declaration.

Figure 45:
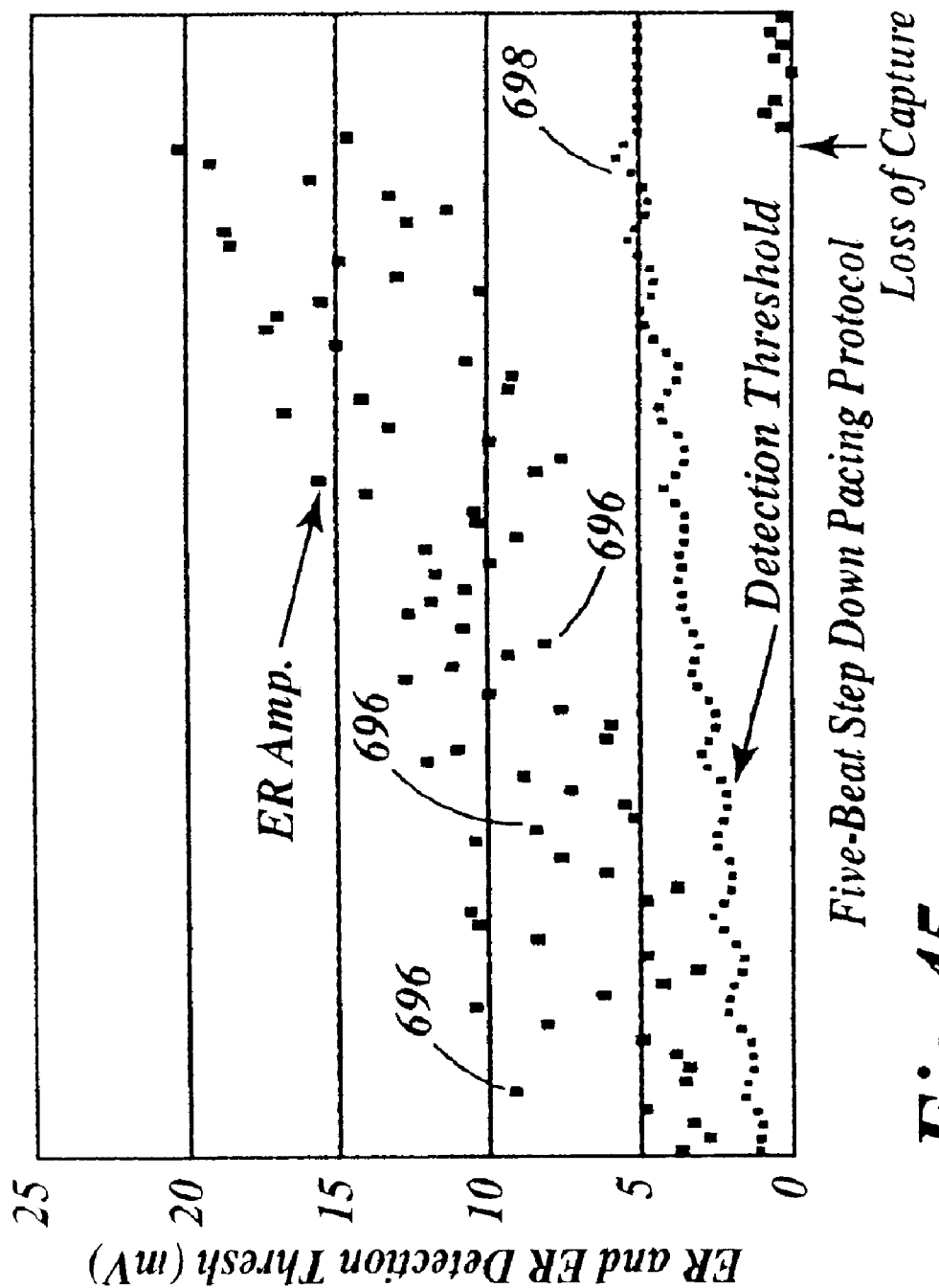
FIG. 45 is a graph of the maximum amplitude of evoked response for several beats during a five-beat step down capture detection pacing protocol.

Referring now to FIG. 45, the maximum amplitude of several R-waves indicated at point 696 are shown measured over time, wherein the "measurements" of the amplitude occurred during a five-beat step down capture detection pacing protocol. The evoked response detection threshold baseline 698 as determined by the method of the present invention is shown, wherein fluctuation in the baseline coincides with the modulation of the evoked response amplitude. In this manner, during beat by beat autocapture, for example, a decrease in the evoked response amplitude is not likely to generate a false negative in capture decision making, thereby eliminating unnecessary backup pacing.

Figure 46:
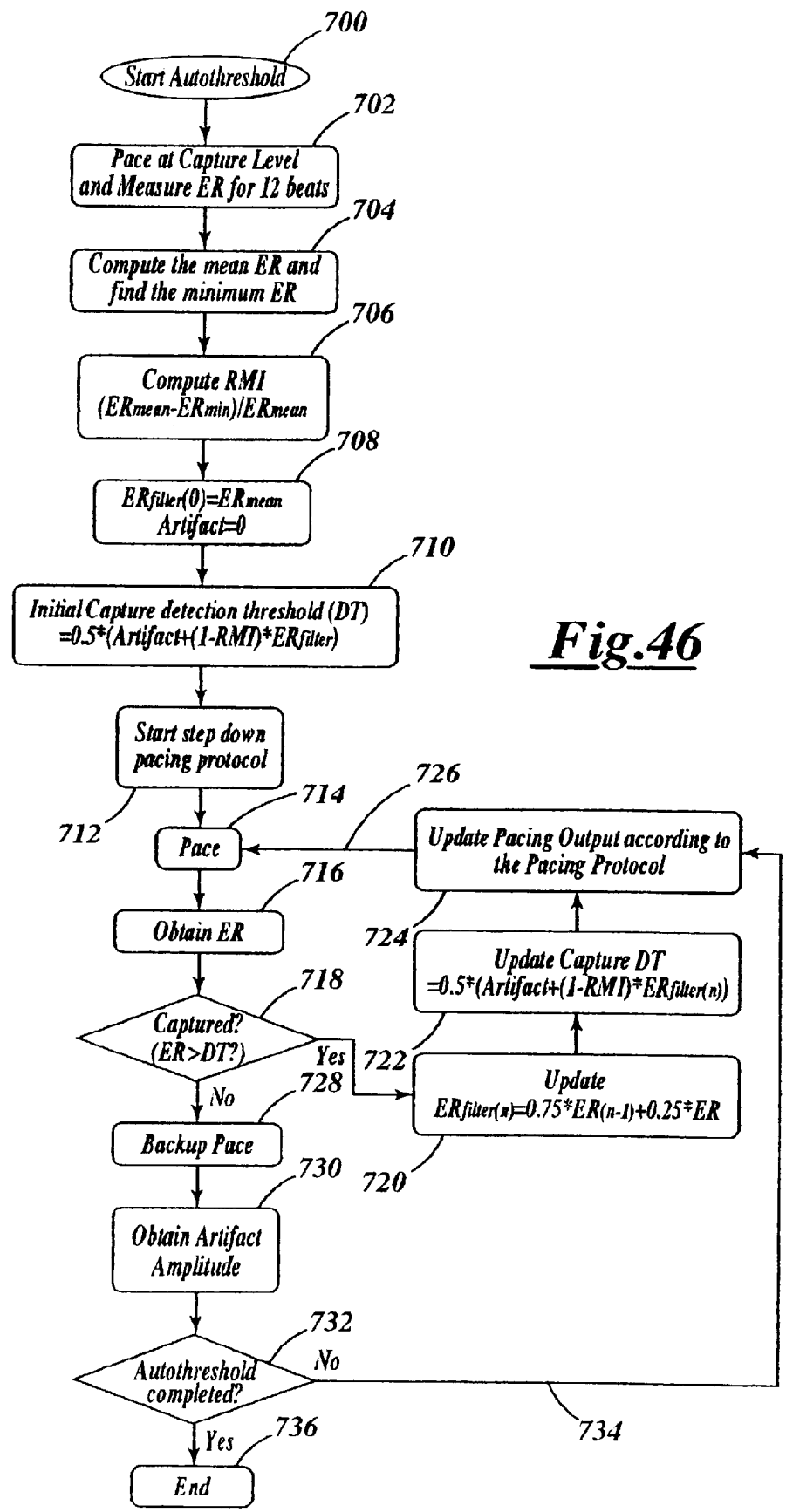
FIG. 46 is a software flow diagram of the automatic adjustment of the evoked response detection threshold algorithm of the present invention.

As discussed above in greater detail, when an electrocardiogram excursion picked up on lead is signal processed by the sense amplifier/filter circuit and converted to a digital quantity by A/D converter, a digital quantity proportional to the excursion is applied to one input of the digital comparator and to the controller. If the electrocardiogram excursion exceeds the sensing threshold, the controller may process the signal as a cardiac depolarization, "measuring" the amplitude of the depolarization wave. Once the amplitude measurements have been made for a predetermined number of beats, the controller initiates a sequence to determine and adjust the evoked response detection threshold. FIG. 46 illustrates another embodiment of determining and modulating the evoked response detection threshold in conjunction with a modulating amplitude of evoked response.

Once the automatic evoked response detection threshold determination is initiated (see FIG. 46, block 700), the patient's heart is paced at the current capture level for a predetermined number of beats. The maximum amplitude of each evoked response over the predetermined number of beats is measured utilizing the peak detector, comparator and controller as described above in greater detail (see block 702). A value associated with each maximum amplitude may be stored in the memory of the controller. The predetermined number of beats should include at least one complete cycle of the respiration modulation. The mean amplitude and minimum amplitude for all of the maximum amplitudes over the predetermined number of beats is then determined and stored (see block 704). A first constant value referred to as the "Respiration Modulation Index" or RMI is determined according to the following equation:

$$(ER_{mean} - ER_{min})/ER_{mean}$$

wherein $ER_{mean}$ is the mean amplitude for all of the maximum amplitudes over the predetermined number of beats and $ER_{min}$ is the minimum amplitude for all of the maximum amplitudes over the predetermined number of beats (see block 706). A second constant value identified as the $ER_{filter}$ (described below in greater detail) is initially set equal to the determined $ER_{mean}$ and a value corresponding to an amplitude of artifact is initially set equal to zero (see block 708). The evoked response detection threshold (ERDT) is then determined according to the following equation:

$$ERDT = k(Artifact + ER_{Min})$$

where k is a predefined constant that may range between 0.1 to 0.9 and $ER_{Min}$ is the minimum evoked response due to modulation. The $ER_{Min}$ takes into account both the modulation due to respiration and the modulation due to other factors as follows:

$$ER_{Min}=(1-RMI)(ER_{Filter})$$

(see block 710). This evoked response detection threshold (ERDT) may be utilized and updated during a capture detection step down pacing protocol (see block 712). A pacing stimulus is delivered and then the rhythm management device senses for an evoked response (see blocks 714 and 716). A determination is then made whether a signal is sensed having an amplitude greater than the ERDT (see decision block 718).

If a maximum amplitude of the sensed signal exceeds the ERDT it is assumed that this signal corresponds to an R-wave and capture is assumed. The value corresponding to the $ER_{Filter}$ is then updated according to the following equation:

$$ER_{Filter(n)} = a(ER_{Filter(n-1)}) + b(ER_n)$$

where n=0 for the initial determination of the $ER_{Filter}$ value and increases by an integer number for each subsequent determination of the ERDT, and "a" and "b" are coefficients wherein a+b=1 (see block 720). In the preferred embodiment "a" is set equal to 0.75 and "b" is set equal to 0.25. Those skilled in the art will appreciate that the $ER_{Filter}$ provides a moving average of the evoked response, thereby adapting the evoked response detection threshold to changes in the evoked response amplitude. The ERDT is updated according to the following equation:

$$ERDT_n = 0.5(Artifact + ((1-RMI)ER_{Filter(n)}))$$

where the RMI is updated at predetermined intervals, with 21 hours being preferred (see block 722). Without limitation, the pacing output may then be updated according to a known suitable pacing protocol (see block 724). The next pace in the pacing step down protocol may be delivered (see loop 726). If after a pacing stimulus is delivered and the maximum amplitude of the electrocardiogram signal does not exceed the ERDT then a backup pace is delivered (see block 728). The artifact amplitude is then measured from the electrocardiogram signal (see block 730) and it is determined whether the autothreshold protocol is complete (see decision block 732). If the protocol is not complete, the pacing output is updated according to known suitable pacing protocol (see loop 734, block 724 and loop 726). If the autothreshold protocol is complete, then the autothreshold is terminated (see block 736). In this manner the detection threshold is defined greater than the amplitude for maximum artifact and less than the amplitude of the minimum evoked response.

Figure 47:
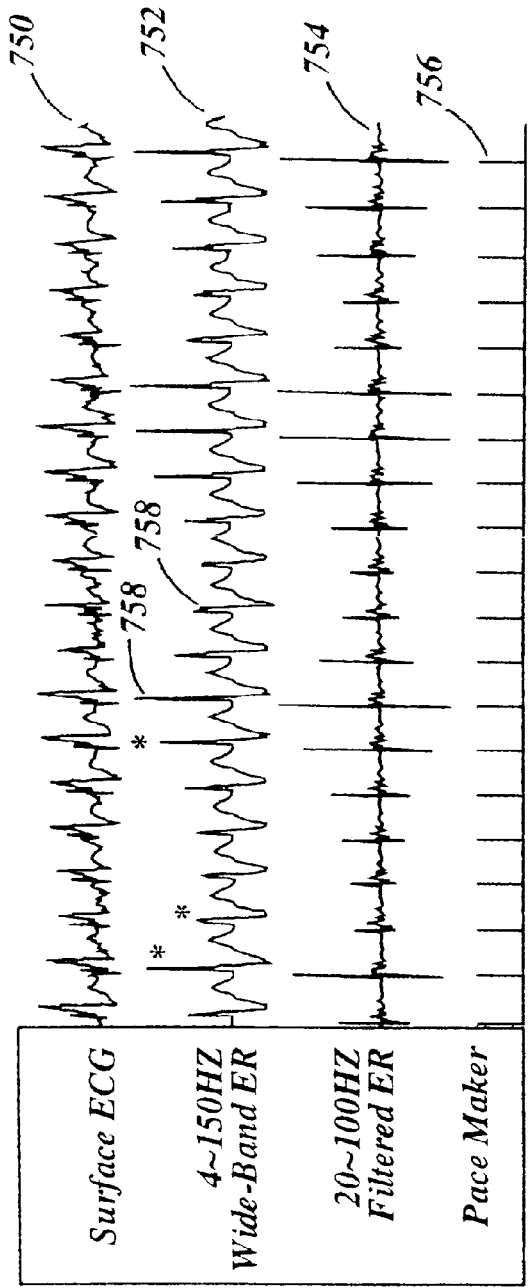
FIG. 47 is a graph of an electrogram and filtered signals shown in association with a pace marker, which together illustrates the modulation of the evoked response amplitude.

Referring to FIG. 47, there is shown a surface electrocardiogram signal 750, a corresponding first waveform 752 of the electrocardiogram signal filtered through a sense amplifier having a wide-band pass filter array, a corresponding second waveform 754 of the electrocardiogram signal filtered through a sense amplifier having a typical band pass filter array and the pacing event marker 756 associated with the resulting electrocardiogram signal. A cardiac depolarization or R-wave deflection 758 is pronounced in the filtered first and second waveforms 752 and 754. The inventors have observed that over several beats the amplitude of the R-wave fluctuates or modulates. Without limitation, the modulation has been found to result from factors such as activity level of the patient, variations in the pacing output voltage, respiration of the patient, administration of pharmaceutical agents, and lead maturation, among others. Modulation due to respiration has been observed as cyclic in nature. These cyclic fluctuations or respiration modulations have been observed in both bi-polar and uni-polar sensing configurations.

Figure 48:
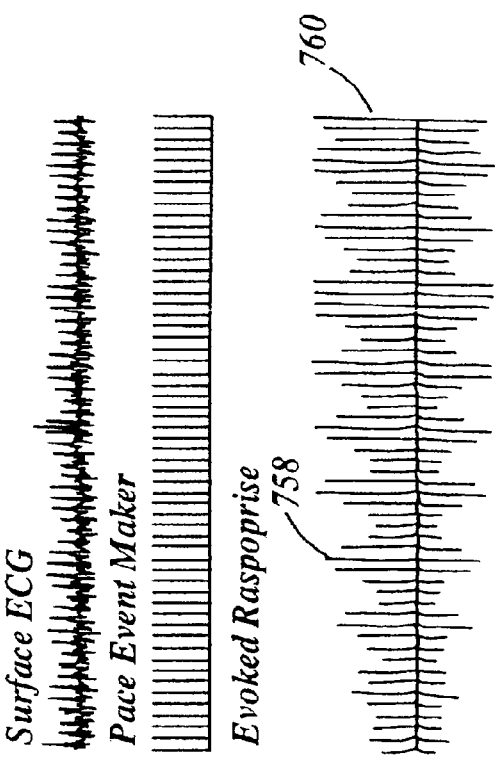
FIG. 48 is a graph of an electrogram and filtered signals shown in association with a pace marker, which together illustrates the modulation of the evoked response amplitude due to respiration modulation.
Figure 49:
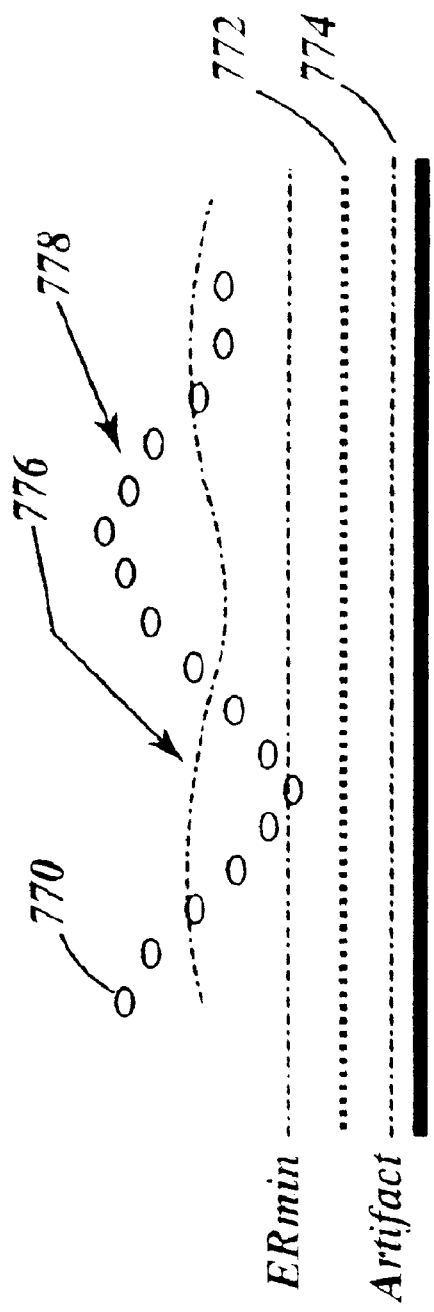
FIG. 49 is a graph of the amplitude of evoked response for several beats, shown relative to the evoked response minimum and evoked response filter.
Figure 50:
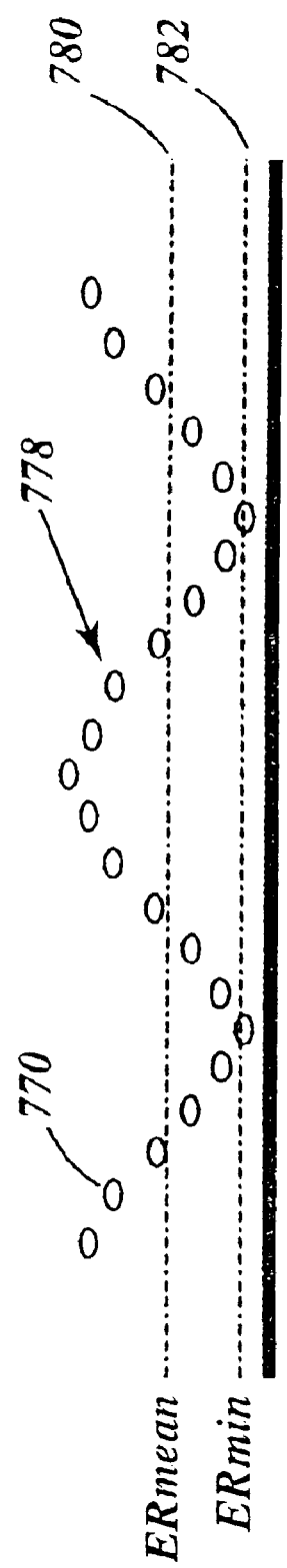
FIG. 50 is a graph of the amplitude of evoked response for several beats, shown relative to the evoked response minimum and evoked response mean.

Referring to FIG. 48, a case study is shown for exemplary purposes, wherein the amplitude of the R-wave 758 for the evoked response waveform 760 fluctuates over a cyclic pattern. The amplitude of each R-wave 758 can be seen to fluctuate over several beats wherein the amplitude of the R-wave having the greatest amplitude is more than twice the amplitude of the R-wave having the smallest amplitude. This modulation in R-wave amplitudes is significant when considering/setting the threshold amplitude that must be detected before an evoked response of the patient's heart is assumed. FIGS. 49 and 50 further illustrate the need to define an evoked response detection threshold sufficient to detect evoked response during an entire respiration modulation, without setting the threshold so low that detected artifacts exceeds the threshold.

Referring to FIG. 49, several points 770 are shown plotted relative to an evoked response detection threshold baseline 772, an artifact baseline 774, and an evoked response filter baseline 776. The resulting modulating waveform 778 is shown in relation to the threshold baseline 772. Each point 770 corresponds to a maximum amplitude for a corresponding evoked response. FIG. 50 shows the modulating waveform 778 in relation to the evoked response "mean" baseline 780 and the evoked response "minimum" baseline 782. The evoked response mean baseline 780 represents the mean of several maximum amplitudes of several R-waves over several beats. Likewise, the evoked response minimum baseline 782 represents the minimum amplitude of several maximum amplitudes of several R-waves over several beats.

Referring now to FIG. 45, the maximum amplitude of several R-waves indicated at point 696 are shown measured over time, wherein the "measurements" of the amplitude occurred during a five-beat step down capture detection pacing protocol. The evoked response detection threshold baseline 698 as determined by the method of the present invention is shown, wherein fluctuation in the baseline coincides with the modulation of the evoked response amplitude. In this manner, during beat by beat autocapture, for example, a decrease in the evoked response amplitude is not likely to generate a false negative in capture decision making, thereby eliminating unnecessary backup pacing.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. An implantable cardiac rhythm management device capable of automatically detecting intrinsic and evoked response of a patient's heart, said rhythm management device including:
   (a) a pulse generator that generates stimulation pulses;
   (b) a controller having a timing circuit, sensing circuit and stimulation circuit for controlling activation of the pulse generator and delivery of the stimulation pulses;
   (c) electrodes for positioning within a patient's heart and electrically coupled to said controller, wherein electrocardiogram signals are electrically conducted to said controller, said electrocardiogram signal including electrical impulses corresponding to a cardiac depolarization and noise;

(d) said sensing circuit coupled to said timing circuit and including an adjustable detection threshold;

(e) wherein said controller detects an evoked response of the patient's heart from the electrocardiogram signal, determines an amplitude associated with the evoked response, and adjusts the detection threshold dependent upon the determined amplitude; and (f) wherein said controller determines a value associated with modulation of the evoked response, wherein said value is determined from the amplitude of a detected evoked response.

2. A rhythm management device as recited in claim 1, wherein the controller adjusts the detection threshold dependant upon the value associated with modulation.

3. A rhythm management device as recited in claim 1, wherein the value associated with modulation is determined from a respiration modulation index and evoked response filter index.

4. A rhythm management device as recited in claim 1, further including a means for determining an amount associated with an artifact baseline of the electrocardiogram signal and further wherein the detection threshold is set greater than the amount associated with the artifact baseline and less than a minimum of maximum amplitudes of the evoked response over a predetermined number of beats.

5. A rhythm management device as recited in claim 1, wherein said controller detects the presence of noise in the electrocardiogram signal.

6. A rhythm management device as recited in claim 5, wherein said controller determines a value associated with an amplitude of the detected noise.

7. A rhythm management device as recited in claim 6, wherein the controller adjusts the detection threshold dependant upon the value associated with the amplitude of the detected noise.

8. A rhythm management device as recited in claim 7, further including memory means for storing the determined value associated with an amplitude of noise over a plurality of detected cardiac depolarization, wherein the controller adjusts the sensing threshold dependant upon the determined value associated with an amplitude of noise corresponding to prior detected cardiac depolarization.

9. A rhythm management device as recited in claim 1, wherein the controller within a first preset time prior to delivering a stimulation pulse analyzes the electrocardiogram signal to determine if an amplitude of a portion of the electrocardiogram signal exceeds a first sensing threshold.

10. An implantable cardiac rhythm management device capable of automatically detecting intrinsic and evoked response of a patient's heart, said rhythm management device including:

(a) a pulse generator that generates stimulation pulses;

(b) a controller having a timing circuit, sensing circuit and stimulation circuit for controlling activation of the pulse generator and delivery of the stimulation pulses;

(c) electrodes for positioning within a patient's heart and electrically coupled to said controller, wherein electrocardiogram signals are electrically conducted to said controller, said electrocardiogram signal including electrical impulses corresponding to a cardiac depolarization and noise;

(d) said sensing circuit coupled to said timing circuit and including an adjustable detection threshold; and (e) wherein said sensing circuit includes a sense amplifier electrically connected to the electrodes and controller in a manner wherein a polarity of an amplitude of the electrocardiogram signal corresponding to an evoked response is opposite a polarity of an amplitude of the electrocardiogram signal corresponding to afterpotential.

11. A rhythm management device as recited in claim 10, wherein a positive pole of the sense amplifier is coupled to an indifferent contact and a negative pole of the sense amplifier is coupled to said electrodes.

12. An implantable cardiac rhythm management device capable of automatically detecting intrinsic and evoked response of a patient's heart, said rhythm management device including:

(a) a pulse generator that generates stimulation pulses;

(b) a controller having a timing circuit, sensing circuit and stimulation circuit for controlling activation of the pulse generator and delivery of the stimulation pulses;

(c) electrodes for positioning within a patient's heart and electrically coupled to said controller, wherein electrocardiogram signals are electrically conducted to said controller, said electrocardiogram signal including electrical impulses corresponding to a cardiac depolarization and noise;

(d) said sensing circuit coupled to said timing circuit and including an adjustable detection threshold;

(e) wherein said stimulation circuit includes a coupling capacitor arrangement that reduces afterpotentials; and (f) wherein said coupling capacitor arrangement includes a capacitor having a capacitance less than 5 microfarads.

13. An implantable cardiac rhythm management device capable of automatically detecting intrinsic and evoked response of a patient's heart, said rhythm management device including:

(a) a pulse generator that generates stimulation pulses;

(b) a controller having a timing circuit, sensing circuit and stimulation circuit for controlling activation of the pulse generator and delivery of the stimulation pulses;

(c) electrodes for positioning within a patient's heart and electrically coupled to said controller, wherein electrocardiogram signals are electrically conducted to said controller, said electrocardiogram signal including electrical impulses corresponding to a cardiac depolarization and noise;

(d) said sensing circuit coupled to said timing circuit and including an adjustable detection threshold; and (e) wherein the sensing circuit includes a pre-amplifier electrically coupled to the electrodes, a first high pass coupling capacitor electrically coupled between the electrodes and said pre-amplifier, and a blanking switch electrically coupled between said high pass coupling capacitor and said pre-amplifier, said sensing circuit further including a dedicated evoked response amplifier.

14. An implantable cardiac rhythm management device capable of automatically detecting intrinsic and evoked response of a patient's heart, said rhythm management device including:

(a) a pulse generator that generates stimulation pulses;

(b) a controller having a timing circuit, sensing circuit and stimulation circuit for controlling activation of the pulse generator and delivery of the stimulation pulses;

(c) electrodes for positioning within a patient's heart and electrically coupled to said controller, wherein electrocardiogram signals are electrically conducted to said controller, said electrocardiogram signal including electrical impulses corresponding to a cardiac depolarization and noise;

(d) said sensing circuit coupled to said timing circuit and including an adjustable detection threshold;

(e) wherein the sensing circuit includes an afterpotential attenuation system for attenuating afterpotentials which result due to delivery of the stimulation pulses; and (f) wherein said afterpotential attenuation means includes a first coupling capacitor operatively coupled to a second coupling capacitor, and a switching system for selectively coupling said second coupling capacitor in series with said first coupling capacitor so as to reduce the effective capacitance of said first and second coupling capacitor.

15. An implantable cardiac rhythm management device capable of automatically detecting intrinsic and evoked response of a patient's heart, said rhythm management device including:

(a) a pulse generator that generates stimulation pulses;

(b) a controller having a timing circuit, sensing circuit and stimulation circuit for controlling activation of the pulse generator and delivery of the stimulation pulses;

(c) electrodes for positioning within a patient's heart and electrically coupled to said controller, wherein electrocardiogram signals are electrically conducted to said controller, said electrocardiogram signal including electrical impulses corresponding to a cardiac depolarization and noise;

(d) said sensing circuit coupled to said timing circuit and including an adjustable detection threshold, said sensing circuit including a sense amplifier electrically connected to the electrodes and controller in a manner wherein a polarity of an amplitude of the electrocardiogram signal corresponding to an evoked response is opposite a polarity of an amplitude of the electrocardiogram signal corresponding to afterpotential; and (e) wherein said controller detects an evoked response of the patient's heart from the electrocardiogram signal, determines an amplitude associated with the evoked response, and adjusts the detection threshold dependent upon the determined amplitude.

16. A rhythm management device as recited in claim 15, wherein said controller determines a value associated with modulation of the evoked response, wherein said value is determined from the amplitude of a detected evoked response.

17. A rhythm management device as recited in claim 16, wherein the controller adjusts the detection threshold dependant upon the value associated with modulation.

18. A rhythm management device as recited in claim 16, wherein the value associated with modulation is determined from a respiration modulation index and evoked response filter index.

19. A rhythm management device as recited in claim 15, further including a device for determining an amount associated with an artifact baseline of the electrocardiogram signal and further wherein the detection threshold is set greater than the amount associated with the artifact baseline and less than a minimum of maximum amplitudes of the evoked response over a predetermined number of beats.

20. A rhythm management device as recited in claim 15, wherein the controller within a first preset time prior to delivering a stimulation pulse analyzes the electrocardiogram signal to determine if an amplitude of a portion of the electrocardiogram signal exceeds a first sensing threshold.

21. An implantable cardiac rhythm management device capable of automatically detecting intrinsic and evoked response of a patient's heart, said rhythm management device including:

(a) a pulse generator that generates stimulation pulses;

(b) a controller having a timing circuit, sensing circuit and stimulation circuit for controlling activation of the pulse generator and delivery of the stimulation pulses;

(c) electrodes for positioning within a patient's heart and electrically coupled to said controller, wherein electrocardiogram signals are electrically conducted to said controller, said electrocardiogram signal including electrical impulses corresponding to a cardiac depolarization and noise;

(d) said sensing circuit coupled to said timing circuit and including an adjustable detection threshold, said sensing circuit including a sense amplifier electrically connected to the electrodes and controller in a manner wherein a polarity of an amplitude of the electrocardiogram signal corresponding to an evoked response is opposite a polarity of an amplitude of the electrocardiogram signal corresponding to afterpotential; and (e) wherein said stimulation circuit includes a coupling capacitor arrangement that reduces afterpotentials; and (f) wherein said coupling capacitor arrangement includes a capacitor having a capacitance less than 5 microfarads.

22. A rhythm management device as recited in claim 21, wherein the sensing circuit includes a pre-amplifier electrically coupled to the electrodes, a first high pass coupling capacitor electrically coupled between the electrodes and said pre-amplifier, and a blanking switch electrically coupled between said high pass coupling capacitor and said pre-amplifier, said sensing circuit further including a dedicated evoked response amplifier.

23. An implantable cardiac rhythm management device capable of automatically detecting intrinsic and evoked response of a patient's heart, said rhythm management device including:

(a) a pulse generator that generates stimulation pulses;

(b) a controller having a timing circuit, sensing circuit and stimulation circuit for controlling activation of the pulse generator and delivery of the stimulation pulses;

(c) electrodes for positioning within a patient's heart and electrically coupled to said controller, wherein electrocardiogram signals are electrically conducted to said controller, said electrocardiogram signal including electrical impulses corresponding to a cardiac depolarization and noise;

(d) said sensing circuit coupled to said timing circuit and including an adjustable detection threshold, said sensing circuit including a sense amplifier electrically connected to the electrodes and controller in a manner wherein a polarity of an amplitude of the electrocardiogram signal corresponding to an evoked response is opposite a polarity of an amplitude of the electrocardiogram signal corresponding to afterpotential; and (e) wherein the sensing circuit includes an afterpotential attenuation system for attenuating afterpotentials which result due to delivery of the stimulation pulses; and (f) wherein said afterpotential attenuation means includes a first coupling capacitor operatively coupled to a second coupling capacitor, and a switching device for selectively coupling said second coupling capacitor in series with said first coupling capacitor so as to reduce the effective capacitance of said first and second coupling capacitor.

24. An implantable cardiac rhythm management device capable of automatically detecting intrinsic and evoked response of a patient's her, said rhythm management device including:
(a) a pulse generator that generates stimulation pulses;
(b) a controller having a timing circuit, sensing circuit and stimulation circuit for controlling activation of the pulse generator and delivery of the stimulation pulses;
(c) electrodes positioned within a patient's heart and electrically coupled to said controller, wherein electrocardiogram signals are electrically conducted to said controller, said electrocardiogram signal including electrical impulses corresponding to a cardiac depolarization and noise;
(d) said sensing circuit coupled to said timing circuit and including an adjustable detection threshold, said sensing circuit including a sense amplifier electrically connected to the electrodes and controller in a manner wherein a polarity of an amplitude of the electrocardiogram signal corresponding to an evoked response is opposite a polarity of an amplitude of the electrocardiogram signal corresponding to afterpotential;
(e) wherein said controller detects the presence of noise in the electrocardiogram signal; and
(f) wherein said controller determines a value associated with an amplitude of the detected noise.

25. A rhythm management device as recited in claim 24, wherein the controller adjusts the detection threshold dependant upon the value associated with the amplitude of the detected noise.

26. A rhythm management device as recited in claim 24, further including memory means for storing the determined value associated with an amplitude of noise over a plurality of detected cardiac depolarization, wherein the controller adjusts the sensing threshold dependant upon the determined value associated with an amplitude of noise corresponding to prior detected cardiac depolarization.

27. An implantable cardiac rhythm management device capable of automatically detecting intrinsic and evoked response of a patient's heart, said rhythm management device including:
(a) means for generating stimulation pulses;
(b) control means for controlling activation of said means for generating stimulation pulses and for controlling delivery of stimulation pulses, said control means having a timing circuit, sensing circuit and stimulation circuit;
(c) electrodes for positioning within a patient's heart and electrically coupled to said control means such that electrocardiogram signals are electrically conducted to said control means, said electrocardiogram signal including electrical impulses corresponding to a cardiac depolarization and noise, said control means determines a value associated with an amplitude of the detected noise;
(d) said sensing circuit coupled to said timing circuit and including an adjustable detection threshold, wherein said control means adjusts the detection threshold dependant upon the value associated with the amplitude of the detected noise; and
(e) wherein said control means detects an evoked response of the patient's heart from the electrocardiogram signal, determines an amplitude associated with the evoked response, and further adjusts the detection threshold dependent upon the determined amplitude.

28. A rhythm management device as recited in claim 27, wherein said control means determines a value associated with modulation of the evoked response, wherein said value is determined from the amplitude of a detected evoked response.

29. A rhythm management device as recited in claim 28, wherein the control means adjusts the detection threshold dependant upon the value associated with modulation.

30. A rhythm management device as recited in claim 28, wherein the value associated with modulation is determined from a respiration modulation index and evoked response filter index.

31. A rhythm management device as recited in claim 27, further including a means for determining an amount associated with an artifact baseline of the electrocardiogram signal and further wherein the detection threshold is set greater than the amount associated with the artifact baseline and less than a minimum of maximum amplitudes of the evoked response over a predetermined number of beats.

32. A rhythm management device as recited in claim 27, wherein said sensing circuit includes a sense amplifier electrically connected to the electrodes and control means in a manner wherein a polarity of an amplitude of the electrocardiogram signal corresponding to an evoked response is opposite a polarity of an amplitude of the electrocardiogram signal corresponding to afterpotential.

33. A rhythm management device as recited in claim 32, wherein a positive pole of the sense amplifier is coupled to an indifferent contact and a negative pole of the sense amplifier is coupled to said electrodes.

34. A rhythm management device as recited in claim 27, wherein said stimulation circuit includes a coupling capacitor arrangement that reduces afterpotentials.

35. A rhythm management device as recited in claim 34, wherein coupling capacitor arrangement includes a capacitor having a capacitance less than 5 microfarads.

36. A rhythm management device as recited in claim 27, wherein the sensing circuit includes a pre-amplifier electrically coupled to the electrodes, a first high pass coupling capacitor electrically coupled between the electrodes and said pre-amplifier, and a blanking switch electrically coupled between said high pass coupling capacitor and said pre-amplifier, said sensing circuit further including a dedicated evoked response amplifier.

37. A rhythm management device as recited in claim 27, wherein the sensing circuit includes an afterpotential attenuation means for attenuating afterpotentials which result due to delivery of the stimulation pulses.

38. A rhythm management device as recited in claim 37, wherein said afterpotential attenuation means includes a first coupling capacitor operatively coupled to a second coupling capacitor, and a switching means for selectively coupling said second coupling capacitor in series with said first coupling capacitor so as to reduce the effective capacitance of said first and second coupling capacitor.

39. A rhythm management device as recited in claim 27, wherein the control means within a first preset time prior to delivering a stimulation pulse analyzes the electrocardiogram signal to determine if an amplitude of a portion of the electrocardiogram signal exceeds a first sensing threshold.

40. An implantable cardiac rhythm management device capable of automatically detecting intrinsic and evoked response of a patient's heart, said rhythm management device including:

(a) means for generating stimulation pulses;
(b) control means for controlling activation of said means for generating stimulation pulses and for controlling delivery of stimulation pulses, said control means having a timing circuit, sensing circuit and stimulation circuit;
(c) electrodes for positioning within a patient's heart and electrically coupled to said control means such that electrocardiogram signals are electrically conducted to said control means, said electrocardiogram signal including electrical impulses corresponding to a cardiac depolarization and noise, said control means determines a value associated with an amplitude of the detected noise;
(d) said sensing circuit coupled to said timing circuit and including an adjustable detection threshold, wherein said control means adjusts the detection threshold dependant upon the value associated with the amplitude of the detected noise; and
(e) memory means for storing the determined value associated with an amplitude of noise over a plurality of detected cardiac depolarization, wherein the control means adjusts the sensing threshold dependant upon the determined value associated with an amplitude of noise corresponding to prior detected cardiac depolarization.

* * * * *